US007012074B2

(12) United States Patent
Bjorsne et al.

(10) Patent No.: US 7,012,074 B2
(45) Date of Patent: Mar. 14, 2006

(54) 3,8-DIAZABICYCLO[3.2.1]OCTANES AND THEIR USE IN THE TREATMENT OF CARDIAC ARRHYTHMIAS

(75) Inventors: Magnus Bjorsne, Molndal (SE); Kurt-Jürgen Hoffmann, Mölndal (SE); Fritiof Pontén, Molndal (SE); Gert Strandlund, Molndal (SE); Peder Svensson, Göteborg (SE); Michael Wilstermann, Mölndal (SE)

(73) Assignee: AstraZeneca AB, Sodertalje (SE)

( * ) Notice: Subject to any disclaimer, the term of this patent is extended or adjusted under 35 U.S.C. 154(b) by 97 days.

(21) Appl. No.: 10/399,663

(22) PCT Filed: Oct. 18, 2001

(86) PCT No.: PCT/SE01/02994

§ 371 (c)(1),
(2), (4) Date: May 8, 2003

(87) PCT Pub. No.: WO02/32902

PCT Pub. Date: Apr. 25, 2002

(65) Prior Publication Data

US 2004/0023971 A1    Feb. 5, 2004

(30) Foreign Application Priority Data

Oct. 20, 2000  (SE) .................................. 0003795

(51) Int. Cl.
*A01N 43/58* (2006.01)
(52) U.S. Cl. ................................................... 514/249
(58) Field of Classification Search ................. 514/249
See application file for complete search history.

(56) References Cited

U.S. PATENT DOCUMENTS

| 3,281,421 A | 10/1966 | Cignarella et al. .......... 260/268 |
| 3,328,396 A | 6/1967 | Kirchner et al. ............ 260/243 |
| 3,962,449 A | 6/1976 | Binnig et al. ......... 260/293.55 |
| 4,459,301 A | 7/1984 | Binnig et al. ............... 424/267 |
| 4,550,112 A | 10/1985 | Schoen et al. .............. 514/278 |
| 4,556,662 A | 12/1985 | Binnig et al. ............... 514/300 |
| 4,571,396 A | 2/1986 | Hutt et al. .................. 514/249 |
| 4,780,468 A | 10/1988 | Bridges et al. ............. 514/312 |
| 5,140,033 A | 8/1992 | Schriewer et al. .......... 514/312 |
| 5,468,858 A | 11/1995 | Berlin et al. .................. 546/18 |

FOREIGN PATENT DOCUMENTS

| DE | 14 45 993 | | 6/1962 |
| DE | 37 02 393 A1 | | 1/1987 |
| DE | 37 21 745 A1 | | 7/1987 |
| EP | 0 136 945 A2 | | 4/1985 |
| EP | 0 157 174 A1 | | 10/1985 |
| EP | 0 230 274 A2 | | 7/1987 |
| EP | 0 251 308 A1 | | 1/1988 |
| EP | 0 266 576 A2 | | 5/1988 |
| EP | 0 304 087 A2 | | 2/1989 |
| EP | 0 306 871 A2 | | 3/1989 |
| EP | 0 308 843 A2 | | 3/1989 |
| EP | 0 393 400 A2 | | 10/1990 |
| EP | 0 470 578 A1 | | 2/1992 |
| EP | 0 596 126 A1 | | 5/1994 |
| EP | 0 614 664 A1 | | 9/1994 |
| EP | 0 665 228 A1 | | 8/1995 |
| EP | 0 700 912 A1 | | 3/1996 |
| EP | 0 825 186 A1 | | 2/1998 |
| FR | 2099683 | | 3/1972 |
| FR | 2 531 709 | | 2/1984 |
| GB | 949088 | | 2/1964 |
| GB | 1180060 | | 2/1970 |
| GB | 2 295 387 A | | 5/1996 |
| WO | WO 88/02627 | | 4/1988 |
| WO | WO 91/07405 | | 5/1991 |
| WO | WO 93/20078 | | 10/1993 |
| WO | WO 94/16698 | | 8/1994 |
| WO | WO 95/18129 | | 7/1995 |
| WO | WO 95/23152 | | 8/1995 |
| WO | WO 96/04254 | | 2/1996 |
| WO | WO 96/33172 | | 10/1996 |
| WO | WO 9635686 | | 11/1996 |
| WO | WO 99/31100 | | 6/1999 |
| WO | WO 00/59510 | | 10/2000 |

OTHER PUBLICATIONS

Crijns et al, "Atrial Flutter can be Terminated by a Class III Antiarrhythmic Drug but not by a Class IC Drug" European Heart Journal, vol. 15(10), pp. 1403-1408 (Oct. 1994).*
Foster et al, "Ibutilide: A Review of its Pharmacological Properties and Clinical Potential in the Acute Management of Atrial Flutter and Fibrillation" Drugs, vol. 54(2), pp. 312-330 (Aug. 1997).*
Kellow, "Motility-Like Dyspepsia" the Medical Journal of Australia, vol. 157, pp. 385-388 (1992).*
Stoddard et al, "Electrical Arrhythmias in the Human Stomach" Gut, vol. 22, pp. 705-712 (1981).*
Corvert® (ibutilide fumarate injection) Prescribing Information © 2002 Pharmacia & Upjohn Company.*
Tikosyn® (dofetilide) Prescribing Information © 2004 Pfizer Labs.*
Cignarella, G. et al; "Benzocondensed derivatives as rigid analogues of the μ-opioid agonist 3(8)-cinnamyl-8(3)-propionyl-3,8-diazabicyclo[3.2.1]octanes: synthesis, modeling, and affinity" Table 1; *IL Farmaco* 53 pp. 667-674 (1998).

(Continued)

*Primary Examiner*—James O. Wilson
*Assistant Examiner*—Zachary C. Tucker
(74) *Attorney, Agent, or Firm*—Nixon & Vanderhye

(57) ABSTRACT

There is provided compounds of formula (I), wherein $R^1$, $R^2$ and $R^a$ to $R^b$ have meanings given in the description, which are useful in the prophylaxis and in the treatment of arrhythmias, in particular atrial and ventricular arrhythmias.

29 Claims, No Drawings

OTHER PUBLICATIONS

Barlocco, D. et al.; "Mono- and Disubstituted-3,8-diazabicyclo[3.2.1]octane Derivatives as analgesics Structurally Related to Epibatidine: Synthesis, Activity, and Modeling"; Table 1, Scheme 2; *J. Med. Chem.*, 41, pp. 674-681 (1998).

"The Cardiac Arrhythmia Suppression Trial (CAST)"; reported in *New England Journal of Medicine*, 321, No. 6, pp 406-412 (1989).

Garrison, G.L., et al; "Novel 3,7-Diheterabicyclo[3.3.1]nonanes That Possess Perdominant Class III Antiarrhythmic Activity in 1-4 Day Post Infraction Dog Models: X-ray Diffraction Analysis of 3-[4-(1 H-Imidazol-1-yl)benzoyl]-7-isopropyl-3,7-diazabicyclo[3.3.1]nonane Dihydroperchlorate"; *J. Med. Chem.*; 39, pp. 2559-2570 (1996).

Paroczai, M., et al; "Investigations to Characterize a New Antiarrhythmic Drug Bisaramil"; *Pharmacological Research*; 24, No. 2, pp. 149-162 (1991).

Wang, J., et al; "Class III Antiarrhythmic Drug Action in Experimental Atrial Fibrillation"; *Circulation*, 90, pp. 2032-2041 (1994).

Chen, C.L. et al; "High-Performance Liquid Chromatographic Determination of SAZ-VII-22, a Novel Antiarrhythmic Agent, in Dog Plasma and Urine"; *Analytical Sciences*;9, pp. 429-431 (1993).

Fontanella, L. et al; "Analoghi Biciclici Della Piperazina"; *IL Farmaco*—Ed. Sci.; vol. 27(9), pp. 755-772, (1972).

Fontanella, L. et al; "Analoghi Biciclici Della Piperazina"; *IL Farmaco—Ed. Sci.*; vol. 30(9), pp. 742-753, (1975).

Occelli, E. et al; "Omologhi Biciclici Della Piperazina"; *IL Farmaco—Ed. Sci.*; vol. 33(6), pp. 402-420, (1978).

Occelli, E., et al; "Omologhi Triciclici Della Piperazina"; *IL Farmaco—Ed. Sci*, vol. 33(11), pp. 875-884, (1978).

Occelli, E., et al; "Sintesi Ed Attivita Farmacologica Di Derivati Di 3-Aminopropiofenoni E DI 3-Aminometiilcanfore"; *IL Farmaco—Ed. Sci.*; vol. 40(2), pp. 86-101, (1985).

Cignarella, G., et al; "Interaction of 3,8-Diazabicyclo (3.2.1) Octanes with Mu and Delta Opioid Receptors"; *Pharmacol. Res. Commun.*; vol. 20, No. 5, pp. 383-394 (1988).

Barlocco, E., et al; "Synthesis and µ-opioid receptor affinity of a new series of nitro substituted 3,8-diazabicyclo[3.2.1] octane derivatives"; *IL Farmaco* 53, pp. 557-562, (1998).

Sturm, P.A., et al; "Antifilarial Agents. Diazabicyclooctanes and Diazabicycloheptanes as Bridged Analogs of Diethylcarbamazine"; *Journal of Medicinal Chemistry*; vol. 17, No. 5, pp. 481-487 (1974).

Occelli, E., et al; "Analoghi Biciclici Della Piperazina"; *IL Farmaco—Ed Sci.*; vol. 32(4), pp. 237-247 (1977).

Cignarella, G., et al; "Strutture tricicliche derivanti dal 3,8-diazabiciclo[3.2.1] ottano.—Nota I. Sintesi e proprieta del 3,8-diazatriciclo[3.2.1.2$^{3,8}$]decano."; *Gazz. Chim. Ital.*; vol. 98(7), pp. 848-860 (1968).

Pifferi, G., et al; "1H-2,3-Benzoxazine and Derivatives-III""; *Tetrahedron*, vol. 24, pp. 4923-4932 (1968).

Barlocco, D., et al; "Synthesis and Opioid receptor affinity of Bivalent Ligands Derived from 3,8-Diazabicyclo(3.2.1) Octanes"; *IL Farmaco*, vol. 48(3), pp. 387-396, (1993).

Garrison, G.L., et al; "Novel 3,7-Diheterabicyclo[3.3.1] nonanes That Possess Predominant Class III Antiarrhythmic Activity in 1-4 Day Post Infraction Dog Models: X-ray Diffraction Analysis of 3-[4-(1 H-Imidazol-1-yl)benzoyl]-7-isopropyl-3,7-diazabicyclo[3.3.1] nonane Dihydroperchlorate"; *J. Med. Chem.*; 39, pp. 2559-2570 (1996).

Axenborg, J.E. et al; "A PC-based on-line system for physiological in vivo and in vitro experiments"; *Computer Methods and Programs in Biomedicine*, 41, pp. 55-67 (1993).

* cited by examiner

3,8-DIAZABICYCLO[3.2.1]OCTANES AND THEIR USE IN THE TREATMENT OF CARDIAC ARRHYTHMIAS

This application is the U.S. national phase of international application PCT/SE01/02294, filed 18 Oct. 2001, which designated the U.S.

1. Field of the Invention

This invention relates to the use of pharmaceutically useful compounds, some of which are novel, in the treatment of cardiac arrhythmias.

2. Background and Prior Art

Cardiac arrhythmias may be defined as abnormalities in the rate, regularity, or site of origin of the cardiac impulse or as disturbances in conduction which causes an abnormal sequence of activation. Arrhythmias may be classified clinically by means of the presumed site of origin (i.e. as supraventricular, including atrial and atrioventricular, arrhythmias and ventricular arrhythmias) and/or by means of rate (i.e. bradyarrhythmias (slow) and tachyarrhythmias (fast)).

In the treatment of cardiac arrhythmias, the negative outcome in clinical trials (see, for example, the outcome of the Cardiac Arrhythmia Suppression Trial (CAST) reported in New England Journal of Medicine, 321, 406 (1989)) with "traditional" antiarrhythmic drugs, which act primarily by slowing the conduction velocity (class I antiarrhythmic drugs), has prompted drug development towards compounds which selectively delay cardiac repolarization, thus prolonging the QT interval. Class III antiarrhythmic drugs may be defined as drugs which prolong the transmembrane action potential duration (which can be caused by a block of outward $K^+$ currents or from an increase of inward ion currents) and refractoriness, without affecting cardiac conduction.

One of the key disadvantages of hitherto known drugs which act by delaying repolarization (class III or otherwise) is that they all are known to exhibit a unique form of proarrhythmia known as torsades de pointes (turning of points), which may, on occasion be fatal. From the point of view of safety, the minimisation of this phenomenon (which has also been shown to be exhibited as a result of administration of non-cardiac drugs such as phenothiazines, tricyclic antidepressants, antihistamines and antibiotics) is a key problem to be solved in the provision of effective antiarrhythmic drugs.

Antiarrhythmic drugs based on bispidines (3,7-diazabicyclo[3.3.1]nonanes), are known from inter alia international patent applications WO 91/07405 and WO 99/31100, European patent applications 306 871, 308 843 and 665 228 and U.S. Pat. Nos. 3,962,449, 4,556,662, 4,550,112, 4,459,301 and 5,468,858, as well as journal articles including inter alia: *J. Med. Chem.* 39, 2559, (1996); *Pharmacol. Res.* 24, 149 (1991); *Circulation* 90, 2032 (1994); and *Anal. Sci.* 9, 429, (1993). 3,8-Diazabicyclo[3.2.1]octane compounds are neither disclosed nor suggested in any of these documents.

Analgesic compounds based on 3,8-diazabicyclo[3.2.1]octane are known from inter alia international patent applications WO 94/16698 and WO 95/23152, German patent application 14 45 993, British patent application 949,088, U.S. Pat. No. 3,281,421, as well as journal articles including inter alia: *Il Farmaco—Ed. Sci.* 27(9), 755 (1972); ibid. 30(9), 742 (1975); ibid. 33(6), 401 (1978); ibid. 33(11), 875 (1978); ibid. 40(2), 86 (1985); *Pharmacol. Res. Commun.* 20(5), 383 (1988); and *J. Med. Chem.* 41, 674 (1998).

Antibacterial compounds based on 3,8-diazabicyclo[3.2.1]octane are known from inter alia international patent application WO 88/02627, European patent applications 159 174, 230 274, 251 308, 266 576, 304 087, 393 400, 470 578, 596 126 and 700 912, German patent applications 37 02 393 and 37 21 745 and U.S. Pat. Nos. 4,571,396, 4,780,468 and 5,140,033.

Compounds based on 3,8-diazabicyclo[3.2.1]octane are known for use in a variety of other medical applications, including, inter alia: the inhibition of cell adhesion (as described in EP 614 664); the treatment of benign prostatic hyperplasia (as described in GB 2,295,387); the treatment of head injury, subarachnoid hemorrhage and the reduction of mucous formation in the lung (as described in WO 93/20078); the activation of the immune system (as described in EP 825 186); the inhibition of matrix metalloproteinases (as described in WO 96/33172); and the stimulation of cerebral activity (as described in EP 136 945).

Additional medical applications of compounds based on 3,8-diazabicyclo[3.2.1]octane are known including, inter alia, their use as: cholecystokinin antagonists (as described in WO 96/04254); dehydrogenase inhibitors (as described in WO 00/59510); $\mu$-opioid receptor agonists or antagonists (as described in *Il Farmaco* 53, 557 and 667 (1998)); sedatives (as described in FR 2,531,709); anti-inflammatory agents (as described in GB 1,180,060); spasmolytic or local anaesthetic agents (as described in U.S. Pat. No. 3,328,396); antifilarial agents (as described in *J. Med. Chem.* 17(5), 481 (1974)); and antiparkinson agents (as described in *Il Farmaco—Ed. Sci.* 32(4), 237 (1977)).

Further 3,8-diazabicyclo[3.2.1]octane compounds are known as chemical curiosities from inter alia French patent application 2,099,683 as well as journal articles including inter alia: *Gazz. Chim. Ital.* 98(7), 848 (1968); *Tetrahedron* 24, 4923 (1968); and *Il Farmaco* 48(3), 387 (1993).

None of the prior art documents mentioned above that relate to 3,8-diazabicyclo[3.2.1]octanes disclose or provide any suggestion that the compounds disclosed therein may be useful in the treatment of cardiac arrhythmias.

We have surprisingly found that a novel group of 3,8-diazabicyclo[3.2.1]octane-based compounds exhibit electrophysiological activity, preferably class III electrophysiological activity, and are therefore expected to be useful in the treatment of cardiac arrhythmias.

DISCLOSURE OF THE INVENTION

According to the invention there is provided the use of a compound of formula I,

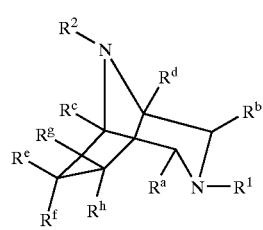

wherein one of $R^1$ and $R^2$ represents $R^{1a}$ and the other represents a fragment of the formula Ia,

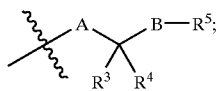

Ia $R^{1a}$ represents $C_{1-12}$ alkyl (optionally substituted and/or terminated by one or more groups selected from halo, cyano, nitro, aryl, Het$^1$, —C(O)R$^{7a}$, —OR$^{7b}$, —N(R$^8$)R$^{7c}$, —C(O)XR$^9$, —C(O)N(R$^{10}$)R$^{7d}$ and —S(O)$_2$R$^{11}$), Het$^2$, —C(O)R$^{7a}$, —C(O)XR$^9$, —C(O)N(R$^{10}$)R$^{7d}$ or —S(O)$_2$R$^{11}$;

$R^{7a}$ to $R^{7d}$ independently represent, at each occurrence when used herein, H, $C_{1-6}$ alkyl (optionally substituted and/or terminated by one or more substituents selected from —OH, $C_{1-6}$ alkoxy, halo, cyano, nitro, aryl, Het$^3$ and —NHC(O)R$^{12}$), aryl or Het$^4$, or R$^{7d}$, together with R$^{10}$, represents $C_{3-6}$ alkylene (which alkylene group is optionally interrupted by an O atom and/or is optionally substituted by one or more $C_{1-3}$ alkyl groups);

$R^{12}$ represents H, $C_{1-4}$ alkyl (optionally substituted and/or terminated by one or more substituents selected from halo, cyano, aryl and —NHC(O)R$^{13}$) or aryl;

$R^{13}$ represents H, $C_{1-4}$ alkyl or aryl;

$R^8$ represents H, $C_{1-6}$ alkyl (optionally substituted and/or terminated by one or more substituents selected from —OH, halo, cyano, nitro and aryl), aryl, —C(O)R$^{14a}$ or —C(O)OR$^{14b}$;

$R^{14a}$ and $R^{14b}$ represent $C_{1-6}$ alkyl (optionally substituted and/or terminated by one or more substituents selected from —OH, halo, cyano, nitro and aryl) or aryl, or R$^{14a}$ represents H;

X represents O or S;

$R^9$ represents, at each occurrence when used herein, aryl or $C_{1-12}$ alkyl (which alkyl group is optionally substituted and/or terminated by one or more substituents selected from —OH, halo, cyano, nitro, aryl, $C_{1-6}$ alkoxy, —SO$_2$R$^{15}$ and Het$^5$);

$R^{15}$ represents $C_{1-6}$ alkyl or aryl;

$R^{10}$ represents, at each occurrence when used herein, H, $C_{1-12}$ alkyl, $C_{1-6}$ alkoxy (which latter two groups are optionally substituted and/or terminated by one or more substituents selected from —OH, halo, cyano, nitro, $C_{1-4}$ alkyl and $C_{1-4}$ alkoxy), -D-aryl, -D-aryloxy, -D-Het$^6$, -D-N(H)C(O)R$^{16a}$, -D-S(O)$_2$R$^{17a}$, -D-C(O)R$^{16b}$, -D-C(O)OR$^{17b}$, -D-C(O)N(R$^{16c}$)R$^{16d}$, or R$^{10}$, together with R$^{7d}$, represents $C_{3-6}$ alkylene (which alkylene group is optionally interrupted by an O atom and/or is optionally substituted by one or more $C_{1-3}$ alkyl groups);

$R^{16a}$ to $R^{16d}$ independently represent H, $C_{1-6}$ alkyl (optionally substituted and/or terminated by one or more substituents selected from —OH, halo, cyano, nitro and aryl), aryl, or R$^{16c}$ and R$^{16d}$ together represent $C_{3-6}$ alkylene;

$R^{17a}$ and $R^{17b}$ independently represent $C_{1-6}$ alkyl (optionally substituted and/or terminated by one or more substituents selected from —OH, halo, cyano, nitro and aryl) or aryl;

D represents a direct bond or $C_{1-6}$ alkylene;

$R^{11}$ represents, at each occurrence when used herein, $C_{1-6}$ alkyl (optionally substituted and/or terminated by one or more substituents selected from —OH, halo, cyano, nitro and aryl), aryl or Het$^7$;

$R^3$ represents H, halo, $C_{1-6}$ alkyl, -E-OR$^{18}$, -E-N(R$^{19}$)R$^{20}$ or, together with R$^4$, represents =O;

$R^4$ represents H, $C_{1-6}$ alkyl or, together with R$^3$, represents =O;

$R^{18}$ represents H, $C_{1-6}$alkyl, -E-aryl, -E-Het$^8$, —C(O)R$^{21a}$, —C(O)OR$^{21b}$ or —C(O)N(R$^{22a}$)R$^{22b}$;

$R^{19}$ represents H, $C_{1-6}$ alkyl, -E-aryl, -E-Het$^8$, —C(O)R$^{21a}$, —C(O)OR$^{21b}$, —S(O)$_2$R$^{21c}$, [C(O)]$_p$N(R$^{22a}$)R$^{22b}$ or —C(NH)NH$_2$;

$R^{20}$ represents H, $C_{1-6}$ alkyl, -E-aryl or —C(O)R$^{21d}$;

$R^{21a}$ to $R^{21d}$ independently represent, at each occurrence when used herein, $C_{1-6}$ alkyl (optionally substituted and/or terminated by one or more substituents selected from halo, aryl and Het$^9$), aryl, Het$^{10}$, or R$^{21a}$ and R$^{21d}$ independently represent H;

$R^{22a}$ and $R^{22b}$ independently represent, at each occurrence when used herein, H or $C_{1-6}$ alkyl (optionally substituted and/or terminated by one or more substituents selected from halo, aryl and Het$^{11}$), aryl, Het$^{12}$, or together represent $C_{3-6}$ alkylene, optionally interrupted by an O atom;

E represents, at each occurrence when used herein, a direct bond or $C_{1-4}$ alkylene;

p represents 1 or 2;

A represents -G-, -J-N(R$^{24}$)— or -J-O— (in which latter two groups, N(R$^{24}$)— or O— is attached to the carbon atom bearing R$^3$ and R$^4$);

B represents -Z-, -Z-N(R$^{25}$)—, —N(R$^{25}$)-Z-, -Z-S(O)$_n$—, -Z-O— (in which latter two groups, Z is attached to the carbon atom bearing R$^3$ and R$^4$);

G represents $C_{1-6}$ alkylene;

J represents $C_{2-6}$ alkylene;

Z represents a direct bond or $C_{1-4}$ alkylene;

$R^{24}$ and $R^{25}$ independently represent H or $C_{1-6}$ alkyl;

$R^5$ represents aryl or Het$^{13}$, both of which groups are optionally substituted by one or more substituents selected from —OH, cyano, halo, $C_{1-6}$ alkyl (optionally terminated by —N(H)C(O)OR$^{26a}$), $C_{1-6}$ alkoxy, Het$^1$, aryl, —C(O)R$^{27c}$, —C(O)OR$^{27d}$, —C(O)N(R$^{27e}$)R$^{27f}$, —N(R$^{27i}$)C(O)N(R$^{27j}$)R$^{27k}$, —S(O)$_n$R$^{26c}$, —OS(O)$_2$R$^{26d}$, —S(O)$_2$N(R$^{27m}$)R$^{27p}$ and (in the case of Het$^{13}$ only) oxo;

Het$^{13}$ represents a four- to twelve-membered heterocyclic group containing one or more heteroatoms selected from oxygen, nitrogen and/or sulfur;

Het$^1$ to Het$^{12}$ independently represent, at each occurrence when used herein, four- to twelve-membered heterocyclic groups containing one or more heteroatoms selected from oxygen, nitrogen and/or sulfur, which heterocyclic groups are optionally substituted by one or more substituents including =O, —OH, cyano, halo, nitro, $C_{1-6}$ alkyl (optionally terminated by —N(H)C(O)OR$^{26a}$), $C_{1-6}$ alkoxy, Het$^1$, aryl, —N(R$^{27a}$)R$^{27b}$, —C(O)R$^{27c}$, —C(O)OR$^{27d}$, —C(O)N(R$^{27e}$)R$^{27f}$, —N(R$^{27g}$)C(O)R$^{27h}$, —N(R$^{27i}$)C(O)N(R$^{27j}$)R$^{27k}$, —N(R$^{27m}$)S(O)$_2$R$^{26b}$, —S(O)$_n$R$^{26c}$, —OS(O)$_2$R$^{26d}$ and —S(O)$_2$N(R$^{27n}$)R$^{27p}$;

$R^{26a}$ to $R^{26d}$ independently represent, at each occurrence when used herein, $C_{1-6}$ alkyl;

$R^{27a}$ to $R^{27p}$ independently represent, at each occurrence when used herein, H or $C_{1-6}$ alkyl;

n represents, at each occurrence, 0, 1 or 2; and $R^a$ to $R^h$ independently represent H or $C_{1-4}$ alkyl;

wherein each aryl and aryloxy group, unless otherwise specified, is optionally substituted;

or a pharmaceutically acceptable derivative thereof;

provided that:

(a) when R$^4$ represents H or $C_{1-4}$ alkyl; and
A represents -J-N(R$^{24}$)— or -J-O—;
then B does not represent —N(R$^{25}$)—, —S(O)$_n$—, —O— or —N(R$^{25}$)-Z- (in which latter group —N(R$^{25}$) is attached to the carbon atom bearing R$^3$ and R$^4$);

(b) when $R^3$ represents $-E-OR^{18}$ or $-E-N(R^{19})R^{20}$ in which E represents a direct bond, then:
(i) A does not represent $-J-N(R^{24})-$ or $-J-O-$; and
(ii) B does not represent $-N(R^{25})-$, $-S(O)_n-$, $-O-$ or $-N(R^{25})-Z-$ (in which latter group $-N(R^{25})$ is attached to the carbon atom bearing $R^3$ and $R^4$);

for the manufacture of a medicament for the treatment or prophylaxis of cardiac arrhythmias.

Unless otherwise specified, alkyl groups and alkoxy groups as defined herein may be straight-chain or, when there is a sufficient number (i.e. a minimum of three) of carbon atoms, be branched-chain and/or cyclic. Further, when there is a sufficient number (i.e. a minimum of four) of carbon atoms, such alkyl and alkoxy groups may also be part cyclic/acyclic. Such alkyl and alkoxy groups may also be saturated or, when there is a sufficient number (i.e. a minimum of two) of carbon atoms, be unsaturated and/or interrupted by one or more oxygen and/or sulfur atoms. Unless otherwise specified, alkyl and alkoxy groups may also be substituted by one or more halo, and especially fluoro, atoms.

Unless otherwise specified, alkylene groups as defined herein may be straight-chain or, when there is a sufficient number (i.e. a minimum of two) of carbon atoms, be branched-chain. Such alkylene chains may also be saturated or, when there is a sufficient number (i.e. a minimum of two) of carbon atoms, be unsaturated and/or interrupted by one or more oxygen and/or sulfur atoms. Unless otherwise specified, alkylene groups may also be substituted by one or more halo atoms.

The term "aryl", when used herein, includes $C_{6-10}$ aryl groups such as phenyl, naphthyl and the like. The term "aryloxy", when used herein includes $C_{6-10}$ aryloxy groups such as phenoxy, naphthoxy and the like. For the avoidance of doubt, aryloxy groups referred to herein are attached to the rest of the molecule via the O-atom of the oxy-group. Unless otherwise specified, aryl and aryloxy groups may be substituted by one or more substituents including $-OH$, cyano, halo, nitro, $C_{1-6}$ alkyl (optionally terminated by $-N(H)C(O)OR^{26a}$), $C_{1-6}$ alkoxy, $Het^1$, aryl (which aryl group may not be substituted with any further aryl groups), $-N(R^{27a})R^{27b}$, $-C(O)R^{27c}$, $-C(O)OR^{27d}$, $-C(O)N(R^{27e})R^{27f}$, $-N(R^{27g})C(O)R^{27h}$, $-N(R^{27i})C(O)N(R^{27j})R^{27k}$, $-N(R^{27m})S(O)_2R^{26b}$, $-S(O)_nR^{26c}$, $-OS(O)_2R^{26d}$ and $-S(O)_2N(R^{27n})R^{21p}$ (wherein $Het^1$, $R^{26a}$, to $R^{26d}$, $R^{27a}$ to $R^{27p}$ and n are as hereinbefore defined). When substituted, aryl and aryloxy groups are preferably substituted by between one and three substituents.

The term "halo", when used herein, includes fluoro, chloro, bromo and iodo.

Het ($Het^1$ to $Het^{13}$) groups that may be mentioned include those containing 1 to 4 heteroatoms (selected from the group oxygen, nitrogen and/or sulfur) and in which the total number of atoms in the ring system are between five and twelve. Het ($Het^1$ to $Het^{13}$) groups may be fully saturated, wholly aromatic, partly aromatic and/or bicyclic in character. Heterocyclic groups that may be mentioned include benzodioxanyl, benzodioxepanyl, benzodioxolyl, benzofuranyl, benzofurazanyl, benzimidazolyl, benzomorpholinyl, benzothiophenyl, chromanyl, cinnolinyl, dioxanyl, furanyl, hydantoinyl, imidazolyl, imidazo[1,2-a]pyridinyl, indolyl, isoquinolinyl, isoxazolyl, maleimido, morpholinyl, oxazolyl, phthalazinyl, piperazinyl, piperidinyl, purinyl, pyranyl, pyrazinyl, pyrazolyl, pyridinyl, pyrimindinyl, pyrrolidinonyl, pyrrolidinyl, pyrrolinyl, pyrrolyl, quinazolinyl, quinolinyl, 3-sulfolenyl, tetrahydropyranyl, tetrahydrofuranyl, thiazolyl, thienyl, thiochromanyl, triazolyl and the like. Values of $Het^1$ that may be mentioned include maleimido, piperazinyl and thiazolyl. Values of $Het^2$ that may be mentioned include thiazolyl. Values of $Het^3$ that may be mentioned include hydantoinyl. Values of $Het^4$ that may be mentioned include benzodioxanyl, benzofurazanyl, indolyl, pyrazolyl and pyrrolyl. Values of $Het^5$ that may be mentioned include morpholinyl, piperazinyl and pyridinyl. Values of $Het^6$ that may be mentioned include isoxazolyl, pyridyl and tetrahydropyranyl. Values of $Het^7$ that may be mentioned include imidazolyl, pyrazolyl and thiazolyl.

When a Het ($Het^1$ to $Het^{13}$) group is substituted by one or more aryl and/or $Het^1$ group(s), that (those) said aryl and/or $Het^1$ substituent(s) may not itself (themselves) be substituted by any aryl and/or $Het^1$ group(s). Substituents on Het ($Het^1$ to $Het^{13}$) groups may, where appropriate, be located on any atom in the ring system including a heteroatom. The point of attachment of Het ($Het^1$ to $Het^{13}$) groups may be via any atom in the ring system including (where appropriate) a heteroatom, or an atom on any fused carbocyclic ring that may be present as part of the ring system. Het ($Het^1$ to $Het^{13}$) groups may also be in the N- or S-oxidised form.

Pharmaceutically acceptable derivatives include salts and solvates. Salts which may be mentioned include acid addition salts. Pharmaceutically acceptable derivatives also include, at the 3,8-diazabicyclo[3.2.1]octane or (when a Het ($Het^1$ to $Het^{13}$) group contains a tertiary nitrogen atom) tertiary heterocyclic nitrogens, $C_{1-4}$ alkyl quaternary ammonium salts and N-oxides, provided that when a N-oxide is present:
(a) no Het ($Het^1$ to $Het^{13}$) group contains an unoxidised S-atom; and/or
(b) n does not represent 0 when B represents $-Z-S(O)_n-$.

Compounds of formula I may exhibit tautomerism. All tautomeric forms and mixtures thereof are included within the scope of the invention.

Compounds of formula I may also contain one or more asymmetric carbon atoms and may therefore exhibit optical and/or diastereoisomerism.

Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation, or by derivatisation, for example with a homochiral acid followed by separation of the diastereomeric esters by conventional means (e.g. HPLC, chromatography over silica). All stereoisomers are included within the scope of the invention.

Abbreviations are listed at the end of this specification.

Some of the compounds of formula I are novel. According to a further aspect of the invention there is provided a compound of formula I as hereinbefore defined with the additional provisos that:
(A) when $R^a$ to $R^h$ all represent H, then $Het^2$ does not represent an optionally substituted 4-quinazoline;
(B) when $R^a$ to $R^h$ all represent H;
  $R^3$ represents H, halo, $C_{1-6}$ alkyl, or, together with $R^4$, represents =O;
  A represents -G- or -J-O— (in which latter group, O— is attached to the carbon atom bearing $R^3$ and $R^4$); and
  B represents -Z-;
  then $R^5$ does not represent optionally substituted phenyl;
(C) when B represents -Z-; and R⁵ represents 5-methyl-2-oxo-1,3-dioxol-4-yl, benzodioxolyl or optionally substituted phenyl;
then $R^{1a}$ does not represent 2-pyrimidinyl, 3-chloro-6-pyridazinyl, optionally substituted quinolinyl or optionally substituted naphthyridyl;
(D) when $R^a$ to $R^h$ all represent H;
$R^3$ represents H, $C_{1-6}$ alkyl or -E-N($R^{19}$)$R^{20}$;
A represents -G- or, when B represents -Z-, -J-N($R^{24}$)—; and
B represents -Z-N($R^{25}$)—, —N($R^{25}$)-Z- or, when A represents -J-N($R^{24}$)—, -Z-;
then $R^5$ does not represent phenyl optionally substituted by one or more substituents selected from halo, $C_{1-6}$ alkyl, $C_{1-6}$ alkoxy and —S$R^{26}$;
(E) when $R^a$ to $R^h$ all represent H;
$R^{1a}$ represents —C(O)$R^{7a}$;
$R^{7a}$ represents $C_{1-4}$ alkyl substituted (at the β-position relative to the carbonyl group) by 1,3-benzodioxolyl, 2,2-dimethyl-1,3-benzodioxolyl, 1,4-benzodioxanyl or an optionally substituted phenyl group;
$R^3$ and $R^4$ together represent =O; and
$R^5$ represents Het¹³;
then Het¹³ does not represent pyrrolidinyl, morpholinyl, hexamethyleneimino, 8-azabicyclo[3.2.1]octanyl or 2-pyrrolidinonyl; and
(F) the compound is not:
3-(3-methyl-3-phenoxybutyl)-8-propionyl-3,8-diazabicyclo[3.2.1]octane;
3-(3-methyl-3-phenxoycarbonyloxybutyl)-8-propionyl-3,8-diazabicyclo[3.2.1]octane;
3-(3-methyl-3-phenxoycarbonyloxybutyl)-8-methyl-3,8-diazabicyclo[3.2.1]octane;
8-propionyl-3-(2-pyridylethyl)-3,8-diazabicyclo[3.2.1]octane;
3-(3-cyclopentyl-3-hydroxy-3-phenylpropyl)-8-methyl-3,8-diazabicyclo[3.2.1]octane;
8-(3-cyclopentyl-3-hydroxy-3-phenylpropyl)-3-methyl-3,8-diazabicyclo[3.2.1]octane;
3-(3-cyclopentyl-4-hydroxy-3-phenylbutyl)-8-methyl-3,8-diazabicyclo[3.2.1]octane;
8-(3-cyclopentyl-4-hydroxy-3-phenylbutyl)-3-methyl-3,8-diazabicyclo[3.2.1]octane; or
8-methyl-3-(2-[N-phenylcarbamyloxy]ethyl)-3,8-diazabicyclo[3.2.1]octane.

According to a further aspect of the invention there is provided a compound of formula I as hereinbefore defined with the additional proviso that:
when $R^a$ to $R^h$ all represent H;
$R^3$ represents H, halo, $C_{1-6}$ alkyl, or, together with $R^4$, represents =O; and
A represents -G- or -J-O— (in which latter group, O— is attached to the carbon atom bearing $R^3$ and $R^4$);
then B does not represent -Z-.

Compounds of formula I that may be mentioned include those in which:
Het² represents a five-membered heterocyclic group containing one or more heteroatoms selected from oxygen, nitrogen and/or sulfur, which heterocyclic group is optionally substituted as defined above in respect of Het¹ to Het¹² groups;
$R^3$ and $R^4$ do not together represent =O;
B represents -Z-N($R^{25}$)—, —N($R^{25}$)-Z-, -Z-S(O)ₙ—, -Z-O— (in which latter two groups, Z is attached to the carbon atom bearing $R^3$ and $R^4$), or, when $R^3$ represents -E-O$R^{18}$ or -E-N($R^{19}$)$R^{20}$, B may alternatively represent -Z-;

$R^5$ represents aryl or Het¹³, both of which groups are substituted by one or more substituents as defined above in respect of $R^5$.

Compounds of formula I that may also be mentioned include those in which:
B represents -Z-N($R^{25}$)—, —N($R^{25}$)-Z-, -Z-S(O)ₙ—, -Z-O— (in which latter two groups, Z is attached to the carbon atom bearing $R^3$ and $R^4$), or, when $R^3$ represents —O$R^{18}$ (in which $R^{18}$ represents optionally substituted aryl), B may alternatively represent -Z-;
$R^5$ represents aryl or Het¹³, both of which groups are substituted by cyano and optionally by one or more further substituents as defined above in respect of $R^5$.

Preferred compounds of formula I include those in which:
$R^{1a}$ represents
  $C_{1-6}$ alkyl (which alkyl group is optionally part cyclic/acyclic or interrupted by oxygen and/or which alkyl group is optionally substituted and/or terminated by one or more groups selected from halo, cyano, optionally substituted phenyl, optionally substituted Het¹, —C(O)$R^{7a}$, —O$R^{7b}$, —C(O)O$R^9$, —C(O)N($R^{10}$)H and —S(O)₂—$C_{1-4}$ alkyl),
  optionally substituted Het²,
  —C(O)$R^{7a}$,
  —C(O)O$R^9$,
  —C(O)N($R^{10}$)H or
  —S(O)₂$R^{11}$;
$R^{7a}$ and $R^{7b}$ independently represent, at each occurrence when used herein, H, $C_{1-6}$ alkyl (optionally substituted and/or terminated by one or more substituents selected from $C_{1-6}$ alkoxy, halo, optionally substituted phenyl, optionally substituted Het³ and —NHC(O)$R^{12}$), optionally substituted phenyl or optionally substituted Het⁴;
$R^{12}$ represents $C_{1-3}$ alkyl (optionally substituted and/or terminated by one or more substituents selected from halo and —NHC(O)$R^{13}$);
$R^{13}$ represents $C_{1-3}$ alkyl;
$R^9$ represents, at each occurrence when used herein, optionally substituted phenyl or $C_{1-9}$ alkyl (which alkyl group is optionally unsaturated or cyclic and/or which alkyl group is optionally substituted and/or terminated by one or more substituents selected from —OH, halo, cyano, optionally substituted phenyl, $C_{1-6}$ alkoxy, —SO₂—$C_{1-4}$ alkyl and optionally substituted Het⁵);
$R^{10}$ represents, at each occurrence when used herein, $C_{1-9}$ alkyl (which alkyl group is optionally cyclic, part cyclic/acyclic, unsaturated or interrupted by oxygen and/or which alkyl group is optionally substituted and/or terminated by one or more substituents selected from halo and $C_{1-4}$ alkoxy), -D-(optionally substituted phenyl), -D-(optionally substituted Het⁶) or —S(O)₂$R^{17a}$;
$R^{17a}$ represents $C_{1-4}$ alkyl (optionally substituted and/or terminated by one or more substituents selected from halo and phenyl) or optionally substituted phenyl;
D represents a direct bond or $C_{1-4}$ alkylene;
$R^{11}$ represents, at each occurrence when used herein, $C_{1-5}$ alkyl (optionally substituted and/or terminated by one or more substituents selected from halo and phenyl), optionally substituted phenyl or optionally substituted Het⁷;
$R^3$ represents H, $C_{1-3}$ alkyl, —O$R^8$ or —N($R^{19}$)H;
$R^4$ represents H or $C_{1-3}$ alkyl;
$R^{18}$ represents H, optionally substituted phenyl, optionally substituted Het⁸, —C(O)$R^{21a}$ or —C(O)O$R^{21b}$;
$R^{19}$ represents H, optionally substituted phenyl, optionally substituted Het⁸, —C(O)$R^{21a}$, —C(O)O$R^{21b}$ or —[C(O)]ₚN($R^{22a}$)$R^{22b}$;

$R^{21a}$ and $R^{21b}$ independently represent, at each occurrence when used herein, $C_{1-4}$ alkyl (optionally substituted and/or terminated by one or more substituents selected from halo and phenyl);

$R^{22a}$ and $R^{22b}$ independently represent, at each occurrence when used herein, H or $C_{1-4}$ alkyl (optionally substituted and/or terminated by one or more substituents selected from halo and phenyl);

p represents 1 or 2;

A represents $C_{1-5}$ alkylene;

B represents -Z-, -Z-N($R^{25}$)—, -Z-S(O)$_2$—, -Z-O— (in which latter three groups, Z is attached to the carbon atom bearing $R^3$ and $R^4$);

Z represents a direct bond or $C_{1-3}$ alkylene;

$R^{25}$ represents H or $C_{1-4}$ alkyl;

$R^5$ represents phenyl optionally substituted by one or more substituents selected from —OH, cyano, halo, $C_{1-3}$ alkyl, $C_{1-3}$ alkoxy, —C(O)$R^{27c}$ and —N(H)C(O)N(H)$R^{27k}$;

Het$^1$ to Het$^8$ independently represent, at each occurrence when used herein, five- to ten-membered heterocyclic groups containing one to four heteroatoms selected from oxygen, nitrogen and/or sulfur, which heterocyclic groups are optionally substituted by one or more groups selected from =O, cyano, halo, $C_{1-5}$ alkyl, $C_{1-5}$ alkoxy, —N($R^{27a}$)$R^{27b}$, —C(O)$R^{27c}$, —N(H)C(O)$R^{27h}$ and —S(O)$_2R^{26c}$;

$R^a$ to $R^h$ all represent H;

optional substituents on phenyl groups are one or more groups selected from —OH, cyano, halo, nitro, $C_{1-5}$ alkyl, $C_{1-5}$ alkoxy, optionally substituted Het$^1$, —N($R^{27a}$)$^{27b}$, —C(O)$R^{27c}$, —N(H)C(O)$R^{27h}$ and —S$R^{26c}$;

$R^{26b}$ and $R^{26c}$ independently represent, at each occurrence when used herein, $C_{1-3}$ alkyl optionally substituted by halo;

$R^{27a}$ to $R^{27k}$ independently represent, at each occurrence when used herein, H or $C_{1-3}$ alkyl optionally substituted by halo.

More preferred compounds of formula I include those in which:

$R^{1a}$ represents $C_{1-5}$ alkyl (which alkyl group is optionally part cyclic/acyclic or interrupted by oxygen and/or which alkyl group is optionally substituted and/or terminated by one or more groups selected from cyano, optionally substituted phenyl, optionally substituted Het$^1$, —C(O)$R^{7a}$, —OR$^{7b}$ and —S(O)$_2$—$C_{1-3}$ alkyl), optionally substituted Het$^2$, —C(O)$R^{7a}$,

—C(O)OR$^9$,

—C(O)N(R$^{10}$)H or

—S(O)$_2R^{11}$;

$R^{7a}$ and $R^{7b}$ independently represent, at each occurrence when used herein, H, $C_{1-5}$ alkyl (optionally substituted and/or terminated by one or more substituents selected from $C_{1-4}$ alkoxy, optionally substituted Het$^3$ and —NHC(O)$R^{12}$), optionally substituted phenyl or optionally substituted Het$^4$;

$R^{12}$ represents $C_{1-2}$ alkyl (optionally substituted and/or terminated by —NHC(O)—$C_{1-2}$ alkyl);

$R^9$ represents, at each occurrence when used herein, optionally substituted phenyl or $C_{1-7}$ alkyl (which alkyl group is optionally unsaturated or cyclic and/or which alkyl group is optionally substituted and/or terminated by one or more substituents selected from —OH, cyano, phenyl, $C_{1-3}$ alkoxy, —SO$_2$—$C_{1-3}$ alkyl and optionally substituted Het$^5$);

$R^{10}$ represents, at each occurrence when used herein, $C_{1-7}$ alkyl (which alkyl group is optionally cyclic, part cyclic/acyclic, unsaturated or interrupted by oxygen and/or which alkyl group is optionally substituted and/or terminated by $C_{1-3}$ alkoxy), optionally substituted phenyl, optionally substituted Het$^6$ or —S(O)$_2R^{17a}$;

$R^{17a}$ represents optionally substituted phenyl;

$R^{11}$ represents, at each occurrence when used herein, $C_{1-5}$ alkyl, optionally substituted phenyl or optionally substituted Het$^7$;

$R^3$ represents H, —OR$^{18}$ or —N(R$^{19}$)H;

$R^4$ represents H;

$R^{18}$ is represents H, optionally substituted phenyl or —C(O)$R^{21a}$;

$R^{19}$ represents H, —C(O)$R^{21a}$ or —C(O)OR$^{21b}$;

$R^{21a}$ and $R^{21b}$ independently represent, at each occurrence when used herein, $C_{1-3}$ alkyl;

A represents $C_{1-4}$ alkylene;

B represents -Z-, -Z-N(H)—, -Z-S(O)$_2$—, -Z-O— (in which latter three groups, Z is attached to the carbon atom bearing $R^3$ and $R^4$);

Z represents a direct bond or $C_{1-2}$ alkylene;

$R^5$ represents phenyl optionally substituted by one or more substituents selected from —OH, cyano, halo and $C_{1-3}$ alkoxy.

Compounds of formula I that are more preferred still include those in which:

$R^3$ represents H, —OR$^{18}$ or —N(R$^{19}$)H;

$R^4$ represents H;

$R^{18}$ represents H or phenyl (which latter group is substituted either by a hydroxy group or by two methoxy groups);

$R^{19}$ represents H or —C(O)OCH$_3$;

A represents $C_{1-3}$ alkylene;

B represents -Z-N(H)—, -Z-S(O)$_2$—, -Z-O— (in which latter three groups, Z is attached to the carbon atom bearing $R^3$ and $R^4$) or, when $R^3$ represents —OR$^{18}$, B may alternatively represent a direct bond;

Z represents a direct bond or $C_{1-2}$ alkylene;

$R^5$ represents phenyl substituted in the 4-position (relative to the group B) by cyano, and optionally substituted in the 2-position (relative to the group B) by a further cyano group.

When $R^{1a}$ represents $C_{1-12}$ alkyl (optionally substituted as defined above in respect of $R^{1a}$), —C(O)XR$^9$ or —C(O)N(R$^{10}$)R$^{7d}$, preferred compounds of formula I include those in which:

$R^3$ represents H, —OR$^{18}$ or —N(R$^{19}$)H;

$R^4$ represents H;

$R^{18}$ represents H or phenyl (which latter group is substituted either by a hydroxy group or by from one to three $C_{1-2}$ alkoxy groups);

$R^{19}$ represents H or —C(O)O—(C$_{1-2}$ alkyl);

A represents $C_{1-3}$ alkylene;

B represents -Z-N(H)—, -Z-S(O)$_2$—, -Z-O— (in which latter three groups, Z is attached to the carbon atom bearing $R^3$ and $R^4$) or, when $R^3$ represents —OR$^{18}$, B may alternatively represent a direct bond;

Z represents a direct bond or $C_{1-2}$ alkylene;

$R^5$ represents phenyl substituted by one or two cyano groups.

When $R^{1a}$ represents —C(O)$R^{7a}$, preferred compounds of formula I include those in which:

$R^3$ represents H, OR$^{18}$ or —N(H)—C(O)O—(C$_{1-2}$ alkyl);

$R^4$ represents H;

$R^{18}$ represents H or phenyl (which latter group is substituted either by a hydroxy group or by from one to three $C_{1-2}$ alkoxy groups);

A represents $C_{1-3}$ alkylene;

B represents -Z-N(H)—, -Z-S(O)$_2$—, -Z-O— (in which latter three groups, Z is attached to the carbon atom bearing R$^3$ and R$^4$) or, when R$^3$ represents —OR$^{18}$, B may alternatively represent a direct bond;
Z represents a direct bond or CH$_2$;
R$^5$ represents phenyl substituted by one or two cyano groups.

When R$^{1a}$ represents —SO$_2$R$^{11}$, preferred compounds of formula I include those in which:
R$^3$ represents H, —OR$^{18}$ or —N(H)—C(O)O—(C$_{1-2}$ alkyl);
R$^4$ represents H;
R$^{18}$ represents H or phenyl (which latter group is substituted by from one to three C$_{1-2}$ alkoxy groups);
A represents C$_{1-3}$ alkylene;
B represents -Z-N(H)—, -Z-S(O)$_2$—, -Z-O— (in which latter three groups, Z is attached to the carbon atom bearing R$^3$ and R$^4$) or, when R$^3$ represents —OR$^{18}$, B may alternatively represent a direct bond;
Z represents a direct bond or CH$_2$;
R$^5$ represents phenyl substituted by one or two cyano groups.

When R$^{1a}$ represents unsubstituted C$_{1-12}$ alkyl, preferred compounds of formula I include those in which:
R$^3$ represents H, —OR$^{18}$ or —N(R$^{19}$)H;
R$^4$ represents H;
R$^{18}$ represents phenyl (which latter group is substituted either by a hydroxy group or by from one to three C$_{1-2}$ alkoxy groups);
R$^{19}$ represents H or —C(O)O—(C$_{1-2}$ alkyl);
A represents C$_{1-3}$ alkylene;
B represents -Z-N(H)—, -Z-S(O)$_2$—, -Z-O— (in which latter three groups, Z is attached to the carbon atom bearing R$^3$ and R$^4$) or, when R$^3$ represents —OR$^{18}$, B may alternatively represent a direct bond;
Z represents a direct bond or C$_{1-2}$ alkylene;
R$^5$ represents phenyl substituted by one or two cyano groups.

When R$^{1a}$ represents Het$^2$, preferred compounds of formula I include those in which:
R$^3$ represents H, —OH;
R$^4$ represents H;
A represents CH$_2$;
B represents —CH$_2$—N(H)— or —CH$_2$—O— (in which two groups, CH$_2$ is attached to the carbon atom bearing R$^3$ and R$^4$);
R$^5$ represents phenyl substituted by cyano.

Preferred compounds of formula I include the compounds of the Examples disclosed hereinafter.

Preparation

According to the invention there is also provided a process for the preparation of compounds of formula I which comprises:
(a) reaction of a compound of formula IIA or IIB,

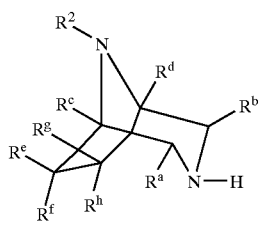

IIA

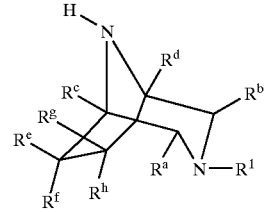

IIB wherein R$^1$, R$^2$ and R$^a$ to R$^h$ are as hereinbefore defined, with a compound of formula III, $$R^{28}\text{-}L^1$$ III wherein R$^{28}$ represents either R$^1$ or R$^2$ (as appropriate), L$^1$ represents a leaving group such as halo, alkanesulfonate, perfluoroalkanesulfonate, arenesulfonate, —OC(O)XR$^9$, imidazole or R$^{29}$O— (wherein R$^{29}$ represents, for example, C$_{1-10}$ alkyl or aryl, which groups are optionally substituted by one or more halo or nitro groups) and R$^1$, R$^2$ and R$^9$ are as hereinbefore defined, for example at between −10° C. and reflux temperature in the presence of a suitable base (e.g. triethylamine or potassium carbonate) and an appropriate organic solvent (e.g. dichloromethane, chloroform, acetonitrile, N,N-dimethylformamide, dimethylsulfoxide, THF, toluene or mixtures thereof);

(b) for compounds of formula I in which R$^1$ or R$^2$ (as appropriate) represents —C(O)XR$^9$ or —C(O)N(R$^{10}$)R$^{7d}$, reaction of a compound of formula IVA or IVB,

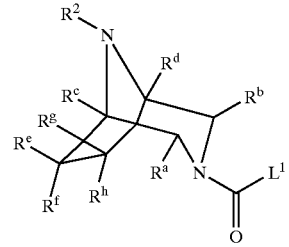

IVA

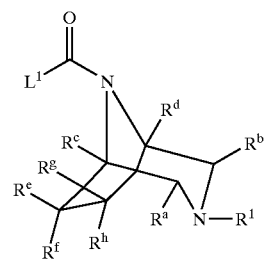

IVB wherein R$^a$ to R$^h$ and L$^1$ are as hereinbefore defined R$^1$ or R$^2$ (as appropriate) represents a fragment of formula Ia, as hereinbefore with a compound of formula V, $$R^{30}\text{—}H$$ V wherein R$^{30}$ represents —XR$^9$ or —N(R$^{10}$)R$^{7d}$, and R$^9$, R$^{10}$ and X are as hereinbefore defined, for example under conditions described hereinbefore (process step (a));

(c) for compounds of formula I in which R$^1$ or R$^2$ (as appropriate) represents —C(O)N(H)R$^{10}$, reaction of a compound of formula IIA or IIB (as appropriate), in which $R^1$ or $R^2$ (as appropriate) represents a fragment of formula Ia, with a compound of formula VI, $$R^{10}-N=C=O \qquad \text{VI}$$

wherein $R^{10}$ is as hereinbefore defined, for example at between 0° C. and reflux temperature in the presence of an appropriate organic solvent (e.g. dichloromethane), or via solid phase synthesis under conditions known to those skilled in the art;

(d) for compounds of formula I in which $R^1$ or $R^2$ (as appropriate) represents a fragment of formula Ia in which A represents $CH_2$ and $R^3$ represents —OH or —N(H)$R^{19}$, reaction of a compound of formula IIA or IIB, as hereinbefore defined (except that $R^1$ or $R^2$ (as appropriate) does not represent a fragment of formula Ia), with a compound of formula VII,

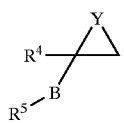

VII wherein Y represents O or N($R^{19}$) and $R^4$, $R^5$, $R^{19}$ and B are as hereinbefore defined, for example at elevated temperature (e.g. 60° C. to reflux) in the presence of a suitable solvent (e.g. a lower alkyl alcohol (e.g. IPA), acetonitrile, or a mixture of a lower alkyl alcohol and water);

(e) for compounds of formula I in which, in the fragment of formula Ia, B represents -Z-O—, reaction of a compound of formula VIIIA or VIIIB,

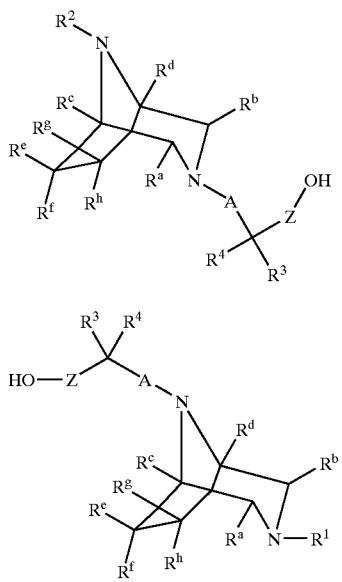

VIIIA

VIIIB wherein $R^3$, $R^4$, $R^a$ to $R^h$, A and Z are as hereinbefore defined, and $R^1$ and $R^2$ (as appropriate) are as hereinbefore defined (except that, in each case, they do not represent a fragment of formula Ia), with a compound of formula IX, $$R^5\text{—OH} \qquad \text{IX}$$

wherein $R^5$ is as hereinbefore defined, for example under Mitsunobu-type conditions e.g. at between ambient (e.g. 25° C.) and reflux temperature in the presence of a tertiary phosphine (e.g. tributylphosphine or triphenylphosphine), an azodicarboxylate derivative (e.g. diethylazodicarboxylate or 1,1'-(azodicarbonyl)dipiperidine) and an appropriate organic solvent (e.g. dichloromethane or toluene);

(f) for compounds of formula I in which B represents -Z-O—, reaction of a compound of formula VIIIA or VIIIB, as hereinbefore defined, with a compound of formula X, $$R^5\text{-}L^2 \qquad \text{X}$$

wherein $L^2$ represents a leaving group such as halo, alkanesulfonate, perfluoroalkanesulfonate or arenesulfonate, and $R^5$ is as hereinbefore defined, for example under conditions known to those skilled in the art (e.g. when $R^5$ represents 2- or 4-pyridyl, reaction at between 10° C. and reflux temperature in the presence of a suitable base (such as sodium hydride) and an appropriate solvent (such as N,N-dimethylformamide));

(g) for compounds of formula I in which $R^3$ represents -E-O$R^{18}$, in which $R^{18}$ represents $C_{1-6}$ alkyl, -E-aryl or -E-$Het^8$, reaction of a corresponding compound of formula I in which $R^3$ represents -E-OH with a compound of formula XI, $$R^{18a}OH \qquad \text{XI}$$

wherein $R^{18a}$ represents $C_{1-6}$ alkyl, -E-aryl or -E-$Het^8$, and E and $Het^8$ are as hereinbefore defined, for example under Mitsunobu-type conditions (e.g. as described hereinbefore in process step (e));

(h) for compounds of formula I in which $R^3$ represents —O$R^{18}$, in which $R^{18}$ represents $C_{1-6}$-alkyl, -E-aryl or -E-$Het^8$, reaction of a compound of formula XIIA or XIIB,

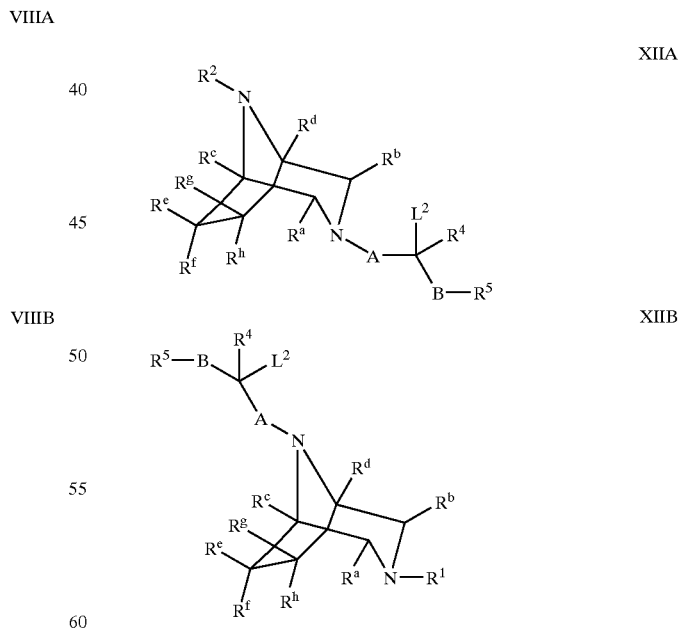

XIIA

XIIB wherein $R^1$ or $R^2$ (as appropriate) represents $R^{1a}$, and $R^{1a}$, $R^4$, $R^5$, $R^a$ to $R^h$, A, B and $L^2$ are as hereinbefore defined, with a compound of formula XI, as hereinbefore defined, for example at between ambient (e.g. 25° C.) and reflux temperature, under Williamson-type conditions (i.e. in the presence of an appropriate base (e.g. KOH or NaH) and a suitable organic solvent (e.g. dimethylsulfoxide or N,N-dimethylformamide)) (the skilled person will appreciate that certain compounds of formula XIIA and XIIB (e.g. those in which $L^2$ represents halo) may also be regarded as compounds of formula I as hereinbefore defined);

(i) for compounds of formula I in which $R^3$ represents -E-NH$_2$, reduction of a compound of formula XIIIA or XIIIB,

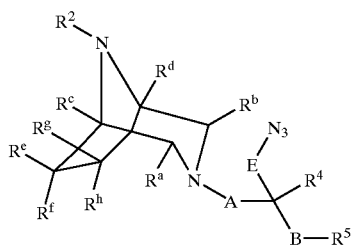

XIIIA

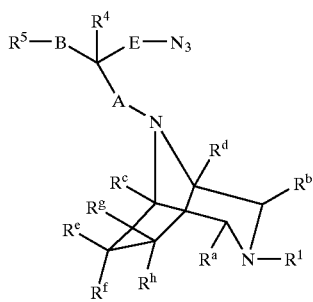

XIIIB wherein $R^1$ or $R^2$ (as appropriate) represents $R^{1a}$, and $R^{1a}$, $R^4$, $R^5$, $R^a$ to $R^h$, A, B and E are as hereinbefore defined, for example by hydrogenation at a suitable pressure in the presence of a suitable catalyst (e.g. palladium on carbon) and an appropriate solvent (e.g. a water-ethanol mixture);

(j) for compounds of formula I in which $R^3$ represents -E-N($R^{19}$)$R^{20}$, wherein $R^{19}$ represents $C_{1-6}$ alkyl, -E-aryl-E-Het$^8$, —C(O)$R^{21a}$, —C(O)O$R^{21b}$, —S(O)$_2R^{21c}$ or —C(O)N($R^{22a}$)$R^{22b}$, reaction of a corresponding compound of formula I in which $R^3$ represents -E-N(H)$R^{20}$ with a compound of formula XIV, $R^{19a}$-L$^1$  XIV wherein $R^{19a}$ represents $C_{1-6}$ alkyl, -E-aryl -E-Het$^8$, —C(O)$R^{21a}$, —C(O)O$R^{21b}$, —S(O)$_2R^{21c}$ or —C(O)N($R^{22a}$)$R^{22b}$, and $R^{21a}$, $R^{21b}$, $R^{21c}$, $R^{22a}$ $R^{22b}$, Het$^8$, E and L$^1$ are as hereinbefore defined, for example under conditions described hereinbefore (process step (a));

(k) for compounds of formula I in which $R^3$ represents -E-N($R^{20}$)C(O)N(R)$R^{22a}$, reaction of a corresponding compound of formula I in which $R^3$ represents -E-N(R)$R^{20}$ with a compound of formula XV, $R^{22a}$—N=C=O 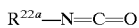 XV wherein $R^{22a}$ is as hereinbefore defined, for example under conditions described hereinbefore (process step (c));

(l) for compounds of formula I in which $R^3$ represents -E-N(H)[C(O)]$_2$NH$_2$, reaction of a corresponding compound of formula I in which $R^3$ represents -E-NH$_2$ with oxalic acid diamide, for example at between −10 and 25° C. in the presence of a suitable coupling agent (e.g. 1-(3-dimethylaminopropyl)-3-ethylcarbodiimide), an appropriate activating agent (e.g. 1-hydroxybenzotriaz-ole), a suitable base (e.g. triethylamine) and a reaction-inert solvent (e.g. N,N-dimethylformamide);

(m) for compounds of formula I in which $R^3$ represents -E-N(H)C(NH)NH$_2$, reaction of a corresponding compound of formula I in which $R^3$ represents -E-NH$_2$ with a compound of formula XVI, $R^{29}$O—C(=NH)NH$_2$ 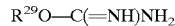 XVI or an N-protected derivative thereof, wherein $R^{29}$ is as hereinbefore defined, for example at between room and reflux temperature, optionally in the presence of a suitable solvent (e.g. toluene) and/or an appropriate acidic catalyst (e.g. acetic acid at, for example, 10 mol %);

(n) for compounds of formula I in which $R^3$ represents -E-O$R^{18}$, in which $R^{18}$ represents —C(O)$R^{21a}$, —C(O)O$R^{21b}$ or —C(O)N($R^{22a}$)$R^{22b}$, reaction of a corresponding compound of formula I in which $R^3$ represents -E-OH with a compound of formula XVII, $R^{18b}$-L$^3$  XVII wherein $R^{18b}$ represents —C(O)$R^{21a}$, —C(O)O$R^{21b}$ or —C(O)N($R^{22a}$)$R^{22b}$, L$^3$ represents a leaving group such as halo, p-nitrophenoxy, —OC(O)$R^{21a}$, —OC(O)O$R^{21b}$, —OH or imidazole and $R^{21a}$, $R^{22b}$, $R^{22a}$ and $R^{22b}$ are as hereinbefore defined, for example at between −10° C. and reflux temperature in the presence of a suitable base (e.g. triethylamine, pyridine or potassium carbonate), an appropriate organic solvent (e.g. THF, dichloromethane or acetonitrile) and (where appropriate) a suitable coupling agent (e.g. 1-(3-dimethylaminopropyl)-3-ethylcarbodiimide);

(o) for compounds of formula f in which A represents $C_{1-6}$ alkylene, B represents $C_{1-4}$ alkylene and $R^3$ and $R^4$ both represent H, reduction of a corresponding compound of formula I in which $R^3$ and $R^4$ together represent =O, in the presence of a suitable reducing agent and under appropriate reaction conditions, for example by activating the relevant C=O group using an appropriate agent (such as tosylhydrazine) in the presence of a suitable reducing agent (e.g. sodium borohydride or sodium cyanoborohydride) and an appropriate organic solvent (e.g. a lower (e.g. $C_{1-6}$) alkyl alcohol);

(p) for compounds of formula I in which $R^3$ and $R^4$ both represent H and (1) A represents -J-N($R^{24}$) and B represents $C_{1-4}$ alkylene, or (2) A represents $C_{1-6}$ alkylene and B represents N($R^{25}$) or —N($R^{25}$)-Z- (in which latter group —N($R^{25}$) is attached to the carbon atom bearing $R^3$ and $R^4$), reduction of a corresponding compound of formula I in which $R^3$ and $R^4$ together represent =O, in the presence of a suitable reducing agent (e.g. LiAlH$_4$) and an appropriate solvent (e.g. THF);

(q) for compounds of formula I in which A represents $C_{1-6}$ alkylene, B represents a direct bond, $C_{1-4}$ alkylene, -Z-N($R^{25}$)—, -Z-S(O)$_p$— or -Z-O— (in which latter three groups Z represents $C_{1-4}$ alkylene attached to the carbon atom bearing $R^3$ and $R^4$), $R^3$ represents OH and $R^4$ represents H, reduction of a corresponding compound of formula I in which $R^3$ and $R^4$ together represent =O, in the presence of a suitable reducing agent (e.g. NaBH$_4$) and an appropriate organic solvent (e.g. THF);

(r) for compounds of formula I in which $R^3$ represents halo, substitution of a corresponding compound of formula I in which $R^3$ represents —OH, using an appropriate halogenating agent (e.g. for compounds in which $R^3$ represents fluoro, reaction with (diethylamino)sulfur trifluoride);

(s) for compounds of formula I in which $R^3$ and $R^4$ represent H or $C_{1-6}$alkyl, A represents $C_{1-6}$ alkylene and B represents —N(R$^{25}$)-Z- (wherein —N(R$^{25}$) is attached to the carbon atom bearing R$^3$ and R$^4$), reaction of a compound of formula XVIIIA or XVIIIB,

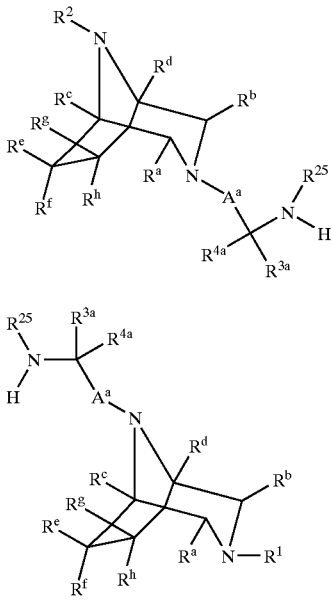

XVIIIA

XVIIIB wherein R$^1$ or R$^2$ (as appropriate) represents R$^{1a}$, R$^{3a}$ and R$^{4a}$ represent H or C$_{1-6}$ alkyl, A$^a$ represents C$_{1-6}$ alkylene and R$^{1a}$, R$^{25}$ and R$^a$ to R$^h$ are as hereinbefore defined, with a compound of formula XIX,

R$^5$-Z-L$^2$  XIX wherein R$^5$, Z and L$^2$ are as hereinbefore defined, for example at elevated temperature (e.g. 40° C. to reflux) in the presence of a suitable organic solvent (e.g. acetonitrile);

(t) for compounds of formula I in which A represents C$_2$ alkylene and R$^3$ and R$^4$ together represent =O, reaction of a compound of formula IIA or IIB, as hereinbefore defined (except that R$^1$ or R$^2$ (as appropriate) does not represent a fragment of formula Ia), with a compound of formula XX,

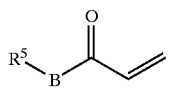

XX wherein B and R$^5$ are as hereinbefore defined, for example at between room and reflux temperature in the presence of a suitable base (e.g. triethylamine, potassium carbonate or tetrabutylammonium hydroxide) and an appropriate organic solvent (e.g. a lower alkyl (e.g. C$_{1-6}$) alcohol);

(u) for compounds of formula I in which R$^1$ represents —C(O)OR$^9$ and R$^a$ and/or R$^b$ represent C$_{1-4}$ alkyl, reaction of a corresponding compound of formula I in which R$^1$ represents —C(O)OR$^9$ and R$^a$ and R$^b$ represent H with one or more equivalents of a compound of formula XXI,

R$^{32}$-L$^4$  XXI wherein R$^{32}$ represents C$_{1-4}$ alkyl and L$^4$ is a leaving group such as halo, alkylsulfate, alkanesulfonate or arenesulfonate, in the presence of an appropriate strong base (e.g. butyllithium), for example at between –80° C. and room temperature in the presence of a suitable solvent (e.g. N,N,N',N'-tetramethylethylenediamine, THF or mixtures thereof).

(v) for compounds of formula I which are 3,8-diazabicyclo[3.2.1]octane-nitrogen N-oxide derivatives, oxidation of the corresponding 3,8-diazabicyclo[3.2.1]octane nitrogen of a corresponding compound of formula I, in the presence of a suitable oxidising agent (e.g. , mCPBA), for example at 0° C. in the presence of a suitable organic solvent (e.g. dichloromethane);

(w) for compounds of formula I which are C$_{1-4}$ alkyl quaternary ammonium salt derivatives, in which the alkyl group is attached to a 3,8-diazabicyclo[3.2.1]octane nitrogen, reaction, at the 3,8-diazabicyclo[3.2.1]octane nitrogen, of a corresponding compound of formula I with a compound of formula XXI, as hereinbefore defined, for example at room temperature in the presence of an appropriate organic solvent (e.g. N,N-dimethylformamide), followed by purification (using e.g. HPLC) in the presence of a suitable counter-ion provider (e.g. NH$_4$OAc); or (x) conversion of one substituent on R$^5$ to another using techniques well known to those skilled in the art.

Compounds of formula IIA or IIB may be prepared by reaction of a compound of formula XXII,

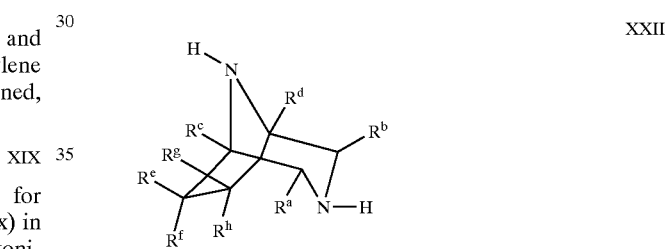

XXII or an N-protected derivative thereof, wherein R$^a$ to R$^h$ are as hereinbefore defined, with a compound of formula III as hereinbefore defined, for example as described hereinbefore for the synthesis of compounds of formula I (process step (a)), or, in the case of compounds of formula IIA or IIB wherein R$^1$ or R$^2$ (as appropriate) represents a fragment of formula Ia in which A represents CH$_2$ and R$^3$ represents —OH or N(H)R$^{19}$, wherein R$^{19}$ is as hereinbefore defined, with a compound of formula VII as hereinbefore defined, for example as described hereinbefore for the synthesis of compounds of formula I (process step (d)).

Compounds of formula III may be prepared by standard techniques. For example, compounds of formula III in which R$^{28}$ represents a fragment of formula Ia, wherein:

(1) B represents -Z-O— may be prepared by coupling a compound of formula IX, as hereinbefore defined, to a compound of formula XXIII,

L$^1$-Z-C(R$^3$)(R$^4$)-A-L$^1$  XXIII wherein R$^3$, R$^4$, A, Z and L$^1$ are as hereinbefore defined, and the two L$^1$ groups may be the same or different; or (2) B represents —N(R$^{25}$)-Z- (wherein N(R$^{25}$) is attached to the carbon atom bearing R$^3$ and R$^4$) and R$^3$ and R$^4$ together represent =O may be prepared by coupling a compound of formula XXIV

R$^5$-Z-N(H)R$^{25}$  XXIV wherein $R^5$, $R^{25}$ and Z are as hereinbefore defined, to a compound of formula XXV,

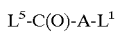     XXV wherein $L^5$ represents a suitable leaving group (e.g. —OH or halo) and A and $L^1$ are as hereinbefore defined;

in both cases, under conditions which are well known to those skilled in the art.

Compounds of formula III in which $R^{28}$ represents a fragment of formula Ia, wherein A represents $C_2$ alkylene and $R^3$ represents —$OR^{18}$, in which $R^{18}$ represents $C_{1-6}$ alkyl, -E-aryl or -E-$Het^8$ may alternatively be prepared by reaction of a compound of formula XI, as hereinbefore defined, with a compound of formula XXVI,

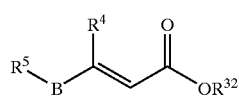     XXVI wherein $R^4$, $R^5$, $R^{32}$ and B are as hereinbefore defined, for example at between ambient temperature (e.g. 25° C.) and reflux temperature in the presence of a suitable base (e.g. potassium carbonate) and an appropriate organic solvent (e.g. acetonitrile), followed by conversion of the ester functionality to an $L^1$ group (in which $L^1$ is as hereinbefore defined), under conditions that are well known to those skilled in the art.

Compounds of formula III in which A represents $C_{2-6}$ alkylene may be prepared by reduction of a corresponding compound of formula XXVII,

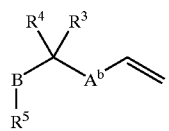     XXVII wherein $A^b$ represents a direct bond or $C_{1-4}$ alkylene, and $R^3$, $R^4$, $R^5$ and B are as hereinbefore defined, with a suitable borane or borane-Lewis base complex (e.g. borane-dimethyl sulfide) in the presence of an appropriate solvent (e.g. diethyl ether, THF, or a mixture thereof), followed by oxidation of the resulting borane adduct with a suitable oxidising agent (e.g. sodium perborate) and then conversion of the resulting OH group to an $L^1$ group under conditions known to those skilled in the art.

Compounds of formula III in which A represents $C_{1-6}$ alkylene and B represents -Z-$N(R^{25})$— (in which latter case Z is attached to the carbon atom bearing $R^3$ and $R^4$) may be prepared by coupling a compound of formula X, with a compound of formula XXVIII, $HN(R^{25})$-Z-$C(R^3)(R^4)$-$A^a$-OH     XXVIII wherein $A^a$, Z, $R^3$, $R^4$ and $R^{25}$ are as hereinbefore defined, for example at between room and reflux temperature, optionally in the presence of a suitable solvent and/or an appropriate base, followed by conversion of the OH group to an $L^1$ group under conditions known to those skilled in the art.

Compounds of formula III in which B represents -Z-S (O)— or -Z-$S(O)_2$— may be prepared by oxidation of corresponding compounds of formula III in which B represents -Z-S—, wherein Z is as hereinbefore defined, in the presence of an appropriate amount of a suitable oxidising agent (e.g. mCPBA) and an appropriate organic solvent.

Compounds of formula IVA and IVB may be prepared by reaction of a compound of formula IIA or IIB, respectively, as hereinbefore defined, with a compound of formula XXIX,

     XXIX wherein $L^1$ is as hereinbefore defined, and in which the two $L^1$ groups may be the same or different, for example at between 0° C. and reflux temperature in the presence of a suitable base (e.g. triethylamine or potassium carbonate) and an appropriate organic solvent (e.g. toluene or dichloromethane).

Compounds of formula VII may be prepared in accordance with techniques that are known to those skilled in the art. For example, compounds of formula VII in which:

(1) B represents —$CH_2O$— and Y represents O may be prepared by reaction of a compound of formula IX, as hereinbefore defined, with a compound of formula XXX

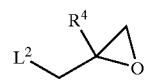     XXX wherein $R^4$ and $L^2$ are as hereinbefore defined, for example at elevated temperature (e.g. between 60° C. and reflux temperature) in the presence of a suitable base (e.g. potassium carbonate or NaOH) and an appropriate organic solvent (e.g. acetonitrile or toluene/water), or as otherwise described in the prior art;

(2) $R^4$ represents H, B represents a direct bond, $C_{1-4}$ alkylene, -Z-$N(R^{25})$—, -Z-$S(O)_n$— or -Z-O— (in which, in each case, the group Z represents $C_{1-4}$ alkylene attached to the carbon atom bearing $R^4$) and Y represents O may be prepared by reduction of a compound of formula XXXIA or XXXIB,

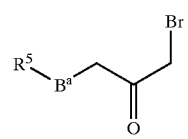     XXXIA

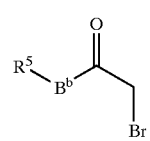     XXXIB wherein $B^a$ represents -$Z^b$-$N(R^{25})$, -$Z^b$-$S(O)_n$— or -$Z^b$-O— (in which, in each case, the group $Z^b$ represents a direct bond or $C_{1-3}$ alkylene attached (via the methylene group) to the carbon atom bearing $R^4$), $B^b$ represents a direct bond or $C_{1-4}$ alkylene, and $R^5$, $R^{25}$ and n are as hereinbefore defined, for example at between –15° C. and room temperature in the presence of a suitable reducing agent (e.g. $NaBH_4$) and an appropriate organic solvent (e.g. THF), followed by an internal displacement reaction in the resultant intermediate, for example at room temperature in the presence of a suitable base (e.g. potassium carbonate) and an appropriate organic solvent (e.g. acetonitrile);

(3) B represents a direct bond, $C_{1-4}$ alkylene, -Z-N($R^{25}$)—, -Z-S(O)$_2$— or -Z-O— (in which, in each case, the group Z represents $C_{1-4}$ alkylene attached to the carbon atom bearing $R^4$) and Y represents O may be prepared by oxidation of a compound of formula XXXIIA or XXXIIB,

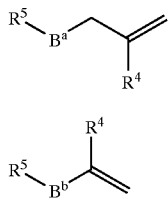

XXXIIA

XXXIIB wherein $R^4$, $R^5$, $B^a$ and $B^b$ are as hereinbefore defined, in the presence of a suitable oxidising agent (e.g. mCPBA), for example by refluxing in the presence of a suitable organic solvent (e.g. dichloromethane); or (4) B represents -Z-O—, in which group Z represents $C_{1-4}$ alkylene attached to the carbon atom bearing $R^4$, and Y represents —N($R^{19}$), wherein $R^{19}$ represents —C(O)O$R^{21b}$ or —S(O)$_2R^{21c}$, may be prepared by cyclisation of a compound of formula XXXIII,

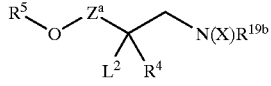

XXXIII wherein $R^{19b}$ represents —C(O)O$R^{21b}$ or —S(O)$_2R^{21c}$, $Z^a$ represents $C_{1-4}$ alkylene and $R^4$, $R^5$, $R^{21b}$, $R^{21c}$ and $L^2$ are as hereinbefore defined, for example at between 0° C. and reflux temperature in the presence of a suitable base (e.g. sodium hydroxide), an appropriate solvent (e.g. dichloromethane, water, or a mixture thereof) and, if necessary, a phase transfer catalyst (such as tetrabutylammonium hydrogensulfate).

Compounds of formula VIIIA, VIIIB, XIIA, XIIB, XIIIA, XIIIB, XVIIIA and XVIIIB may be prepared in a similar fashion to compounds of formula I (see, for example process steps (a) to (d)).

Compounds of formula XIIA and XIIB may alternatively be prepared by replacement of the —OH group of a corresponding compound of formula I in which $R^3$ represents —OH with an $L^2$ group under conditions that are known to those skilled in the art.

Compounds of formula XIIIA and XIIIB may alternatively be prepared by reaction of corresponding compounds of formula I in which $R^3$ represents -E-OH with a compound of formula XXXIV,

XXXIV wherein $R^{33}$ represents $C_{1-4}$ alkyl or aryl (which two groups are optionally substituted by one or more substituents selected from $C_{1-4}$ alkyl, halo and nitro), for example at between −10 and 25° C. in the presence of a suitable solvent (e.g. dichloromethane), followed by reaction with a suitable source of the azide ion (e.g. sodium azide), for example at between ambient and reflux temperature in the presence of an appropriate solvent (e.g. N,N-dimethylformamide) and a suitable base (e.g. sodium hydrogencarbonate).

Compounds of formula XIIIA and XIIIB may also be prepared by reaction of a compound of formula IIA or IIB, as hereinbefore defined (except that $R^1$ or $R^2$ (as appropriate) does not represent a fragment of formula Ia), with a compound of formula XXXV,

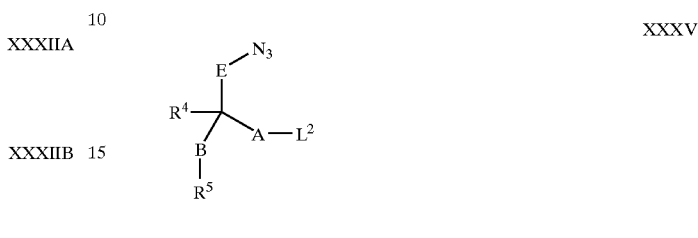

XXXV wherein $R^4$, $R^5$, A, B, E and $L^2$ are as hereinbefore defined, for example under analogous conditions to those described hereinbefore for the synthesis of compounds of formula I (process step (a)).

Compounds of formula XXII may be prepared by reaction of a corresponding compound of formula XXXVI,

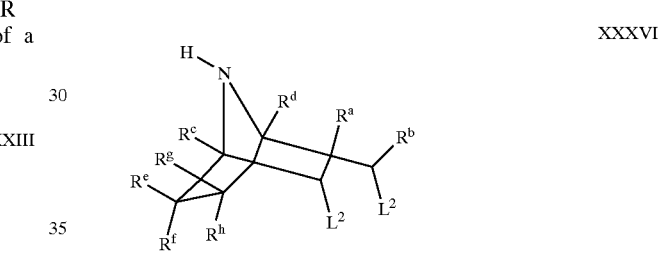

XXXVI or an N-protected (e.g. N-benzyl) derivative thereof, wherein $R^a$ to $R^h$ and $L^2$ are as hereinbefore defined, with ammonia or a protected derivative thereof (e.g. allylamine), for example at between room and reflux temperature in the presence of a suitable base (e.g. sodium bicarbonate) and an appropriate organic solvent (e.g. acetonitrile).

Alternatively, compounds of formula XXII in which $R^a$ and $R^b$ both represent H may be prepared by reduction of a corresponding compound of formula XXXVII,

XXXVII wherein $R^c$ to $R^h$ are as hereinbefore defined, for example at between room and reflux temperature in the presence of a suitable reducing agent (e.g. LiAlH$_4$) and an appropriate solvent (e.g. diethyl ether or THF).

Compounds of formula XXVII in which B represents $C_{1-4}$ alkylene may be prepared by coupling a compound of formula XXXVIII,

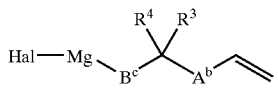

XXXVIII wherein $B^c$ represents $C_{1-4}$ alkylene, Hal represents chloro, bromo or iodo, and $A^b$, $R^3$ and $R^4$ are as hereinbefore defined, with a compound of formula X, as hereinbefore defined, for example at between −25° C. and room temperature in the presence of a suitable zinc(II) salt (e.g. anhydrous $ZnBr_2$), an appropriate catalyst (e.g. $Pd(PPh_3)_4$ or $Ni(PPh_3)_4$) and a reaction-inert organic solvent (e.g. THF, toluene or diethyl ether).

Compounds of formula XXXV may be prepared in analogous fashion to compounds of formula XIIIA and XIIIB (i.e. from the corresponding alcohol).

Compounds of formula XXXVI in which $R^a$ to $R^h$ all represent H may be prepared by reduction of a corresponding compound of formula XXXIX,

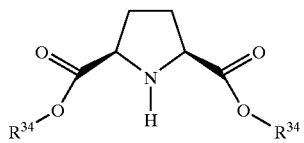

XXXIX or an N-protected derivative thereof, wherein $R^{34}$ represents H or $C_{1-4}$ alkyl, for example under conditions known to those skilled in the art (e.g. when $R^{34}$ represents H, reduction may be performed by reaction at between 0° C. and room temperature with borane or a suitable adduct thereof (e.g. $BH_3.THF$) in the presence of a suitable solvent (e.g. THF)), followed by conversion of the resulting hydroxy groups to $L^2$ groups under conditions to known to those skilled in the art (e.g. for compounds of formula XXXVI in which $L^2$ represents chloro, by reaction with thionyl chloride).

Compounds of formula XXXVII may be prepared by reaction of a corresponding compound of formula XL,

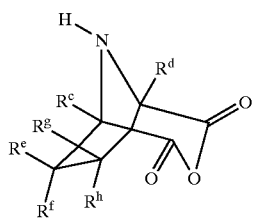

XL wherein $R^c$ to $R^h$ are as hereinbefore defined, with ammonia or a protected derivative thereof (e.g. benzylamine), for example at between −10° C. and room temperature, optionally in the presence of a suitable solvent (e.g. $CH_2Cl_2$ or benzene), followed by cyclisation of the resulting acid-amide intermediate under conditions known to those skilled in the art (e.g. by reaction with a suitable dehydrating agent (e.g. acetic anhydride or oxalyl chloride)).

Compounds of formula XXXIX may be prepared by reaction of a corresponding compound of formula XLI,

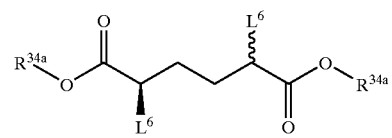

XLI wherein $R^{34a}$ represents $C_{1-4}$ alkyl and $L^6$ represents a leaving group (such as halo), with ammonia or a protected derivative thereof (e.g. benzylamine), for example at between room and reflux temperature in the presence of a suitable solvent (e.g. benzene), followed, if necessary, by conversion of the $R^{34a}$ groups to $R^{34}$ groups under conditions well known to those skilled in the art.

Compounds of formula XL may be prepared by dehydration of a corresponding compound of formula XXXIX in which $R^{34}$ represents H under conditions known to those skilled in the art (for example by reaction with a suitable dehydrating agent such as acetic anhydride or 1,3-dicyclohexylcarbodiimide).

Compounds of formulae V, VI, IX, X, XI, XIV, XV, XVI, XVII, XIX, XX, XXI, XXIII, XXIV, XXV, XXVI, XXVIII, XXIX, XXX, XXXIA, XXXIB, XXXIIA, XXXIIB, XXXIII, XXXIV, XXXVII and XLI and derivatives thereof, are either commercially available, are known in the literature, or may be obtained either by analogy with the processes described herein, or by conventional synthetic procedures, in accordance with standard techniques, from readily available starting materials using appropriate reagents and reaction conditions.

Substituents on the aryl (e.g. phenyl), and (if appropriate) heterocyclic, group(s) in compounds defined herein may be converted to other claimed substituents using techniques well known to those skilled in the art. For example, hydroxy may be converted to alkoxy, phenyl may be halogenated to give halophenyl, nitro may be reduced to give amino, amino may be acetylated to give acetylamino, etc.

The skilled person will also appreciate that various standard substituent or functional group interconversions and transformations within certain compounds of formula I will provide other compounds of formula I. For example, carbonyl may be reduced to hydroxy or alkylene, hydroxy may be converted to halo, and certain acyclic groups may be converted to certain heterocyclic groups under conditions known to those skilled in the art, for example as described in Comprehensive Heterocyclic Chemistry II, edited by A R Katritsky, C W Rees and E F V Scriven, $1^{st}$ Edition, Elsevier Science Ltd., Volumes 1–11 (1996).

The compounds of formula I may be isolated from their reaction mixtures using conventional techniques.

It will be appreciated by those skilled in the art that, in the process described above, the functional groups of intermediate compounds may be, or may need to be, protected by protecting groups.

Functional groups which it is desirable to protect include hydroxy, amino and carboxylic acid. Suitable protecting groups for hydroxy include trialkylsilyl and diarylalkylsilyl groups (e.g. tert-butyldimethylsilyl, tert-butyldiphenylsilyl or trimethylsilyl), tetrahydropyranyl and alkylcarbonyl groups (e.g. methyl- and ethylcarbonyl groups). Suitable protecting groups for amino include benzyl, tert-butyloxycarbonyl, 9-fluorenyl-methoxycarbonyl or benzyloxycarbonyl. Suitable protecting groups for amidino and guanidino include benzyloxycarbonyl. Suitable protecting groups for carboxylic acid include $C_{1-6}$ alkyl or benzyl esters.

The protection and deprotection of functional groups may take place before or after any of the reaction steps described hereinbefore.

Protecting groups may be removed in accordance with techniques which are well known to those skilled in the art and as described hereinafter.

The use of protecting groups is fully described in "Protective Groups in Organic Chemistry", edited by J. W. F. McOmie, Plenum Press (1973), and "Protective Groups in Organic Synthesis", $3^{rd}$ edition, T. W. Greene & P. G. M. Wutz, Wiley-Interscience (1999).

Persons skilled in the art will appreciate that, in order to obtain compounds of formula I in an alternative, and, on some occasions, more convenient, manner, the individual process steps mentioned herein may be performed in a different order, and/or the individual reactions may be performed at a different stage in the overall route (i.e. substituents may be added to and/or chemical transformations performed upon, different intermediates to those associated hereinbefore with a particular reaction). This will depend inter alia on factors such as the nature of other functional groups present in a particular substrate, the availability of key intermediates and the protecting group strategy (if any) to be adopted. Clearly, the type of chemistry involved will influence the choice of reagent that is used in the said synthetic steps, the need, and type, of protecting groups that are employed, and the sequence for accomplishing the synthesis.

It will also be appreciated by those skilled in the art that, although certain protected derivatives of compounds of formula I, which may be made prior to a final deprotection stage, may not possess pharmacological activity as such, they may be administered parenterally or orally and thereafter metabolised in the body to form compounds of formula I which are pharmacologically active. Such derivatives may therefore be described as "prodrugs". Moreover, certain compounds of formula I may act as prodrugs of other compounds of formula I.

All prodrugs of compounds of formula I are included within the scope of the invention.

Some of the intermediates referred to hereinbefore are novel. According to a farther aspect of the invention there is thus provided: (a) compounds of formulae IVA and IVB, as hereinbefore defined, or protected derivatives thereof; (b) compounds of formulae XIIIA and XIIIB, as hereinbefore defined, or protected derivatives thereof.

Medical and Pharmaceutical Use

The compounds of formula I are useful because they possess pharmacological activity. They are therefore indicated as pharmaceuticals.

Thus, according to a further aspect of the invention there is provided the compounds of formula I for use as pharmaceuticals.

In particular, the compounds of formula I exhibit myocardial electrophysiological activity, for example as demonstrated in the test described below.

The compounds of formula I are thus expected to be useful in both the prophylaxis and the treatment of arrhythmias, and in particular atrial and ventricular arrhythmias.

The compounds of formula I are thus indicated in the treatment or prophylaxis of cardiac diseases, or in indications related to cardiac diseases, in which arrhythmias are believed to play a major role, including ischaemic heart disease, sudden heart attack, myocardial infarction, heart failure, cardiac surgery and thromboembolic events.

In the treatment of arrhythmias, compounds of formula I have been found to selectively delay cardiac repolarization, thus prolonging the QT interval, and, in particular, to exhibit class III activity. Although compounds of formula I have been found to exhibit class III activity in particular, in the treatment of arrhythmias, their mode(s) of activity is/are not necessarily restricted to this class.

According to a further aspect of the invention, there is provided a method of treatment of an arrhythmia which method comprises administration of a therapeutically effective amount of a compound of formula I to a person suffering from, or susceptible to, such a condition.

Pharmaceutical Preparations

The compounds of formula I will normally be administered orally, subcutaneously, intravenously, intraarterially, transdermally, intranasally, by inhalation, or by any other parenteral route, in the form of pharmaceutical preparations comprising the active ingredient either as a free base, a pharmaceutically acceptable ion exchanger or a non-toxic organic or inorganic acid addition salt, in a pharmaceutically acceptable dosage form.

Depending upon the disorder and patient to be treated, as well as the route of administration, the compositions may be administered at varying doses.

The compounds of formula I may also be combined with any other drugs useful in the treatment of arrhythmias and/or other cardiovascular disorders.

According to a further aspect of the invention there is thus provided a pharmaceutical formulation including a compound of formula I in admixture with a pharmaceutically acceptable adjuvant, diluent or carrier.

Suitable daily doses of the compounds of formula I in therapeutic treatment of humans are about 0.005 to 10.0 mg/kg body weight at oral administration and about 0.005 to 5.0 mg/kg body weight at parenteral administration.

The compounds of formula I have the advantage that they are effective against cardiac arrhythmias.

Compounds of formula I may also have the advantage that they may be more efficacious than, be less toxic than, have a broader range of activity (including exhibiting any combination of class I, class II, class III and/or class IV activity (especially class I and/or class IV activity in addition to class III activity)) than, be more potent than, be longer acting than, produce fewer side effects (including a lower incidence of proarrhythmias such as torsades de pointes) than, be more easily absorbed than, or that they may have other useful pharmacological properties over, compounds known in the prior art.

Biological Tests

Test A

Primary Electrophysiological Effects in Anaesthetised Guinea Pigs

Guinea pigs weighing between 660 and 1100 g were used. The animals were housed for at least one week before the experiment and had free access to food and tap water during that period.

Anaesthesia was induced by an intraperitoneal injection of pentobarbital (40 to 50 mg/kg) and catheters were introduced into one carotid artery (for blood pressure recording and blood sampling) and into one jugular vein (for drug infusions). Needle electrodes were placed on the limbs for recording of ECGs (lead II). A thermistor was placed in the rectum and the animal was placed on a heating pad, set to a rectal temperature of between 37.5 and 38.5° C.

A tracheotomy was performed and the animal was artificially ventilated with room air by use of a small animal ventilator, set to keep blood gases within the normal range for the species. In order to reduce autonomic influences both vagi were cut in the neck, and 0.5 mg/kg of propranolol was given intravenously, 15 minutes before the start of the experiment.

The left ventricular epicardium was exposed by a left-sided thoracotomy, and a custom-designed suction electrode for recording of the monophasic action potential (MAP) was applied to the left ventricular free wall. The electrode was kept in position as long as an acceptable signal could be recorded, otherwise it was moved to a new position. A bipolar electrode for pacing was clipped to the left atrium. Pacing (2 ms duration, twice the diastolic threshold) was performed with a custom-made constant current stimulator. The heart was paced at a frequency just above the normal sinus rate during 1 minute every fifth minute throughout the study.

The blood pressure, the MAP signal and the lead II ECG were recorded on a Mingograph ink-jet recorder (Siemens-Elema, Sweden). All signals were collected (sampling frequency 1000 Hz) on a PC during the last 10 seconds of each pacing sequence and the last 10 seconds of the following minute of sinus rhythm. The signals were processed using a custom-made program developed for acquisition and analysis of physiological signals measured in experimental animals (see Axenborg and Hirsch, *Comput. Methods Programs Biomed.* 41, 55 (1993)).

The test procedure consisted of taking two basal control recordings, 5 minutes apart, during both pacing and sinus rhythm. After the second control recording, the first dose of the test substance was infused in a volume of 0.2 mL into the jugular vein catheter for 30 seconds. Three minutes later, pacing was started and a new recording was made. Five minutes after the previous dose, the next dose of test substance was administered. Six to ten consecutive doses were given during each experiment.

Data Analysis

Of the numerous variables measured in this analysis, three were selected as the most important for comparison and selection of active compounds. The three variables selected were the MAP duration at 75 percent repolarization during pacing, the atrio-ventricular (AV) conduction time (defined as the interval between the atrial pace pulse and the start of the ventricular MAP) during pacing, and the heart rate (defined as the RR interval during sinus rhythm). Systolic and diastolic blood pressure were measured in order to judge the haemodynamic status of the anaesthetised animal. Further, the ECG was checked for arrhythmias and/or morphological changes.

The mean of the two control recordings was set to zero and the effects recorded after consecutive doses of test substance were expressed as percentage changes from this value. By plotting these percentage values against the cumulative dose administered before each recording, it was possible to construct dose-response curves. In this way, each experiment generated three dose-response curves, one for MAP duration, one for AV-conduction time and one for the sinus frequency (RR interval). A mean curve of all experiments performed with a test substance was calculated, and potency values were derived from the mean curve. All dose-response curves in these experiments were constructed by linear connection of the data points obtained. The cumulative dose prolonging the MAP duration by is 10% from the baseline was used as an index to assess the class III electrophysiological potency of the agent under investigation ($D_{10}$).

Test B

Glucocorticoid-treated Mouse Fibroblasts as a Model to Detect Blockers of the Delayed Rectifier K Current IC50 for K channel blockade was determined using a microtitre plate based screen method, based on membrane potential changes of glucocorticoid-treated mouse fibroblasts. The membrane potential of glucocorticoid-treated mouse fibroblasts was measured using fluorescence of the bisoxonol dye $DiBac_{4(3)}$, which could be reliably detected using a fluorescence laser imaging plate reader (FLIPR). Expression of a delayed rectifier potassium channel was induced in mouse fibroblasts by 24 hours exposure to the glucocorticoide dexamehasone (5 $\mu$M). Blockade of these potassium channels depolarised the fibroblasts, resulting in increased fluorescence of $DiBac_{4(3)}$.

Mouse ltk fibroblasts (L-cells) were purchased from American Type Culture Collection (ATCC, Manassa, Va.), and were cultured in Dulbeccos modified eagle medium supplemented with fetal calf serum (5% vol/vol), penicillin (500 units/mL), streptomycin (500 $\mu$g/mL) and L-alanine-L-glutamine (0.862 mg/mL). The cells were passaged every 3–4 days using trypsin (0.5 mg/mL in calcium-free phosphate buffered saline, Gibco BRL). Three days prior to experiments, cell-suspension was pipetted out into clear-bottom, black plastic, 96-well plates (Costar) at 25 000 cells/well.

The fluorescence probe $DiBac_{4(3)}$ (DiBac Molecular probes) was used to measure membrane potential. $DiBac_{4(3)}$ maximally absorbs at 488 nM and emits at 513 nM. $DiBac_{4(3)}$ is a bisoxonol, and thus is negatively charged at pH 7. Due to its negative charge, the distribution of $DiBac_{4(3)}$ across the membrane is dependent upon the transmembrane potential: if the cell depolarizes (i.e. the cell interior becomes less negative relative to cell exterior), the $DiBac_{4(3)}$ concentration inside the cell increases, due to electrostatic forces. Once inside the cell, $DiBac_{4(3)}$ molecules can bind to lipids and proteins, which causes an increase in fluorescence emission. Thus, a depolarization will be reflected by an increase in $DiBac_{4(3)}$ fluorescence. The change in $DiBac_{4(3)}$ fluorescence was detected by a FLIPR.

Prior to each experiment, the cells were washed 4 times in phosphate-buffered saline (PBS) to remove all culture media. The cells were then treated with 5 $\mu$M $DiBac_{4(3)}$ (in 180 mL of PBS) at 35° C. Once a stable fluorescence was reached (usually after 10 min), 20 $\mu$L of the test substance was added, using FLIPR's internal 96 well pipetting system. Fluorescence measurements were then taken every 20 sec for a further 10 min. All experiments were carried out at 35° C., due to the high temperature sensitivity of both delayed rectifier potassium channel conductance and $DiBac_{4(3)}$ fluorescence. Test substances were prepared in a second 96 well plate, in PBS containing 5 $\mu$M $DiBac_{4(3)}$. The concentration of substance prepared was 10 times that of the desired concentration in the experiment as an additional 1:10 dilution occurred during addition of substance during the experiment. Dofetilide (10 $\mu$M) was used as a positive control, i.e. to determine the maximum increase in fluorescence.

Curve-fitting, used to determine the IC50 values, was performed with the Graphpad Prism program (Graphpad Software Inc., San Diego, Calif.).

Test C

Metabolic Stability of Test Compounds

An in vitro screen was set up to determine the metabolic stability of the compounds of formula I.

The hepatic S-9 fraction from dog, man, rabbit and rat with NADPH as co-factor was used. The assay conditions were as follows: S-9 (3 mg/mL), NADPH (0.83 mM), Tris-HCl buffer (50 mM) at pH 7.4 and 10 µM of test compound.

The reaction was started by addition of test compound and terminated after 0, 1, 5, 15 and 30 minutes by raising the pH in the sample to above 10 (NaOH; 1 mM). After solvent extraction, the concentration of test compound was measured against an internal standard by LC (fluorescence/UV detection).

The percentage of test compound remaining after 30 minutes (and thus $t_{1/2}$) was calculated and used as a measure for metabolic stability.

The invention is illustrated by way of the following examples.

EXAMPLES

General Experimental Procedures

Mass spectra were recorded on one of the following instruments: a Perkin-Elmer SciX API 150ex spectrometer; a VG Quattro II triple quadrupole; a VG Platform II single quadrupole; or a Micromass Platform LCZ single quadrupole mass spectrometer (the latter three instruments were equipped with a pneumatically assisted electrospray interface (LC-MS)). $^1$H NMR and $^{13}$C NMR measurements were performed on a BRUKER ACP 300 and Varian 300, 400 and 500 spectrometers, operating at $^1$H frequencies of 300, 400 and 500 MHz respectively, and at $^{13}$C frequencies of 75.5, 100.6 and 125.7 MHz respectively. Alternatively, $^{13}$C NMR measurements were performed on a BRUKER ACE 200 spectrometer at a frequency of 50.3 MHz.

Rotamers may or may not be denoted in spectra depending upon ease of interpretation of spectra. Unless otherwise stated, chemical shifts are given in ppm with the solvent as internal standard.

"CMA" for TLC analysis and chromatography is defined as: 88% $CH_2Cl_2$, 10% $CH_3OH$ and 2% concentrated ammonium hydroxide.

Synthesis of Intermediates

The following intermediates were not commercially available, and were therefore prepared by the methods described below.

Preparation A tert-Butyl 3,8-diazabicyclo[3.2.1]octane-3-carboxylate hydrochloride (a) Dimethyl (2R,5S)-2,5-dibromohexanedioate Bromine (58.5 mL, 1.14 mol) was added dropwise to adipoyl chloride (100 g, 0.54 mol) at 75–80° C. while being irradiated with a 250 W lamp. After the addition was completed, the reaction was heated and irradiated for an additional 2 h. Reaction was then cooled to 25° C. and evacuated to 10–14 mmHg to remove any excess bromine. The resulting amber oil was slowly poured into rapidly stirring −70° C. methanol (500 mL). The resulting suspension was stirred for 16 h and then filtered. The filter cake of off-white crystals was dried to constant weight in vacuo to afford 70.7 g of the sub-title compound. Two more crops of crystals provided an additional 80.0 g. Total yield for three crops of crystals was 150.7 g (81%) for the sub-title compound. (J. Org. Chem. 1990, 55, 2950–2952)

Mp 74–76° C.

$^1$H NMR (300 MHz, $CDCl_3$) δ 4.27 (m, 2H), 3.78 (s, 6H), 2.31 (m, 2H), 2.07 (m, 2H).

(b) cis-Dimethyl-1-benzyl-2,5-pyrrolidinedicarboxylate

Benzylamine (177 mL, 1.62 mol) was added dropwise to a refluxing solution of meso-dimethyl-2,5-dibromoadipate (183.9 g, 0.54 mol, from step (a) above) in benzene (2 L). After addition, reflux was continued for 10 h. The reaction was cooled to 25° C. and diluted with $Et_2O$ (1 L). It was filtered to remove the salts, and the filtrate concentrated in vacuo to afford 190 g of oil (more than quantitative yield). The oil was used in step c below without further purification.

(c) cis-1-Benzyl-2,5-pyrrolidinedicarboxylic acid

A solution of NaOH (47.5 g, 1.18 mol) in water (800 mL) was added to a solution of cis-dimethyl-1-benzyl-2,5-pyrrolidinedicarboxylate (190 g, from step (b) above) in methanol (400 mL). After stirring rapidly for two hours, the reaction was cooled to 0° C. and washed with $Et_2O$ (1 L). The aqueous layer was made acidic to a pH of 4 with 6 N HCl (~200 mL). The precipitate was collected and dried in vacuo to afford 60.0 g of the sub-title compound. A second crop of crystals was obtained by concentrating in vacuo the aqueous filtrate to 400 mL. The precipitate was collected and dried to afford 32 g of the sub-title compound. Total for the two crops was 92.0 g (68% for steps (b) and (c) combined).

$^1$H NMR (300 MHz, DMSO-$d_6$) δ 7.60 (dd, 2H), 7.42 (t, 3H), 4.58 (s, 2H), 4.45 (t, 2H), 2.52 (m, 2H), 2.03 (m, 2H).

(d) cis-1-Benzyl-2,5-(dihydroxymethyl)pyrrolidine hydrochloride

A solution of $BH_3$ in THF (560 mL, 0.56 mol) was added to a stirred suspension of cis-1-benzyl-2,5-pyrrolidinedicarboxylic acid (33 g, 0.13 mol; from step (c) above) in THF (100 mL) at 0° C. After the addition was complete, the reaction was stirred at 25° C. for 18 h, refluxed for 1 h and then cooled to 0° C. before a solution of HCl in methanol (560 mL) was added dropwise. The reaction was allowed to warm to 25° C. and then refluxed for 1 h. The reaction was concentrated in vacuo to afford 31.7 g (98%) of the sub-title compound as a colourless oil which solidified on standing.

$^1$H NMR (300 MHz, $CD_3OD$) δ 7.61 (m, 2H), 7.49 (m, 3H), 4.61 (s, 2H), 3.88 (m, 2H), 3.50–3.72 (m, 4H), 2.15 (m, 2H), 1.95 (m, 2H).

(e) cis-1-Benzyl-2,5-bis(chloromethyl)pyrrolidine hydrochloride

Thionyl chloride (500 mL) was added to cis-1-benzyl-2,5-(dihydroxymethyl)pyrrolidine hydrochloride (31.7 g, 0.13 mol, from step (e) above) and stirred 24 h at 25° C. The reaction was concentrated in vacuo to afford 37.5 g (98%) of the sub-title compound as an off-white crystalline solid.

$^1$H NMR (300 MHz, $CD_3OD$) δ 7.65 (m, 2H), 7.52 (m, 3H), 4.71 (s, 2H), 4.12 (m, 2H), 3.78 (m, 4H), 2.48 (m, 2H) 2.08 (m, 2H)

MS (API): 258 m/z $(M+H)^+$ (f) 8-Benzyl-3-(2-propenyl)-3,8-diazabicyclo[3.2.1]octane Allylamine (9.5 mL, 0.13 mol) was added to a suspension of cis-1-benzyl-2,5-bis(chloromethyl)pyrrolidine hydrochloride (37.5 g, 0.13 mol, from step (e) above), NaI (47.6 g, 0.32 mol) and $NaHCO_3$ (106.7 g, 1.27 mol) in acetonitrile (1.8 L). The reaction was heated at reflux for 8 h, filtered, and the filtrate concentrated in vacuo. The residue was partitioned between ethyl acetate and ice cold 1 N NaOH. The ethyl acetate layer was separated, dried (Na$_2$SO$_4$), filtered and concentrated in vacuo to afford 31.1 g of an oil. The oil was chromatographed on a column of silica (75 mm×220 mm) eluting with a mixture of chloroform, methanol and conc. NH$_4$OH (240:9:1). Fractions (100 mL each) 5–10 were combined and concentrated in vacuo to afford 22.2 g (72%) of the sub-title compound.

$^1$H NMR (300 MHz, CD$_3$OD): δ 7.35–7.15 (m, 5H), 5.35–5.20 (m, 1H), 5.18–5.02 (m, 2H), 3.48 (s, 2H), 3.09 (br. s, 2H), 2.92 (d, 2H), 2.58 (dd, 2H), 2.25 (d, 2H), 1.92–2.02 (m, 2H), 1.85–1.75 (m, 2H).

(g) 8-Benzyl-3,8-diazabicyclo[3.2.1]octane

A mixture of 8-benzyl-3-(2-propenyl)-3,8-diazabicyclo[3.2.1]octane (22.2 g, 92.7 mmol), 1,3-dimethylbarbituric acid (21.5 g, 137.0 mmol), Pd$_2$(dba)$_3$ (5 g, 5 mmol) and P(C$_6$H$_5$)$_3$ (5.2 g, 20.0 mmol) in methylene chloride (500 mL) was heated at reflux for 16 h. The reaction was poured into 1 N HCl (250 mL) at 0° C. The aqueous acidic layer was separated and made basic with 6 N NaOH, then extracted with ethyl acetate (2×150 mL).

The combined extracts were dried (Na$_2$SO$_4$), filtered and concentrated in vacuo to afford 13.9 g (75%) of the sub-title compound.

$^1$H NMR (300 MHz, CD$_3$OD) δ 7.42–7.18 (m, 5H), 3.49 (s, 2H), 3.07 (br. s, 2H), 2.90 (d, 2H), 2.57 (d, 2H), 2.18–2.04 (m, 2H), 1.85–1.75 (m, 2H).

(h) 8-Benzyl-3-(tert-butoxycarbonyl)-3,8-diazabicyclo[3.2.1]octane hydrochloride A solution of 8-benzyl-3,8-diazabicyclo[3.2.1]octane (13.9 g, 68.8 mmol, from step (g) above) and di-tert-butyl dicarbonate (15.5 g, 71.0 mmol) in THF was stirred for 18 h at 25° C. The reaction was concentrated ill vacuo to afford a colorless oil which was dissolved in ethyl acetate (50 mL). The ethyl acetate solution was cooled to 0° C. and a solution of 1 M HCl in Et$_2$O (69 mL) was added dropwise with stirring. It was stirred an additional 30 min. after the addition was complete. The off-white precipitate was collected and dried in vacuo to afford 13.1 g of the sub-title compound. The filtrate was concentrated to dryness and the residue slurried with Et$_2$O to afford an additional 3.4 g of the sub-title compound. A total of 16.5 g (72%) of the sub-title compound was obtained.

$^1$H NMR (300 MHz, CD$_3$OD) δ 7.67–7.48 (m, 5H), 4.28 (s, 2H), 4.12–3.85 (m, 4H), 3.45–3.18 (m, 2H), 2.52–2.35 (m, 2H), 2.10–1.93 (m, 2H), 1.50 (s, 9H).

(i) tert-Butyl 3,8-diazabicyclo[3.2.1]octane-3-carboxylate hydrochloride

Palladium on carbon (10% w/w, 500 mg) was added to a solution of 8-benzyl-3-(tert-butoxycarbonyl)-3,8-diazabicyclo[3.2.1]octane hydrochloride (16.5 g, 48.0 mmol, see step (h) above) in methanol (250 mL) under a nitrogen atmosphere at 25° C. The nitrogen atmosphere was exchanged for a hydrogen atmosphere (1 atm of pressure) and the reaction was stirred rapidly. After 4 h the stirring was stopped and the reaction was filtered through a pad of Celite®. The filtrate was concentrated in vacuo to afford an off-white solid (11.6 g). The solid was slurried in acetonitrile, collected and dried in vacuo to afford 10.5 g (86%) of the title compound.

Mp 195–200° C.

MS (API): 213 m/z (M+H)$^+$ $^1$H NMR (300 MHz, CD$_3$OD) δ 4.15–3.90 (m, 4H), 3.42–3.12 (m, 2H), 2.18–2.05 (m, 2H), 1.98–1.85 (m, 2H), 1.50 (s, 9H).

$^{13}$C NMR (75 MHz, CD$_3$OD) δ 156.5, 82.2, 55.9, 47.5, 29.2, 26.2.

Preparation B tert-Butyl 3,8-diazabicyclo[3.2.1]octane-8-carboxylate (a) 8-Benzyl-3-oxa-8-azabicyclo[3.2.1]octan-2,4-dione A solution of cis-1-benzyl-2,5-pyrrolidinedicarboxylic acid (60 g, 0.24 mol; from Preparation A, step (c) above) and dicyclohexylcarbodiimide (49.7 g, 0.24 mol) in THF (1.2 L) was heated at reflux for 18 hours. The reaction was cooled and filtered to remove the urea by-product. The filtrate was concentrated in vacuo to afford a dark brown viscous oil which was used in the next step without further purification.

$^1$H NMR (300 MHz, CDCl$_3$) δ 7.18–7.42 (m, 5H), 3.85–3.95 (m, 2H), 3.80 (s, 2H), 2.29–2.45 (m, 2H), 1.95–2.09 (m, 2H).

(b) cis-1-Benzyl-5-(N-benzylcarbamoyl)-pyrrolidine-2-carboxylic acid

Benzylamine (25.7 g, 0.24 mol) was added to an ice cold solution of 8-benzyl-3-oxa-8-azabicyclo[3.2.1]octan-2,4-dione (0.24 mol; from step (a) above) in CH$_2$Cl$_2$ (1 L). The solution was stirred overnight at room temperature and concentrated in vacuo. The residue was dissolved in Et$_2$O and extracted with 2 N NaOH solution. The aqueous base layer was separated and acidified to pH 4. The precipitated product was collected and dried to afford 49.5 g (61% for two steps) of the sub-title compound as a tan solid.

$^1$H NMR (300 MHz, DMSO-d$_6$) δ 8.68 (t, 1H), 7.05–7.38 (m, 10H), 4.18–4.32 (m, 2H), 3.73–3.89 (m, 2H), 3.42–3.61 (m, 2H), 2.02–2.25 (m, 2H), 1.62–1.86 (m, 2H).

(c) 3,8-Dibenzyl-3,8-diazabicyclo[3.2.1]octan-2,4-dione hydrochloride

Oxalyl chloride (18.5 g, 0.14 mol) was added dropwise to an ice cold suspension of cis-1-benzyl-5-(N-benzylcarbamoyl)-pyrrolidine-2-carboxylic acid (49.5 g, 0.14 mol; from step (b) above) in CH$_2$Cl$_2$ (500 mL) at such a rate that the reaction temperature did not exceed 8° C. The reaction slowly warmed to room temperature overnight with stirring. The reaction mixture was then concentrated in vacuo. The residue was slurried with 2-propanol and filtered to afford 39.5 g (84%) of the sub-title compound as a light tan solid.

$^1$H NMR (300 MHz, CDCl$_3$) δ 6.98–7.43 (m, 10H), 4.90 (s, 2H), 3.78–3.88 (m, 2H), 3.62 (s, 2H), 2.21–2.39 (m, 2H), 1.79–195 (m, 2H).

(d) 3-Benzyl-3,8-diazabicyclo[3.2.1]octan-2,4-dione hydrochloride 3,8-Dibenzyl-3,8-diazabicyclo[3.2.1]octan-2,4-dione hydrochloride (39 g, 0.11 mol; from step (c) above) was added to a suspension of 10% Pd/C (500 mg) in methanol (500 mL) under a blanket of N$_2$. The N$_2$ atmosphere was exchanged for H$_2$ (one atmosphere of pressure). The reaction was stirred vigorously overnight. The catalyst was removed by filtration and the filtrate concentrated in vacuo to afford 28.3 g (96%) of the sub-title compound as a light tan solid.

$^1$H NMR (300 MHz, CD$_3$OD) δ 7.22–7.39 (m, 5H), 4.86 (s, 2H), 4.68–4.78 (m, 2H), 2.42–2.61 (m, 2H), 2.17–2.31 (m, 2H).

(e) 3-Benzyl-3,8-diazabicyclo[3.2.1]octane

3-Benzyl-3,8-diazabicyclo[3.2.1]octan-2,4-dione (28 g, 0.10 mol; from step (d) above) was added in portions to a suspension of LiAlH$_4$ (19 g, 0.50 mol) in THF (500 mL).

After addition of the solid, the reaction was slowly warmed to reflux, and then refluxed overnight. The reaction was cooled in an ice bath. To the cold reaction mixture there was added sequentially $H_2O$ (19 mL), 15% NaOH solution (19 mL) and $H_2O$ (57 mL). The resulting mixture was stirred for 30 min then filtered through a pad of Celite®. The filtrate was concentrated in vacuo to afford 20.5 g (86%) of the sub-title compound as a golden oil. A hydrochloride salt may be obtained from $CH_3CN$ and a solution of hydrogen chloride in EtOAc.

Mp 205–210° C.

$^1$H NMR (HCl salt, 300 MHz, $CD_3OD$): δ 7.21–7.39 (m, 5H), 3.98 (br. s, 2H), 3.58 (s, 2H,), 2.75–2.89 (m, 2H), 2.42–2.53 (d, 2H), 1.92–2.23 (m, 4H).

$^{13}$C NMR (75 MHz, $CD_3OD$) δ 138.6, 130.3, 129.8, 128.5, 62.2, 57.3, 56.2, 27.4.

MS (API): 203 m/z $(M+H)^+$ (f) tert-Butyl 3-benzyl-3,8-diazabicyclo[3.2.1]octane-8-carboxylate A solution of 3-benzyl-3,8-diazabicyclo[3.2.1]octane (12.4 g, 61.3 mmol; from step (e) above) and di-tert-butyl dicarbonate (17.4 g, 79.7 mmol) in THF (1.0 L) was stirred at room temperature for 18 h. The reaction was concentrated in vacuo to give the crude product as an oil. Flash chromatography on silica gel eluting with methylene chloride and methanol (98:2) afforded 13.7 g (74%) of the sub-title compound.

$^1$H NMR (300 MHz, $CDCl_3$) δ 7.17–7.38 (m, 5H), 4.03–4.27 (m, 2H), 3.38–3.54 (m, 2H), 2.52–2.68 (m, 2H), 2.15–2.38 (m, 2H), 1.72–1.95 (m, 4H), 1.42 (s, 9H).

(g) tert-Butyl 3,8-diazabicyclo[3.2.1]octane-8-carboxylate

A solution of 3-benzyl-8-(tert-butoxycarbonyl)-3,8-diazabicyclo[3.2.1]octane (13.7 g, 45.3 mmol; from step (f) above) and acetic acid (2.7 g, 45.3 mmol) in methanol (1.0 L) was flushed with nitrogen. To the solution was added 10% palladium on carbon (1.4 g). The resulting mixture was stirred under a hydrogen atmosphere for 5 h. The reaction was filtered through Celite® and the filtrate concentrated to afford 8.3 g of white solid. This material was combined with a previous lot to provide a total of 11.9 g of crude product. Flash chromatography of the combined material on silica gel eluting with methylene chloride, methanol and concentrated ammonium hydroxide (93:6:1) provided 8.7 g of the title compound.

Mp 102–104° C.

$^1$H NMR (300 MHz, $CDCl_3$) δ 3.99–4.22 (m, 2H), 2.88–3.22 (m, 2H), 2.58–2.68 (d, 2H), 1.73–2.02 (m, 4H), 1.48 (s, 9H).

$^{13}$C NMR (mixture of conformers, 75 MHz, $CDCl_3$): δ 153.8, 79.2, 55.5, 54.3, 50.9, 28.2, 27.6, 26.4.

MS (CI): 213 m/z $(M+H)^+$

Preparation C

4-[3-(3,8-Diazabicyclo[3.2.1]oct-8-yl)-2-hydroxy propoxy]benzonitrile (a) 4-[3-(3-Benzyl-3,8-diazabicyclo[3.2.1]oct-8-yl)-2-hydroxypropoxy]benzonitrile A mixture of 3-benzyl-3,8-diazabicyclo[3.2.1]octane (3.46 g, 17.1 mmol; from Preparation B, step (e) above) and 4-(2-oxiranylmethoxy)benzonitrile (3.00 g, 17.1 mmol; prepared as described in international patent application WO 99/31100) in 2-propanol (70 mL) and $H_2O$ (7 mL) was stirred at 60° C. for 22 h. The reaction mixture was concentrated in vacuo. The residue was dissolved in $CH_2Cl_2$ (200 mL) and washed with water (50 mL) and brine (50 mL). The organic layer was dried ($NaSO_4$), filtered and concentrated in vacuo to give the crude product. Flash chromatography on silica gel eluting with $CH_2Cl_2$:CMA (8:1) gave 5.74 g (89%) of the sub-title compound as a yellow oil.

$^1$H NMR (300 MHz, $CDCl_3$) δ 7.58 (d, J=8.7 Hz, 2H), 7.12–7.42 (m, 5H), 6.97 (d, J=8.7 Hz, 2H), 3.88–4.10 (m, 3H), 3.47 (s, 2H), 3.17 (br. s, 1H), 3.06 (br. s, 1H), 2.49–2.71 (m, 3H), 2.15–2.46 (m, 3H), 1.67–2.02 (m, 4H).

(b) 4-[3-(3,8-Diazabicyclo[3.2.1]oct-8-yl)-2-hydroxypropoxy]benzonitrile

To a cold solution of 4-[3-(3-benzyl-3,8-diazabicyclo [3.2.1.]oct-8-yl)-2-hydroxypropoxy]benzonitrile (5.74 g, 15.2 mmol; from step (a) above) in acetonitrile (100 mL) there was added 12 M HCl (3.2 mL). The reaction mixture was stirred for 15 minutes, concentrated in vacuo and dried under high vacuum overnight. The resulting hydrochloride salt was added to a suspension of 10% Pd/C (700 mg) in methanol (500 mL). The reaction was then stirred under hydrogen (1 atmosphere of pressure) for 90 minutes. The mixture was filtered through Celite® and the filtrate concentrated in vacuo. The resulting residue was partitioned with saturated sodium bicarbonate (100 mL) and $CH_2Cl_2$ (150 mL). The organic layer was dried ($Na_2SO_4$), filtered and concentrated in vacuo to give the crude product. Flash chromatography on silica gel, eluting with $CH_2Cl_2$:CMA (4:1), gave 1.58 g (38%) of the sub-title compound.

Mp 125–128° C.

$^1$H NMR (300 MHz, $CDCl_3$) δ 7.59 (d, J=7.0 Hz, 2H), 6.98 (d, J=7.0 Hz, 2H), 3.81–4.09 (m, 3H), 2.82–3.23 (m, 4H), 2.47–2.78 (m, 4H), 2.27–2.43 (m, 1H), 1.58–2.09 (m, 4H).

$^{13}$C NMR (mixture of conformers, 75 MHz, $CDCl_3$) δ 162.2, 134.1, 119.3, 115.5, 104.4, 70.6, 66.7, 62.6, 62.4, 59.9, 59.6, 57.4, 56.7, 55.8, 52.1, 27.3, 26.2, 25.0.

MS (CI): 288 m/z $(M+H)^+$

Preparation D

4-{[3-(3,8-Diazabicyclo[3.2.1]oct-8-yl)propyl] amino}benzonitrile (a) 4-[(3-Hydroxypropyl)amino]benzonitrile A mixture of 4-fluorobenzonitrile (12.0 g, 99.1 mmol) and 3-amino-1-propanol (59.6 g, 793 mmol) was stirred at 80° C. under an inert atmosphere for 3 hours before water (150 mL) was added. The mixture was allowed to cool to rt, and was then extracted with diethyl ether. The organic layer was separated, dried ($Na_2SO_4$), filtered and concentrated in vacuo to yield 17 g (97%) of the title compound as an oil that crystallised upon standing.

(b) 3-(4-Cyanoanilino)propyl 4-methylbenzenesulfonate

A cooled (0° C.) solution of 4-[(3-hydroxypropyl)amino] benzonitrile (from step (a) above; 17 g, 96.5 mmol) in dry MeCN (195 mL) was treated with triethylamine (9.8 g, 96.5 mmol) and then p-toluenesulfonyl chloride (20.2 g, 106 mmol). The mixture was stirred at 0° C. for 90 minutes before being concentrated in vacuo. Water (200 mL) was added to the residue, and the aqueous solution was extracted with DCM. The organic phase was dried ($Na_2SO_4$), filtered and concentrated in vacuo. The resulting residue was purified by crystallisation from iso-propanol to yield 24.6 g (77%) of the sub-title compound.

(c) 4-{[3-(3-Benzyl-3,8-diazabicyclo[3.2.1]oct-8-yl)propyl]amino}benzonitrile

A mixture of 3-benzyl-3,8-diazabicyclo[3.2.1]octane (3.63 g, 17.9 mmol; from Preparation B, step (e) above), 3-(4-cyanoanilino)propyl 4-methylbenzenesulfonate (5.93 g, 17.9 mmol; from step (a) above) and potassium carbonate (2.47 g, 17.9 mmol) in dry DMF (85 mL) was stirred at 80° C. for 4 h. The reaction mixture was diluted with water (200 mL) and extracted with ether (4×200 mL). The combined extracts were washed with brine, dried ($Na_2SO_4$), filtered and concentrated ill vacuo to give the crude product. Flash chromatography on silica gel eluting with $CH_2Cl_2$:CMA (4:1) gave 6.26 g (97%) of the sub-title compound as a yellow oil.

$^1$H NMR (300 MHz, $CDCl_3$) δ 7.13–7.50 (m, 6H), 7.05 (br. s, 1H), 6.56 (d, 1H), 6.40 (d, 2H), 3.57 (s, 2H), 3.06–3.39 (m, 4H), 2.59–2.73 (m, 2H), 2.41–2.57 (m, 2H), 2.27–2.41 (m, 2H), 1.67–2.02 (m, 6H).

(d) 4-{[3-(3,8-Diazabicyclo[3.2.1]oct-8-yl)propyl]amino}benzonitrile

To a cold solution of 4-{[3-(3-benzyl-3,8-diazabicyclo[3.2.1]oct-8-yl)propyl]amino}benzonitrile (6.26 g, 17.4 mmol; from step (c) above) in acetonitrile (100 mL) was added 12 M HCl (5.8 mL). The reaction mixture was stirred for 15 minutes, concentrated in vacuo and dried under high vacuum overnight. The resulting hydrochloride salt was added to a suspension of 10% Pd/C (800 mg) in methanol (250 mL). The reaction was then stirred under hydrogen (1 atmosphere of pressure) for 50 min. The mixture was filtered through Celite® and the filtrate was concentrated in vacuo. The resulting residue was partitioned with saturated $NaHCO_3$ (100 mL) and $CH_2Cl_2$ (200 mL). The organic layer was dried ($Na_2SO_4$), filtered and concentrated ill vacuo to give the crude product. Flash chromatography on silica gel eluting with a gradient of $CH_2Cl_2$:CMA (4:1 to 2:1) gave 2.02 g (43%) of the title compound.

Mp 44–46° C.

$^1$H NMR (300 MHz, $CDCl_3$) δ 7.40 (d, J=8.7 Hz, 2H), 6.91 (br. s, 1H), 6.53 (d, J=8.7 Hz, 2H), 3.11–3.43 (m, 6H), 3.03 (d, 2H), 2.70 (d, 2H), 2.38–2.51 (m, 2H), 1.58–2.22(m, 4H)

$^{13}$C NMR (mixture of conformers, 75 MHz, $CDCl_3$) δ 162.1, 152.0, 133.7, 133.3, 120.9, 111.9, 97.5, 60.3, 60.0, 59.2, 57.4, 53.0, 52.4, 51.7, 50.6, 43.5, 26.0, 25.0

MS (CI): 271 m/z $(M+H)^+$

Preparation E

4-[4-(3,8-Diazabicyclo[3.2.1]oct-8-yl)-1-(3,4-dimethoxyphenoxy)butyl]benzonitrile (a) 4-[1-(3,4-Dimethoxyphenoxy)-3-butenyl]benzonitrile A cooled (0° C.) mixture of 4-(1-hydroxy-3-butenyl)benzonitrile (14.6 g, 84.3 mmol) and 3,4-dimethoxyphenol (19.5 g, 125.4 mmol) in toluene (500 mL) was treated with tributylphosphine (32.14 mL of 97% purity, 25.6 g, 126.4 mmol), followed by 1,1'-(azodicarbonyl)dipiperidine (31.8 g, 126.4 mmol). After addition was complete, the reaction mixture thickened and the temperature rose to 15° C. Additional toluene was added (500 mL), and the mixture stirred at rt overnight. The precipitate of tributylphosphine oxide was then removed by filtration and the filtrate concentrated ill vacuo to give 65.8 g of crude product. This was purified by chromatography on silica gel, eluting with toluene:methanol (98:2), to yield 17.9 g of the sub-title compound.

(b) 4-[1-(3,4-Dimethoxyphenoxy)-4-hydroxybutyl]benzonitrile

Borane-methyl sulfide complex (2 M in ether, 11 mL, 22 mmol) was added dropwise to a cooled (−5° C.) solution of 4-[1-(3,4-dimethoxyphenoxy)-3-butenyl]benzonitrile (from step (a) above; 17.6 g, 56.8 mmol) in dry THF (15 mL) over a period of 15 minutes (during which time the reaction temperature rose to 0° C.). The resulting mixture was stirred at between 0 and 10° C. for 1.5 h, before being allowed to warm to rt. Stirring was continued for a further 3.5 h at this temperature before water (22 mL) and sodium perborate tetrahydrate (11 g, 66 mmol) were added. The biphasic mixture was stirred for 2 h at rt before the water layer was separated and extracted with ether. The combined organic layers were washed with brine, dried and concentrated in vacuo. The resulting residue was purified by chromatography on silica gel, eluting with IPA:ethyl acetate:heptane (5:25:70) to yield 14.5 g (77%) of the sub-title compound.

(c) 4-(4-Cyanophenyl)-4-(3,4-dimethoxyphenoxy)butyl methanesulfonate

A solution of methanesulfonyl chloride (3.4 mL, 5.0 g, 44 mmol) in DCM (15 mL) was added slowly to a cooled (−5° C.) mixture of 4-[1-(3,4-dimethoxyphenoxy)-4-hydroxybutyl]benzonitrile (from step (b) above; 11 g, 34 mmol) and triethylamine (7 mL, 5.2 g, 50.6 mmol) in DCM (50 mL), during which addition the temperature did not rise above 2° C. Stirring was continued at between 0 and 5° C. for a further 2 h before water was added. The resulting organic layer was separated, and washed with water, separated again and then dried to give the sub-title compound in 100% yield.

(d) 4-[4-(3-Benzyl-3,8-diazabicyclo[3.2.1]oct-8-yl)-1-(3,4-dimethoxyphenoxy)butyl]benzonitrile To a solution of 3-benzyl-3,8-diazabicyclo[3.2.1]octane (5.0 g, 24.7 mmol; from Preparation B, step (e) above) in DMF (150 mL) was added $K_2CO_3$ (3.7 g, 27.2 mmol) and 4-(4-cyanophenyl)-4-(3,4-dimethoxyphenoxy)butyl methanesulfonate (10.0 g, 24.7 mmol; see step (c) above). The resulting solution was warmed to 80° C., stirred for 18 h, cooled and concentrated in vacuo. The residue was suspended in $H_2O$ and extracted with $CH_2Cl_2$ (3×). The combined organics were dried ($Na_2SO_4$), filtered and concentrated in vacuo to give an oil. Flash chromatography on silica gel eluting with $CH_2Cl_2$:MeOH (95:5) then with EtOAc:MeOH (9:1) gave 10.2 g of an oil. The oil was dissolved in $CH_3CN$ (300 mL), acidified with concentrated HCl (4.2 mL, 49.8 mmol), concentrated in vacuo and dried to afford 11.5 g (90%) of the sub-title compound.

$^1$H NMR (300 MHz, $CD_3OD$) δ 7.42–7.73 (m, 9H), 6.72 (d, 1H, J=8 Hz), 6.62 (d, 1H, J=2 Hz), 6.33 (dd, 1H, J=2 Hz, J=8 Hz), 5.35 (br s, 1H), 4.34–4.42 (m, 2H), 4.24–4.33 (m, 2H), 3.75 (s, 3H), 3.69 (s, 3H), 3.67–3.85 (m, 2H), 3.47–3.61 (m, 2H), 3.12–3.28 (m, 2H), 2.31–2.49 (m, 4H), 1.85–2.18 (m, 4H).

(e) 4-[4-(3,8-Diazabicyclo[3.2.1]oct-8-yl)-1-(3,4-dimethoxyphenoxy)butyl]benzonitrile To a solution of 4-[4-(3-benzyl-3,8-diazabicyclo[3.2.1]oct-8-yl)-1-(3,4-dimethoxyphenoxy)butyl]benzonitrile (9.2 g, 15.7 mmol; from step (d) above) in MeOH (1000 mL) was added 10% Pd/C (2.8 g) under a blanket of $N_2$. The resulting solution was purged with $H_2$ then stirred under a $H_2$ atmosphere for 2 h. The solution was filtered through Celite® and the filtrate concentrated in vacuo to give a crushable foam. Flash chromatography on silica gel eluting first with $CH_2Cl_2$:MeOH:concentrated $NH_4OH$ (188:10:2 to 177:20:3 gradient) then a second flash chromatography with $CHCl_3$:

MeOH:AcOH (90:10:1 to 85:10:5 to 50:45:5 gradient) gave the AcOH salt of the title compound. The AcOH salt was neutralized with aqueous NaHCO$_3$ and extracted with CH$_2$Cl$_2$ (3×). The combined organics were dried (Na$_2$SO$_4$), filtered and concentrated in vacuo to afford 3.2 g (48%) of the title compound.

Mp 38–43° C.

$^1$H NMR (300 MHz, CDCl$_3$) δ 7.61–7.67 (d, 2H, J=8 Hz), 7.43–7.49 (d, 2H, J=8 Hz), 6.64 (d, 1H, J=8 Hz), 6.49 (d, 1H, J=2 Hz), 6.17 (dd, 1H, J=2 Hz, J=8 Hz), 5.13 (m, 1H), 3.84 (s, 3H), 3.77 (s, 3H), 2.88–3.18 (m, 4H), 2.58–2.69 (m, 2H), 2.25–2.36 (t, 2H, J=7 Hz), 1.52–2.08 (m, 9H).

$^{13}$C NMR (75 MHz, CDCl$_3$) δ 152.3, 150.0, 148.0, 144.0, 132.6, 126.9, 118.9, 111.8, 111.5, 105.7, 102.1, 79.9, 60.2, 56.5, 56.0, 53.3, 51.7, 36.3, 25.2, 24.5.

MS (CI): 422 m/z (M+H)$^+$

Preparation F

4-[3-(3,8-Diazabicyclo[3.2.1]oct-3-yl)-2-hydroxy propoxy]benzonitrile (a) tert-Butyl 3-[3-(4-cyanophenoxy)-2-hydroxypropyl]-3,8-diazabicyclo[3.2.1]octane-8-carboxylate To a solution of tert-butyl 3,8-diazabicyclo[3.2.1]octane-8-carboxylate (3.08 g, 14.5 mmol; from Preparation B above) in 2-propanol (200 mL) was added H$_2$O (20 mL) and 4-(2-oxiranylmethoxy)benzonitrile (2.54 g, 14.5 mmol; prepared as described in international patent application WO 99/31100). The resulting solution was warmed to 75° C., stirred for 18 h, cooled and concentrated in vacuo. Flash chromatography of the residue on silica gel eluting with CH$_2$Cl$_2$:EtOAc (3:1 to 2:1 gradient) gave 3.86 g (69%) of the sub-title compound.

Mp 98–104° C.

$^1$H NMR (300 MHz, CDCl$_3$) δ 7.58–7.62 (d, 2H, J=9 Hz), 6.95–7.02 (d, 2H, J=9 Hz), 3.96–4.32 (m, 6H), 3.52 (br s, 1H), 2.78 (dd, 1H, J=2 Hz, J=7 Hz), 2.45–2.67 (m, 4H), 2.33 (br s, 1H), 1.67–1.96 (m, 3H), 1.48 (s, 9H).

$^{13}$C NMR (75 MHz, CDCl$_3$) δ 162.2, 153.8, 134.2, 119.3, 115.5, 104.6, 79.8, 70.7, 65.5, 59.6, 56.9, 54.0, 28.7.

MS (CI): 388 m/z (M+H)$^+$ (b) 4-[3-(3,8-Diazabicyclo[3.2.1]oct-3-yl)-2-hydroxypropoxy]benzonitrile To a solution of tert-butyl 3-[3-(4-cyanophenoxy)-2-hydroxypropyl]-3,8-diazabicyclo[3.2.1]octane-8-carboxylate (3.86 g, 9.96 mmol; from step (a) above) in EtOAc (100 mL) was added HCl/EtOAc (150 mL). The resulting solution was stirred for 2 h and concentrated in vacuo to give a foam. The crude product was neutralised with aqueous NaHCO$_3$, extracted with CH$_2$Cl$_2$ (3×), dried (Na$_2$SO$_4$), filtered and concentrated in vacuo. Flash chromatography of the residue on silica gel eluting with CH$_2$Cl$_2$:MeOH:concentrated NH$_4$OH (177:20:3) gave 1.82 g (64%) of the title compound as a solid.

Mp 115–119° C.

R$_f$ 0.30 (CH$_2$Cl$_2$, MeOH, concentrated NH$_4$OH (177:20:3))

$^1$H NMR (300 MHz, CDCl$_3$) δ 7.53–7.67 (d, 2H, J=9 Hz), 6.93–7.08 (d, 2H, J=9 Hz), 3.93–4.18 (m, 3H), 3.38–3.85 (m, 3H), 2.82 (d, 1H, J=9 Hz), 2.38–2.75 (m, 4H), 2.25 (d, 1H, J=9 Hz), 1.53–2.02 (m, 5H).

$^{13}$C NMR (75 MHz, CDCl$_3$) δ 162.2, 134.1, 119.2, 115.4, 104.3, 70.8, 65.2, 61.7, 59.9, 59.0, 55.1, 54.6, 29.5, 29.3.

MS (CI): 288 m/z (M+H)$^+$

Preparation G

4-{[3-(3,8-Diazabicyclo[3.2.1]oct-3-yl)propyl]amino}benzonitrile (a) tert-Butyl 3-[3-(4-cyanoanilino)propyl]-3,8-diazabicyclo[3.2.1]octane-8-carboxylate To a solution of tert-butyl 3,8-diazabicyclo[3.2.1]octane-8-carboxylate (3.5 g, 16.5 mmol; from Preparation B above) in DMF (75 mL) was added K$_2$CO$_3$ and 3-(4-cyanoanilino)propyl 4-methylbenzenesulfonate (5.5 g, 16.5 mmol; from Preparation D, step (b) above). The resulting solution was warmed to 90° C., stirred for 5 h, cooled and concentrated in vacuo. The residue was suspended in H$_2$O and extracted with CH$_2$Cl$_2$ (3×). The combined organics were dried (Na$_2$SO$_4$), filtered and concentrated in vacuo to give an oil. Flash chromatography on silica gel eluting with CH$_2$Cl$_2$:EtOAc (3:1) gave 4.7 g (77%) of the title compound as a solid.

Mp 124–127° C.

$^1$H NMR (300 MHz, CDCl$_3$) δ 7.38–7.47 (d, 2H, J=9 Hz), 6.50–6.58 (d, 2H, J=9 Hz), 5.63 (br s, 1 h), 4.08–4.33 (m, 2H), 3.17–3.28 (m, 2H), 2.72–2.80 (d, 2H, J=9 Hz), 2.43–2.54 (t, 2H, J=3 Hz), 2.15–2.35 (m, 2H), 1.72–2.03 (m, 6H), 1.45 (s, 9H).

$^{13}$C NMR (75 MHz, CDCl$_3$) δ 153.7, 151.9, 133.8, 120.8, 112.0, 98.1, 79.6, 58.4, 56.8, 54.4, 53.6, 43.1, 28.6, 24.8.

MS (CI): 371 m/z (M+H)$^+$ (b) 4-{[3-(3,8-Diazabicyclo[3.2.1]oct-3-yl)propyl]amino}benzonitrile To a solution of tert-butyl 3-[3-(4-cyanoanilino)propyl]-3,8-diazabicyclo[3.2.1]octane-8-carboxylate (4.7 g, 2.7 mmol; from step (a) above) in CH$_2$Cl$_2$ (600 mL) was added TFA (90 mL). The resulting solution was stirred for 1 h and concentrated in vacuo. Flash chromatography on silica gel eluting with CH$_2$Cl$_2$:MeOH:concentrated NH$_4$OH (94:5:1) gave 2.7 g (79%) of the title compound as an oil.

$^1$H NMR (300 MHz, CDCl$_3$) δ 7.36–7.47 (d, 2H, J=8 Hz), 6.52–6.60 (d, 2H, J=8 Hz), 5.84 (br s, 1H), 3.52–3.63 (m, 2H), 3.15–3.38 (m, 4H), 2.72–2.88 (m, 2H), 2.43–2.57 (m, 2H), 2.17–2.31 (m, 2H), 1.69–1.97 (m, 5H).

$^{13}$C NMR (75 MHz, CDCl$_3$) δ 152.0, 133.9, 133.5, 120.8, 112.0, 98.2, 60.1, 58.2, 57.4, 54.9, 44.0, 43.5, 29.0, 26.6, 24.5.

MS (CI): 271 m/z (M+H)$^+$

Preparation H

4-[4-(3,8-Diazabicyclo[3.2.1]oct-3-yl)-1-(3,4-dimethoxyphenoxy)butyl]benzonitrile (a) tert-Butyl 3-[4-(4-cyanophenyl)-4-(3,4-dimethoxyphenoxy)butyl]-3,8-diazabicyclo[3.2.1]octane-8-carboxylate To a solution of tert-butyl 3,8-diazabicyclo[3.2.1]octane-8-carboxylate (7.1 g, 33.4 mmol; from Preparation B above) in DMF (120 mL) was added K$_2$CO$_3$ (5.1 g, 36.8 mmol) and 4-(4-cyanophenyl)-4-(3,4-dimethoxyphenoxy)butyl methanesulfonate (13.9 g, 34.4 mmol; see Preparation E, step (c) above). The resulting solution was heated to 90° C., stirred 4 h, cooled and concentrated in vacuo. The residue was suspended in H$_2$O and extracted with CH$_2$Cl$_2$ (3×). The combined organics were dried (Na$_2$SO$_4$), filtered and concentrated in vacuo. Flash chromatography on silica gel eluting with CH$_2$Cl$_2$:MeOH (98:2) gave 17.3 g (99%) of the title compound.

Mp 38–41° C.

$^1$H NMR (300 MHz, CDCl$_3$) δ 7.60–7.68 (d, 2H, J=8 Hz), 7.43–7.51 (d, 2H, J=8 Hz), 6.64 (d, 1H, J=8 Hz), 6.50 (d, 1H, J=2 Hz), 6.27 (dd, 1H, J=2 Hz, J=8 Hz), 5.08 (t, 1H, J=3 Hz), 4.02–4.27 (m, 2H), 3.83 (s, 3H), 3.78 (s, 3H), 2.52–2.64 (t, 2H, J=5 Hz), 2.08–2.48 (m, 4H), 1.74–2.05 (m, 5H), 1.45 (s, 9H), 1.38–1.73 (m, 3H).

$^{13}$C NMR (75 MHz, CDCl$_3$) δ 153.6, 152.1, 149.8, 147.9, 143.7, 132.4, 126.6, 118.6, 111.7, 111.3, 105.5, 101.9, 79.6, 79.1, 57.9, 56.7, 56.3, 55.8, 54.4, 53.6, 35.7, 28.4, 27.7, 22.5.

MS (CI): 522 m/z (M+H)$^+$ (b) 4-[4-(3,8-Diazabicyclo[3.2.1]oct-3-yl)-1-(3,4-dimethoxyphenoxy)butyl]benzonitrile To a solution of tert-butyl 3-[4-(4-cyanophenyl)-4-(3,4-dimethoxyphenoxy)butyl]-3,8-diazabicyclo[3.2.1]octane-8-carboxylate (17.3 g, 33.2 mmol; from step (a) above) in CH$_2$Cl$_2$ (600 mL) was added TFA (130 mL). The resulting solution was stirred for 30 min then concentrated in vacuo. The residue was neutralized with aqueous Na$_2$CO$_3$, extracted with CH$_2$Cl$_2$ (3×), dried (Na$_2$SO$_4$), filtered and concentrated in vacuo to give an oil. Flash chromatography on silica gel eluting with CH$_2$Cl$_2$:MeOH:concentrated NH$_4$OH (177:20:3) gave 5.0 g (36%) of the title compound as an oil.

$^1$H NMR (300 MHz, CDCl$_3$) δ 7.61–7.67 (d, 2H, J=8 Hz), 7.43–7.49 (d, 2H, J=8 Hz), 6.65 (d, 1H, J=8 Hz), 6.49 (d, 1H, J=2 Hz), 6.17 (dd, 1H, J=2 Hz, J=8 Hz), 5.08 (m, 1H), 3.84 (s, 3H), 3.78 (s, 3H), 3.35–3.47 (m, 2H), 2.58–2.67 (t, 2H, J=7 Hz), 2.25–2.36 (m, 2H), 2.06–2.17 (m, 2H), 1.43–2.05 (m, 9H).

$^{13}$C NMR (75 MHz, CDCl$_3$) δ 152.3, 150.0, 148.1, 143.9, 132.6, 126.8, 118.8, 111.8, 111.4, 105.6, 102.1, 79.9, 60.5, 60.2, 57.3, 56.4, 55.9, 54.9, 35.9, 29.3, 22.5.

MS (CI): 422 m/z (M+H)$^+$

Preparation I

4-[2-(3,8-Diazabicyclo[3.2.1]oct-8-yl)ethoxy]benzonitrile (a) 4-(2-Bromoethoxy)benzonitrile A mixture of 4-cyanophenol (35.7 g, 0.3 mol), K$_2$CO$_3$ (41.4 g, 0.3 mol) and 1,2-dibromoethane (561 g, 3.0 mol) in MeCN (450 mL) was stirred under reflux overnight. The mixture was filtered and evaporated to give 30.2 g (45%) of the sub-title compound, which was used without further purification.

(b) tert-Butyl 8-[2-(4-cyanophenoxy)ethyl]-3,8-diazabicyclo[3.2.1]octane-3-carboxylate tert-Butyl 3,8-diazabicyclo[3.2.1]octane-3-carboxylate hydrochloride (1.36 g, 5.5 mmol; see Preparation A) was dissolved in H$_2$O/CHCl$_3$/saturated K$_2$CO$_3$ solution (40:40:5) and the resulting mixture was shaken. The phases were separated, dried and evaporated giving 1.1 g (100%), of the free base. Acetonitrile (100 mL), 4-(2-bromoethoxy)benzonitrile (1.49 g, 6.6 mmol; from step (a) above) and K$_2$CO$_3$ (2.4 g, 17.5 mmol) were added. The mixture was stirred at 70° C. for 24 h, the solids were filtered off and the residue evaporated and purified by chromatography on silica, eluting with CHCl$_3$:MeOH (95:5), to give 1.5 g (4.3 mmol) of the sub-title compound.

(c) 4-[2-(3,8-Diazabicyclo[3.2.1]oct-8-yl)ethoxy]benzonitrile tert-Butyl 8-[2-(4-Cyanophenoxy)ethyl]-3,8-diazabicyclo[3.2.1]octane-3-carboxylate (1.35 g, 3.8 mmol; from step (b) above) was dissolved in ethyl acetate (30 mL). The solution was cooled to 0° C., ethyl acetate (30 mL) saturated with gaseous HCl was added, and the resulting mixture stirred at r.t for 15 h. The solvent was evaporated before CHCl$_3$ was added. The mixture was extracted with K$_2$CO$_3$ solution, separated, dried and evaporated to give 0.7 g (73%) of the title compound.

MS (ES): 258 m/z (M+H)$^+$

Preparation J

4-[2-(3,8-Diazabicyclo[3.2.1]oct-8-yl)ethoxy]isophthalonitrile (a) 4-(2-Bromoethoxy)isophthalonitrile The sub-title compound was prepared in 64% yield according to the procedure described in Preparation I, step (a) above, using 4-hydroxyisophthalonitrile in place of 4-cyanophenol.

(b) tert-Butyl 8-[2-(2,4-dicyanophenoxy)ethyl]-3,8-diazabicyclo[3.2.1]octane-3-carboxylate tert-Butyl 3,8-diazabicyclo[3.2.1]octane-3-carboxylate hydrochloride (1.0 g, 4.1 mmol; from Preparation A above) was dissolved in H$_2$O/CHCl$_3$ (30 mL of 1:2). Saturated K$_2$CO$_3$ solution (5 mL) was added and the resulting mixture was shaken. The phases were separated, dried and evaporated to give 0.9 g (100%) of the free base.

The free base (0.9 g, 4.1 mmol) was dissolved in CH$_3$CN (50 mL) and 4-(2-bromoethoxy)isophthalonitrile (1.17 g, 4.7 mmol; from step (a) above) and K$_2$CO$_3$ (0.93 g, 6.75 mmol) were added. The mixture was stirred at 70° C. for 6 h, the solids were filtered off and the residue was evaporated and purified by column chromatography (CHCl$_3$:MeOH, 95:5) to give the sub-title compound in 84% yield.

(c) 4-[2-(3,8-Diazabicyclo[3.2.1]oct-8-yl)ethoxy]isophthalonitrile

The title compound was prepared in 73% yield according to the method described in Preparation I, step (c) above, using tert-butyl 8-[2-(2,4-dicyanophenoxy)ethyl]-3,8-diazabicyclo[3.2.1]octane-3-carboxylate (from step (b) above) in place of tert-butyl 8-[2-(4-cyanophenoxy)ethyl]-3,8-diazabicyclo[3.2.1]octane-3-carboxylate.

MS (ES): 283 m/z (M+H)$^+$ $^{13}$C NMR (75 MHz, CDCl$_3$) δ 163.3, 137.9, 137.4, 116.9, 114.1, 113.3, 104.8, 103.7, 70.4, 61.8, 52.6, 51.9, 25.3.

Preparation K

4-[4-(3,8-Diazabicyclo[3.2.1]oct-8-yl)-1-(4-hydroxyphenoxy)butyl]benzonitrile (a) 4-(1-{[1-(tert-Butyl)-1,1-dimethylsilyl]oxy}-3-butenyl)benzonitrile Imidazole (11.5 g, 170 mmol) and tert-butyldimethylsilyl chloride (12 g, 80 mmol) were added to a stirred solution of 1-(p-cyanophenyl)-3-buten-1-ol (11.5 g, 87 mmol) in DMF (50 mL), and the reaction mixture was stirred under an inert atmosphere (N$_2$) for 10 h. The solvent was then evaporated and the residue partitioned between water and diethyl ether. The organic layer was separated, dried, concentrated and subjected to column chromatography (CH$_2$Cl$_2$) to give the sub-title compound in a 86% yield.

(b) 4-(1-{[1-(tert-Butyl)-1,1-dimethylsilyl]oxy}-4-hydroxybutyl)benzonitrile

Borane-methyl sulfide complex (13 mL, 2 M, 26 mmol) was added to a cooled (0° C.), stirred solution of 4-(1-{[1-(tert-butyl)-1,1-dimethylsilyl]oxy}-3-butenyl)benzonitrile (15.2 g, 53 mmol; from step (a) above) in THF (100 mL). After addition was complete, the reaction was allowed to warm to rt, and stirring was continued until all of the starting material was consumed (as indicated by tlc). The temperature was then lowered to 0° C. again, and an aqueous solution of sodium perborate tetrahydrate (19 g, 123 mmol in 55 mL) was added. The reaction mixture was stirred for a further 12 h at rt before brine (100 mL) and diethyl ether (150 mL) were added. The organic layer was then separated, dried, concentrated and subjected to column chromatography (hexane:EtOAc; 1:1) to give the title compound in 85% yield.

(c) 4-{[1-(tert-Butyl)-1,1-dimethylsilyl]oxy}-4-(4-cyanophenyl)butyl methanesulfonate Methanesulfonyl chloride (7.9 g, 69 mmol) and triethylamine (10.3 g, 102 mmol) were added to a cooled (0° C.), stirred solution of 4-(1-{[1-(tert-butyl)-1,1-dimethylsilyl]oxy}-4-hydroxybutyl)benzonitrile (20.8 g, 69 mmol; from step (b) above) in $CH_2Cl_2$ (200 mL). The reaction was allowed to warm to rt until all of the starting material was consumed (as indicated by tlc). Water (200 mL) was added and the organic layer was separated, dried and concentrated to give the title compound in 98% yield.

(d) 4-{1-[4-(Tetrahydro-2H-pyran-2-yloxy)phenoxy]-3-butenyl}benzonitrile 4-(Tetrahydro-2H-pyran-2-yloxy)phenol (19.0 g, 0.1 mol) and 4-(1-hydroxy-3-butenyl)benzonitrile (17.8 g, 0.1 mol) was mixed in toluene, and cooled to 0° C. (under nitrogen). TBP (22.9 g, 0.11 mol) was added, followed by ADDP. The mixture was stirred at rt overnight, filtered, and evaporated. Purification by chromatography on silica gave 24 g (68.7%) of the desired compound.

(e) 4-{4-Hydroxy-1-[4-(tetrahydro-2H-pyran-2-yloxy)phenoxy]butyl}benzonitrile

4-{1-[4-(Tetrahydro-2H-pyran-2-yloxy)phenoxy]-3-butenyl}benzonitrile (4.6 g, 13 mmol; from step (d) above) was dissolved in dry THF (50 mL) under argon and cooled to −5° C. Borane-methylsulfide complex ($BH_3 \times SMe_2$) (3.5 mL of a 2 M solution in ether) was added dropwise at 0 to 5° C. The mixture was stirred at that temperature for 1.5 h. After 4 h at rt, tlc showed that the reaction was complete. The reaction mixture was quenched with 14 mL of $H_2O$ and 5 g of $NaBO_3$. The mixture was stirred overnight, the solvent decanted off, and the residue treated with ether and decanted. The combined organic fractions were washed with brine, dried ($Na_2SO_4$), and evaporated. The crude product was purified by chromatography on silica (iso-propanol:ethyl acetate:heptane; 5:20:70). Yield: 2.44 g (58%).

(f) 4-(4-Cyanophenyl)-4-[4-(tetrahydro-2H-pyran-2-yloxy)phenoxy]butyl methanesulfonate The sub-title compound was prepared in quantitative yield from 4-{4-hydroxy-1-[4-(tetrahydro-2H-pyran-2-yloxy)phenoxy]butyl}benzonitrile (from step (e) above) according to the procedure described in step (c) above.

(g) tert-Butyl 8-{4-(4-cyanophenyl)-4-[4-(tetrahydro-2H-pyran-2-yloxy)phenoxy]butyl}-3,8-diazabicyclo[3.2.1]octane-3-carboxylate The sub-title compound was obtained in 55% yield according to the procedure described in Preparation I, step (b) above using 4-(4-cyanophenyl)-4-[4-(tetrahydro-2H-pyran-2-yloxy)phenoxy]butyl methane-sulfonate (see step (f) above) in place of 4-(2-bromoethoxy)benzonitrile.

(h) 4-[4-(3,8-Diazabicyclo[3.2.1]oct-8-yl)-1-(4-hydroxyphenoxy)butyl]benzonitrile The title compound was obtained in 100% yield according to the procedure described in Preparation I, step (c) above using tert-butyl 8-{4-(4-cyanophenyl)-4-[4-(tetrahydro-2H-pyran-2-yloxy)phenoxy]butyl}-3,8-diazabicyclo[3.2.1]octane-3-carboxylate (see step (g) above) in place of tert-butyl 8-[2-(4-cyanophenoxy)ethyl]-3,8-diazabicyclo[3.2.1]octane-3-carboxylate.

Preparation L

4-{[3-(3,8-Diazabicyclo[3.2.1]oct-8-yl)propyl]sulfonyl}benzonitrile (a) 4-[(3-Bromopropyl)sulfanyl]benzonitrile A mixture of 4-cyanothiophenol (20.8 g, 154 mmol), 1,3-dibromopropane (155 g, 0.77 mol) and $K_2CO_3$ (21.3 g, 154 mmol) in MeCN (300 mL) was refluxed overnight. Filtration and evaporation of the solvent gave a brown oil that crystallised when treated with EtOH. The crystals were isolated by filtration to give the sub-title compound (24.5 g, 62%).

(b) 4-[(3-Bromopropyl)sulfonyl]benzonitrile

3-Chloroperoxybenzoic acid (44.9 g of 70%, 182 mmol) was added slowly to a cooled (0° C.) solution of 4-[(3-bromopropyl)sulfanyl]benzonitrile (23.4 g, 91 mmol; from step (a) above) in DCM (250 mL). The mixture was then stirred at rt overnight, and the resulting precipitate filtered off. The filtrate was concentrated in vacuo to give a residue that was shown (by NMR analysis) to contain 25% sulfoxide in addition to the desired product. The residue was redissolved in DCM (250 mL), additional 3-chloroperoxybenzoic acid (5.6 g of 70%, 23 mmol) added, and the mixture stirred for 30 min. Dimethylsulfoxide (20 mmol) was added to destroy excess mCPBA before the DCM solution was washed with aqueous $NaHCO_3$, separated, dried and concentrated in vacuo. This gave the sub-title compound in 76% yield.

(c) tert-Butyl 8-{3-[(4-cyanophenyl)sulfonyl]propyl}-3,8-diazabicyclo[3.2.1]octane-3-carboxylate The sub-title compound was prepared in 95% yield according to the procedure described in Preparation I, step (b) above, using 4-[(3-bromopropyl)sulfonyl]benzonitrile (see step (b) above) in place of 4-(2-bromoethoxy)benzonitrile.

(d) 4-{[3-(3,8-Diazabicyclo[3.2.1]oct-8-yl)propyl]sulfonyl}benzonitrile

The title compound was prepared in 48% yield according to the procedure described in Preparation I, step (c) above, using tert-butyl 8-{3-[(4-cyanophenyl)sulfonyl]propyl}-3,8-diazabicyclo[3.2.1]octane-3-carboxylate (see step (c) above) in place of tert-butyl 8-[2-(4-cyanophenoxy)ethyl]-3,8-diazabicyclo[3.2.1]octane-3-carboxylate.

Preparation M tert-Butyl 3-(4-cyanophenoxy)-1-(3,8-diazabicyclo[3.2.1]oct-8-ylmethyl)propylcarbamate (a) 3-Benzyl 8-(tert-butyl) 3,8-diazabicyclo[3.2.1]octane-3,8-dicarboxylate tert-Butyl 3,8-diazabicyclo[3.2.1]octane-8-carboxylate (7.0 g, 33.0 mmol; from Preparation B above) and triethylamine (6.8 mL, 36 mmol) were dissolved in CHCl₃ (80 mL) and cooled to 0° C. N-(Benzyloxycarbonyloxy)succinimide (9.0 g, 36.1 mmol), dissolved in CHCl₃ (70 mL), was slowly added 0° C. The solution was allowed to reach r.t, and was stirred at r.t overnight. CHCl₃ (200 mL) was added and the solution was washed with water, then dried and evaporated. The residue was then dissolved in ether and washed with 2 M HCl in order to remove any remaining unreacted starting material. Drying and evaporation gave 10 g (88%) of the sub-title compound.

(b) Benzyl 3,8-diazabicyclo[3.2.1]octane-3-carboxylate

The sub-title compound was prepared in 100% yield according to the procedure described in Preparation I, step (c) above, using 3-benzyl 8-(tert-butyl) 3,8-diazabicyclo [3.2.1]octane-3,8-dicarboxylate (see step (a) above) in place of tert-butyl 8-[2-(4-cyanophenoxy)ethyl]-3,8-diazabicyclo [3.2.1]octane-3-carboxylate.

(c) 4-(3-Butenyloxy)benzonitrile

4-Cyanophenol (30 g, 250 mmol) was mixed with K₂CO₃ (72.5 g, 525 mmol) and stirred for 60 minutes. 4-Bromo-1-butene (50 g, 370 mmol) was added dropwise. The reaction mixture was stirred at 60° C. overnight. The solids were filtered off and the solvents were evaporated. The residue was dissolved in DCM. and washed with 1 N NaOH. The organic layer was separated, dried (Na₂SO₄) and evaporated to give 37 g (58%) of the sub-title compound.

(d) 4-[2-(2-Oxiranyl)ethoxy]benzonitrile 4-(3-Butenyloxy)benzonitrile (37 g, 0.21 mol; from step (c) above) was mixed with mCPBA (61.6 g, 0.25 mol) and DCM (700 mL) and stirred at r.t for 4 h. The reaction mixture was filtered and 2 mL of DMSO added to destroy the excess mCPBA. The mixture was washed with NaHCO₃, then separated, dried and evaporated to give 38.7 g (97%) of the sub-title compound.

(e) 4-(4-Amino-3-hydroxybutoxy)benzonitrile

4-[2-(2-Oxiranyl)ethoxy]benzonitrile (38.5 g, 204 mmol; from step (d) above) was mixed with NH₃ (1200 mL, conc.) and isopropanol (450 mL). The mixture was stirred at r.t for 24 h. The solid (by-product) was filtered off and the solvents were evaporated, to give 39.1 g (93%) of sub-title compound.

(f) tert-Butyl 4-(4-cyanophenoxy)-2-hydroxybutylcarbamate 4-(4-Amino-3-hydroxybutoxy)benzonitrile (34.3 g, 166 mmol; from step (e) above), was dissolved in THF:H₂O (600 mL of 8:2). Di-tert-butyl dicarbonate (36.3 g, 166 mmol) was added at 0° C. The mixture was stirred at r.t overnight before being evaporated to give 50 g (100%) of the sub-title compound. The product was used in the next step without further purification.

(g) 1-{[(tert-Butoxycarbonyl)amino]methyl}-3-(4-cyanophenoxy)propyl methanesulfonate tert-Butyl 4-(4-cyanophenoxy)-2-hydroxybutylcarbamate (38.1 g, 120 mmol; from step (f) above) and 4-(dimethylamino)pyridine (10 mol %) was dissolved in pyridine (200 mL). The mixture was cooled to 0° C. Methanesulfonyl chloride (10.7 mL, 0.136 mol) was added dropwise at 0° C. The mixture was allowed to reach r.t before the pyridine was evaporated. DCM was added, the solution was washed with 2 M HCl and water, dried and then evaporated. The compound was purified by chromatography on silica, eluting with DCM:ethyl acetate (95:5) to give 27 g of the sub-title compound.

(h) tert-Butyl 2-[2-(4-cyanophenoxy)ethyl]-1-aziridinecarboxylate

1-{[(tert-Butoxycarbonyl)amino]methyl}-3-(4-cyanophenoxy)propyl methanesulfonate (25.3 g, 0.066 mol; from step (f) above) was mixed with tetrabutylammonium hydrogensulfate (2.7 g. 7.8 mmol) and DCM (170 mL). The mixture was cooled to 0° C. and NaOH (50% (aq)) was added slowly. The mixture was then allowed to reach r.t. Water and DCM were added, the organic layer was separated and washed with water before being dried and evaporated. Yield: 19 g (99%). The product was used in the next step without further purification. (i) Benzyl 8-[2-[(tert-butoxycarbonyl)amino]-4-(4-cyanophenoxy)butyl]-3,8-diazabicyclo[3.2.1]octane-3-carboxylate tert-Butyl 2-[2-(4-cyanophenoxy)ethyl]-1-aziridinecarboxylate (1.85 g, 7.5 mmol; from step (h) above) was mixed with benzyl 3,8-diazabicyclo[3.2.1]octane-3-carboxylate (2.16 g, 7.5 mmol; from step (b) above) in isopropanol (30 mL). The mixture was stirred overnight at 60° C. Evaporation and purification by chromatography gave 1.1 g (37%) of the sub-title compound.

(j) tert-Butyl 3-(4-cyanophenoxy)-1-(3,8-diazabicyclo [3.2.1]oct-8-ylmethyl)propylcarbamate A solution of benzyl 8-[2-[(tert-butoxycarbonyl)amino]-4-(4-cyanophenoxy)butyl]-3,8-diazabicyclo[3.2.1]octane-3-carboxylate (1 g, 1.8 mmol; from step (i) above) in 95% ethanol (200 mL) was hydrogenated over 5% Pd/C at 1 atm. for 1.5 h. The mixture was filtered through a pad of Celite® and the filtrate was evaporated to give 0.7 g (97%) of the title compound.

Preparation N

Methyl (1S)-2-(4-cyanophenoxy)-1-(3,8-diazabicyclo[3.2.1]oct-8-yl-methyl)ethylcarbamate (a) 4-{[(2R)-3-Amino-2-hydroxypropyl]oxy}benzonitrile 4-[(2R)-Oxiranylmethoxy]benzonitrile (14.65 g, 83.6 mmol; prepared as described in international patent application WO 99/31100) was mixed with conc. NH₄OH (64 mL) and 87 mL of isopropanol. The mixture was stirred at r.t for 18 h. The reaction mixture was filtered and the filtrate evaporated to give 14.6 g (91%) of the sub-title compound.

(b) tert-Butyl (2R)-3-(4-cyanophenoxy)-2-hydroxypropylcarbamate

4-{[(2R)-3-Amino-2-hydroxypropyl]oxy}benzonitrile (6.8 g, 3.5 mmol; from step (a) above was dissolved in a mixture of THF/water (8:1). The solution was cooled with an ice bath before di-tert-butyl dicarbonate (7.7 g, 3.5 mmol) was added in portions. The mixture was stirred at r.t overnight, after which the solvents were evaporated and DCM was added. The resulting solution was washed with water, dried (Na₂SO₄) and evaporated to give 9.2 g of the sub-title compound.

(c) (1R)-2-[(tert-Butoxycarbonyl)amino]-1-[(4-cyanophenoxy)methyl]ethyl methanesulfonate The sub-title compound was prepared in 100% yield according to the procedure described in Preparation M, step (g) above, using tert-butyl (2R)-3-(4-cyanophenoxy)-2-hydroxypropylcarbamate (see step (b) above) in place of tert-butyl 4-(4-cyanophenoxy)-2-hydroxybutylcarbamate.

(d) tert-Butyl (2S)-2-[(4-cyanophenoxy)methyl]-1-aziridinecarboxylate

The sub-title compound was prepared according to the procedure described in Preparation M, step (h), using (1R)-2-[(tert-butoxycarbonyl)amino]-1-[(4-cyanophenoxy)methyl]ethyl methanesulfonate (see step (c) above) in place of 1-{[(tert-butoxycarbonyl)amino]methyl}-3-(4-cyanophenoxy)propyl methanesulfonate.

(e) tert-Butyl (1S)-2-(3-benzyl-3,8-diazabicyclo[3.2.1]oct-8-yl)-1-[(4-cyanophenoxy)methyl]ethylcarbamate tert-Butyl (2S)-2-[(4-cyanophenoxy)methyl]-1-aziridinecarboxylate (3 g, 11 mmol; see step (d) above) and 3-benzyl-3,8-diazabicyclo[3.2.1]octane (2.2 g, 0.011 mol; from Preparation B, step (e) above) were mixed in isopropanol (50 mL) and stirred at 60° C. for 48 h, and then at 80° C. for 2 h. The solvent was evaporated and the residue purified by chromatography, eluting with DCM/MeOH (9:1), to give the sub-title compound in 77% yield.

MS (ES): 477 m/z (M+H)$^+$ (f) 4-{[(2S)-2-Amino-3-(3-benzyl-3,8-diazabicyclo[3.2.1]oct-8-yl)propyl]oxy}benzonitrile The sub-title compound was prepared in 85% yield according to the procedure described in Preparation I, step (c) above, using tert-butyl (1S)-2-(3-benzyl-3,8-diazabicyclo[3.2.1]oct-8-yl)-[(4-cyanophenoxy)methyl]ethylcarbamate (see step (e) above) in place of tert-butyl 8-[2-(4-cyanophenoxy)ethyl]-3,8-diazabicyclo[3.2.1]octane-3-carboxylate.

(g) Methyl (1S)-2-(3-benzyl-3,8-diazabicyclo[3.2.1]oct-8-yl)-1-[(4-cyanophenoxy)methyl]ethylcarbamate 4-{[(2S)-2-Amino-3-(3-benzyl-3,8-diazabicyclo[3.2.1]oct-8-yl)propyl]oxy}benzonitrile (3.7 g, 9.8 mmol; from step (f) above) was mixed with DCM (50 mL) and triethylamine (2.1 g, 21.5 mmol). The mixture was cooled to 0° C. and methylchloroformate (0.8 mL, 10.7 mmol) was added dropwise. The reaction was performed under an argon atmosphere. After 2 h, the temperature was allowed to reach r.t, at which temperature it was then stirred overnight. Water was added, the organic layer was separated, dried and evaporated. Purification by chromatography (CHCl$_3$:MeOH (95:5)) gave 2.9 g (68%) of the sub-title compound.

(h) Methyl (1S)-2-(4-cyanophenoxy)-1-(3,8-diazabicyclo[3.2.1]oct-8-ylmethyl)ethylcarbamate Methyl (1S)-2-(3-benzyl-3,8-diazabicyclo[3.2.1]oct-8-y)-1-[(4-cyanophenoxy)methyl]ethylcarbamate (2.9 g, 6.7 mmol; from step (g) above) was mixed with MeOH (55 mL) and 1 M HCl (13 mL). The mixture was hydrogenated over 5% Pd/C. Filtration through a pad of Celite® and evaporation gave the title compound in 86% yield.

MS (FAB): 345 m/z (M+H)$^+$ $^{13}$C NMR (75 MHz, CDCl$_3$) δ 162.1, 157.0, 134.3, 119.3, 115.5, 104.5, 67.9, 66.0, 62.2, 61.9, 54.8, 52.5, 52.4, 49.7, 25.8, 25.5, 15.5.

Synthesis of Compounds of Formula I

Example 1 tert-Butyl 8-[4-(4-cyanophenyl)-4-(3,4-dimethoxyphenoxy)butyl]-3,8-diazabicyclo[3.2.1]octane-3-carboxylate To a solution of 4-[4-(3,8-diazabicyclo[3.2.1]oct-8-yl)-1-(3,4-dimethoxyphenoxy)butyl]benzonitrile (0.95 g, 2.25 mmol; see Preparation E) in THF (100 mL) was added di-tert-butyl dicarbonate (0.54 g, 2.48 mmol). The resulting solution was stirred for 2.5 h. At this point, additional di-tert-butyl dicarbonate (0.27 g, 1.24 mmol) was added and the solution was stirred for an additional 2 h before being concentrated in vacuo. Flash chromatography on silica gel, eluting with CH$_2$Cl$_2$:MeOH (95:5), then a second flash chromatography eluting with EtOAc (100%) gave 0.66 g (56%) of the title compound.

$^{13}$C NMR (75 MHz, CDCl$_3$) δ 156.0, 152.2, 149.9, 147.9, 143.8, 132.4, 126.7, 118.7, 111.7, 111.3, 105.5, 101.9, 79.7, 79.3, 58.6, 56.3, 55.8, 52.3, 50.5, 49.4, 36.1, 28.4, 25.1, 24.5.

MS (CI): 522 m/z (M+H)$^+$

Example 2

8-[2-Amino-4-(4-cyanophenoxy)butyl]-N-butyl-3,8-diazabicyclo[3.2.1]octane-3-carboxamide tert-Butyl 3-(4-cyanophenoxy)-1-(3,8-diazabicyclo[3.2.1]oct-8-ylmethyl)propylcarbamate (100.1 mg, 0.25 mmol; see Preparation M) was dissolved in MeCN (2.5 mL) and triethylamine (37.9 mg, 0.38 mmol). Butylisocyanate (29.7 mg, 0.3 mmol) was added and the reaction mixture was stirred at r.t for 4 days. The solvent was evaporated and the resulting residue dissolved in ethyl acetate (0.5 mL). Ethyl acetate saturated with HCl (2 mL) was added and the mixture was stirred for 6 h. The solvent was evaporated and the residue dissolved in MeCN (2 mL). The solution was added to ion-exchange solid phase extraction plug. The plug was then eluted with DCM/MeCN (4×2 mL of 4:1) (fraction 1) followed by DCM:MeOH:Et$_3$N (4×2 mL of 8:1:1)(fraction 2). Evaporation of fraction 2 gave the title compound in quantitative yield.

MS (ES): 400 m/z (M+H)$^+$

Example 3

The following compounds were prepared, from appropriate intermediates (such as those described hereinbefore), according to or by analogy with methods described herein and/or by standard solid or solution phase combinatorial chemistry techniques (mass spectra of the compounds, where recorded, are in brackets):

benzyl 8-{3-[(4-cyanophenyl)sulfonyl]propyl}-3,8-diazabicyclo[3.2.1]octane-3-carboxylate (m/z=454);

benzyl 8-[2-(4-cyanophenoxy)ethyl]-3,8-diazabicyclo[3.2.1]octane-3-carboxylate (m/z=392);

benzyl 8-[2-amino-4-(4-cyanophenoxy)butyl]-3,8-diazabicyclo[3.2.1]octane-3-carboxylate (m/z=435);

4-{[(2S)-2-amino-3-(3-benzyl-3,8-diazabicyclo[3.2.1]oct-8-yl)propyl]oxy}benzonitrile (m/z=377);

methyl (1S)-2-(3-benzyl-3,8-diazabicyclo[3.2.1]oct-8-yl)-1-[(4-cyanophenoxy)methyl]ethylcarbamate (m/z=435);

tert-butyl 8-[(4S)-4-(4-cyanophenyl)-4-(3,4-dimethoxyphenoxy)butyl]-3,8-diazabicyclo[3.2.1]octane-3-carboxylate (m/z=522);

4-{1-(3,4-dimethoxyphenoxy)-4-[3-(ethylsulfonyl)-3,8-diazabicyclo[3.2.1]oct-8-yl]butyl}benzonitrile;

4-[1-(3,4-dimethoxyphenoxy)-4-(3-methyl-3,8-diazabicyclo[3.2.1]oct-8-yl)butyl]benzonitrile;

3-[3-(4-cyanophenoxy)-2-hydroxypropyl]-N-hexyl-3,8-diazabicyclo[3.2.1]octane-8-carboxamide (m/z=415);

4-{3-[8-(butylsulfonyl)-3,8-diazabicyclo[3.2.1]oct-3-yl]-2-hydroxy-propoxy}benzonitrile (m/z=408);

4-{3-[8-(3,3-dimethyl-2-oxobutyl)-3,8-diazabicyclo[3.2.1]oct-3-yl]-2-hydroxypropoxy}benzonitrile (m/z=386);

4-{3-[8-(3,4-dimethoxyphenethyl)-3,8-diazabicyclo[3.2.1]oct-3-yl]-2-hydroxypropoxy}benzonitrile (m/z=452);
8-[3-(4-cyanophenoxy)-2-hydroxypropyl]-N-hexyl-3,8-diazabicyclo[3.2.1]octane-3-carboxamide (m/z=415);
8-[3-(4-cyanophenoxy)-2-hydroxypropyl]-N-ethyl-3,8-diazabicyclo[3.2.1]octane-3-carboxamide (m/z=359);
4-[3-(3-butyryl-3,8-diazabicyclo[3.2.1]oct-8-yl)-2-hydroxypropoxy]benzonitrile (m/z=358);
4-{3-[3-(butylsulfonyl)-3,8-diazabicyclo[3.2.1]oct-8-yl]-2-hydroxy-propoxy}benzonitrile (m/z=408);
4-{3-[3-(3,3-dimethyl-2-oxobutyl)-3,8-diazabicyclo[3.2.1]oct-8-yl]-2-hydroxypropoxy}benzonitrile;
4-{3-[3-(3,4-dimethoxyphenethyl)-3,8-diazabicyclo[3.2.1]oct-8-yl]-2-hydroxypropoxy}benzonitrile (m/z=452);
8-[3-(4-cyanoanilino)propyl]-N-hexyl-3,8-diazabicyclo[3.2.1]octane-3-carboxamide (m/z=398);
8-[3-(4-cyanoanilino)propyl]-N-ethyl-3,8-diazabicyclo[3.2.1]octane-3-carboxamide (m/z=342);
4-{[3-(3-butyryl-3,8-diazabicyclo[3.2.1]oct-8-yl)propyl]amino}benzonitrile (m/z=341);
4-({3-[3-(butylsulfonyl)-3,8-diazabicyclo[3.2.1]oct-8-yl]propyl}amino)benzonitrile (m/z=391);
4-({3-[3-(3,3-dimethyl-2-oxobutyl)-3,8-diazabicyclo[3.2.1]oct-8-yl]propyl}amino)benzonitrile (m/z=386);
4-({3-[3-(3,4-dimethoxyphenethyl)-3,8-diazabicyclo[3.2.1]oct-8-yl]propyl}amino)benzonitrile (m/z=435);
8-[4-(4-cyanophenyl)-4-(3,4-dimethoxyphenoxy)butyl]-N-hexyl-3,8-diazabicyclo[3.2.1]octane-3-carboxamide (m/z=549);
8-[4-(4-cyanophenyl)-4-(3,4-dimethoxyphenoxy)butyl]-N-ethyl-3,8-diazabicyclo[3.2.1]octane-3-carboxamide (m/z=493);
4-[4-(3-butyryl-3,8-diazabicyclo[3.2.1]oct-8-yl)-1-(3,4-dimethoxyphenoxy)butyl]benzonitrile;
4-[4-[3-(butylsulfonyl)-3,8-diazabicyolo[3.2.1]oct-8-yl]-1-(3,4-dimethoxyphenoxy)butyl]benzonitrile (m/z=542);
4-{1-(3,4-dimethoxyphenoxy)-4-[3-(3,3-dimethyl-2-oxobutyl)-3,8-diazabicyclo[3.2.1]oct-8-yl]butyl}benzonitrile (m/z=520);
4-[4-[3-(3,4-dimethoxyphenethyl)-3,8-diazabicyclo[3.2.1]oct-8-yl]-1-(3,4-dimethoxyphenoxy)butyl]benzonitrile;
3-[3-(4-cyanoanilino)propyl]-N-hexyl-3,8-diazabicyclo[3.2.1]octane-8-carboxamide (m/z=398);
3-[3-(4-cyanoanilino)propyl]-N-ethyl-3,8-diazabicyclo[3.2.1]octane-8-carboxamide (m/z=342);
4-{[3-(8-butyryl-3,8-diazabicyclo[3.2.1]oct-3-yl)propyl]amino}benzonitrile (m/z=341);
4-({3-[8-(butylsulfonyl)-3,8-diazabicyclo[3.2.1]oct-3-yl]propyl}amino)-benzonitrile (m/z=391);
4-({3-[8-(3,3-dimethyl-2-oxobutyl)-3,8-diazabicyclo[3.2.1]oct-3-yl]propyl}amino)benzonitrile (m/z=369);
3-[4-(4-cyanophenyl)-4-(3,4-dimethoxyphenoxy)butyl]-N-hexyl-3,8-diazabicyclo[3.2.1]octane-8-carboxamide (m/z=549);
3-[4-(4-cyanophenyl)-4-(3,4-dimethoxyphenoxy)butyl]-N-ethyl-3,8-diazabicyclo[3.2.1]octane-8-carboxamide (m/z=493);
4-[4-(8-butyryl-3,8-diazabicyclo[3.2.1]oct-3-yl)-1-(3,4-dimethoxyphenoxy)butyl]benzonitrile (m/z=492);
4-[4-[8-(butylsulfonyl)-3,8-diazabicyclo[3.2.1]oct-3-yl]-1-(3,4-dimethoxyphenoxy)butyl]benzonitrile (m/z=542);
4-{1-(3,4-dimethoxyphenoxy)-4-[8-(3,3-dimethyl-2-oxobutyl)-3,8-diazabicyclo[3.2.1]oct-3-yl]butyl}benzonitrile;
8-[3-(4-cyanophenoxy)-2-hydroxypropyl]-N-(3,5-dimethyl-4-isoxazolyl)-3,8-diazabicyclo[3.2.1]octane-3-carboxamide (m/z=426);
8-[3-(4-cyanophenoxy)-2-hydroxypropyl]-N-tetrahydro-2H-pyran-2-yl-3,8-diazabicyclo[3.2.1]octane-3-carboxamide (m/z=415);
8-[3-(4-cyanophenoxy)-2-hydroxypropyl]-N-(3,4-difluorophenyl)-3,8-diazabicyclo[3.2.1]octane-3-carboxamide (m/z=443);
8-[3-(4-cyanoanilino)propyl]-N-(3,5-dimethyl-4-isoxazolyl)-3,8-diazabicyclo[3.2.1]octane-3-carboxamide (m/z=409);
N-({8-[3-(4-cyanoanilino)propyl]-3,8-diazabicyclo[3.2.1]oct-3-yl}carbonyl)-4-methylbenzenesulfonamide (m/z=466 (ES⁻));
8-[2-(4-cyanophenoxy)ethyl]-N-ethyl-3,8-diazabicyclo[3.2.1]octane-3-carboxamide (m/z=329);
8-[2-(4-cyanophenoxy)ethyl]-N-(3,5-dimethyl-4-isoxazolyl)-3,8-diazabicyclo[3.2.1]octane-3-carboxamide (m/z=396);
8-{3-[(4-cyanophenyl)sulfonyl]propyl}-N-ethyl-3,8-diazabicyclo[3.2.1]-octane-3-carboxamide (m/z=391);
N-[(8-{3-[(4-cyanophenyl)sulfonyl]propyl}-3,8-diazabicyclo[3.2.1]oct-3-yl)carbonyl]-4-methylbenzenesulfonamide (m/z=515 (ES⁻));
tert-butyl 8-[3-(4-cyanophenoxy)-2-hydroxypropyl]-3,8-diazabicyclo[3.2.1]octane-3-carboxylate (m/z=388);
tert-butyl 8-[3-(4-cyanoanilino)propyl]-3,8-diazabicyclo[3.2.1]octane-3-carboxylate (m/z=371);
tert-butyl 3-[4-(4-cyanophenyl)-4-(3,4-dimethoxyphenoxy)butyl]-3,8-diazabicyclo[3.2.1]octane-8-carboxylate (m/z=522);
4-({3-[8-(3,4-dimethoxyphenethyl)-3,8-diazabicyclo[3.2.1]oct-3-yl]propyl}amino)benzonitrile;
4-[4-[8-(3,4-dimethoxyphenethyl)-3,8-diazabicyclo[3.2.1]oct-3-yl]-1-(3,4-dimethoxyphenoxy)butyl]benzonitrile;
N-({8-[3-(4-cyanophenoxy)-2-hydroxypropyl]-3,8-diazabioyclo[3.2.1]oct-3-yl}carbonyl)-4-methylbenzenesulfonamide (m/z=483 (ES⁻));
8-[3-(4-cyanophenoxy)-2-hydroxypropyl]-N-(4-methoxyphenyl)-3,8-diazabicyclo[3.2.1]octane-3-carboxamide (m/z=437);
8-[3-(4-cyanophenoxy)-2-hydroxypropyl]-N-(cyclopropylmethyl)-3,8-diazabicyclo[3.2.1]octane-3-carboxamide (m/z=385);
8-[3-(4-cyanophenoxy)-2-hydroxypropyl]-N-isopropyl-3,8-diazabicyclo[3.2.1]octane-3-carboxamide (m/z=373);
8-[3-(4-cyanoanilino)propyl]-N-tetrahydro-2H-pyran-2-yl-3,8-diazabicyclo[3.2.1]octane-3-carboxamide (m/z=398);
8-[3-(4-cyanoanilino)propyl]-N-(cyclopropylmethyl)-3,8-diazabicyclo[3.2.1]octane-3-carboxamide (m/z=368);
8-[3-(4-cyanoanilino)propyl]-N-isopropyl-3,8-diazabicyclo[3.2.1]octane-3-carboxamide (m/z=356);
8-[3-(4-cyanoanilino)propyl]-N-(3,4-difluorophenyl)-3,8-diazabicyclo[3.2.1]octane-3-carboxamide (m/z=426);
N-butyl-8-[3-(4-cyanoanilino)propyl]-3,8-diazabicyclo[3.2.1]octane-3-carboxamide (m/z=370);
N-({8-[2-(4-cyanophenoxy)ethyl]-3,8-diazabicyclo[3.2.1]oct-3-yl}carbonyl)-4-methylbenzenesulfonamide (m/z=453(ES⁻));
8-[2-(4-cyanophenoxy)ethyl]-N-(4-methoxyphenyl)-3,8-diazabicyclo[3.2.1]octane-3-carboxamide (m/z=407);
8-[2-(4-cyanophenoxy)ethyl]-N-[4-(2,5-dioxo-2,5-dihydro-1H-pyrrol-1-yl)phenyl]-3,8-diazabicyclo[3.2.1]octane-3-carboxamide (m/z=472);
8-[2-(4-cyanophenoxy)ethyl]-N-tetrahydro-2H-pyran-2-yl-3,8-diazabicyclo[3.2.1]octane-3-carboxamide (m/z=385);
8-[2-(4-cyanophenoxy)ethyl]-N-(cyclopropylmethyl)-3,8-diazabicyclo[3.2.1]octane-3-carboxamide (m/z=355);

8-[2-(4-cyanophenoxy)ethyl]-N-isopropyl-3,8-diazabicyclo [3.2.1]octane-3-carboxamide (m/z=343);
8-[2-(4-cyanophenoxy)ethyl]-N-(3,4-difluorophenyl)-3,8-diazabicyclo[3.2.1]octane-3-carboxamide (m/z=413);
N-butyl-8-[2-(4-cyanophenoxy)ethyl]-3,8-diazabicyclo [3.2.1]octane-3-carboxamide (m/z=357);
8-{3-[(4-cyanophenyl)sulfonyl]propyl}-N-(3,5-dimethyl-4-isoxazolyl)-3,8-diazabicyclo[3.2.1]octane-3-carboxamide (m/z=458);
8-{3-[(4-cyanophenyl)sulfonyl]propyl}-N-(4-methoxyphenyl)-3,8-diazabicyclo[3.2.1]octane-3-carboxamide (m/z=469);
8-{3-[(4-cyanophenyl)sulfonyl]propyl}-N-tetrahydro-2H-pyran-2-yl-3,8-diazabicyclo[3.2.1]octane-3-carboxamide (m/z=447);
8-{3-[(4-cyanophenyl)sulfonyl]propyl}-N-(cyclopropylmethyl)-3,8-diazabicyclo[3.2.1]octane-3-carboxamide (m/z=417);
8-{3-[(4-cyanophenyl)sulfonyl]propyl}-N-isopropyl-3,8-diazabicyclo[3.2.1]octane-3-carboxamide (m/z=405);
8-{3-[(4-cyanophenyl)sulfonyl]propyl}-N-(3,4-difluorophenyl)-3,8-diazabicyclo[3.2.1]octane-3-carboxamide (m/z=475);
N-butyl-8-{3-[(4-cyanophenyl)sulfonyl]propyl}-3,8-diazabicyclo[3.2.1]octane-3-carboxamide (m/z=419);
N-[5-({8-[3-(4-cyanophenoxy)-2-hydroxypropyl]-3,8-diazabicyclo[3.2.1]oct-3-yl}sulfonyl)-4-methyl-1,3-thiazol-2-yl]acetamide (m/z=506);
4-(2-hydroxy-3-{3-[(4-nitrophenyl)sulfonyl]-3,8-diazabicyclo[3.2.1]oct-8-yl}propoxy)benzonitrile (m/z=473);
N-[4-({8-[3-(4-cyanophenoxy)-2-hydroxypropyl]-3,8-diazabicyclo[3.2.1]oct-3-yl}sulfonyl)phenyl]acetamide (m/z=485);
4-{2-hydroxy-3-[3-(isopropylsulfonyl)-3,8-diazabicyclo[3.2.1]oct-8-yl]propoxy}benzonitrile (m/z=394);
4-(3-{3-[(3,4-dimethoxyphenyl)sulfonyl]-3,8-diazabicyclo[3.2.1]oct-8-yl}-2-hydroxypropoxy)benzonitrile (m/z=488);
N-[5-({8-[3-(4-cyanoanilino)propyl]-3,8-diazabicyclo[3.2.1]oct-3-yl}sulfonyl)-4-methyl-1,3-thiazol-2-yl]acetamide (m/z=489);
4-[(3-{3-[(4-nitrophenyl)sulfonyl]-3,8-diazabicyclo[3.2.1] oct-8-yl}propyl)-amino]benzonitrile (m/z=456);
4-[(3-{3-[(3,4-dimethoxyphenyl)sulfonyl]-3,8-diazabicyclo[3.2.1]oct-8-yl}propyl)amino]benzonitrile (m/z=471);
4-[(3-{3-[(5-chloro-1,3-dimethyl-1H-pyrazol-4-yl)sulfonyl]-3,8-diazabicyclo[3.2.1]oct-8-yl}propyl)amino]benzonitrile (m/z=464);
4-[(3-{3-[(1-methyl-1H-imidazol-4-yl)sulfonyl]-3,8-diazabicyclo[3.2.1]oct-8-yl}propyl)amino]benzonitrile (m/z=415);
4-({3-[3-(ethylsulfonyl)-3,8-diazabicyclo[3.2.1]oct-8-yl] propyl}amino)benzonitrile (m/z=363);
N-[5-({8-[2-(4-cyanophenoxy)ethyl]-3,8-diazabicyclo [3.2.1]oct-3-yl}sulfonyl)-4-methyl-1,3-thiazol-2-yl]acetamide (m/z=476);
4-(2-{3-[(4-nitrophenyl)sulfonyl]-3,8-diazabicyclo[3.2.1] oct-8-yl}ethoxy)benzonitrile (m/z=443);
N-[4-({8-[2-(4-cyanophenoxy)ethyl]-3,8-diazabicyclo [3.2.1]oct-3-yl}sulfonyl)phenyl]acetamide (m/z=455);
4-{2-[3-(isopropylsulfonyl)-3,8-diazabicyclo[3.2.1]oct-8-yl]ethoxy}benzonitrile (m/z=364);
4-{2-[3-(butylsulfonyl)-3,8-diazabicyclo[3.2.1]oct-8-yl] ethoxy}benzonitrile (m/z=378);
4-(2-{3-[(3,4-dimethoxyphenyl)sulfonyl]-3,8-diazabicyclo [3.2.1]oct-8-yl}ethoxy)benzonitrile (m/z=458);
4-(2-{3-[(5-chloro-1,3-dimethyl-1H-pyrazol-4-yl)sulfonyl]-3,8-diazabicyclo[3.2.1]oct-8-yl}ethoxy)benzonitrile (m/z=450);
4-(2-{3-[(1-methyl-1H-imidazol-4-yl)sulfonyl]-3,8-diazabicyclo[3.2.1]oct-8-yl}ethoxy)benzonitrile (m/z=402);
4-{2-[3-(ethylsulfonyl)-3,8-diazabicyclo[3.2.1]oct-8-yl] ethoxy}benzonitrile (m/z=350);
N-{5-[(8-{3-[(4-cyanophenyl)sulfonyl]propyl}-3,8-diazabicyclo[3.2.1]oct-3-yl)sulfonyl]-4-methyl-1,3-thiazol-2-yl}acetamide (m/z=538);
4-[(3-{3-[(4-nitrophenyl)sulfonyl]-3,8-diazabicyclo[3.2.1] oct-8-yl}propyl)-sulfonyl]benzonitrile (m/z=505);
N-{4-[(8-{3-[(4-cyanophenyl)sulfonyl]propyl}-3,8-diazabicyclo[3.2.1]oct-3-yl)sulfonyl]phenyl}acetamide (m/z=517);
4-({3-[3-(isopropylsulfonyl)-3,8-diazabicyclo[3.2.1]oct-8-yl]propyl}sulfonyl)benzonitrile (m/z=426);
4-({3-[3-(butylsulfonyl)-3,8-diazabicyclo[3.2.1]oct-8-yl] propyl}sulfonyl)benzonitrile (m/z=440);
4-[(3-{3-[(3,4-dimethoxyphenyl)sulfonyl]-3,8-diazabicyclo [3.2.1]oct-8-yl}propyl)sulfonyl]benzonitrile (m/z=520);
4-[(3-{3-[(5-chloro-1,3-dimethyl-1H-pyrazol-4-yl)sulfonyl]-3,8-diazabicyclo[3.2.1]oct-8-yl}propyl)sulfonyl] benzonitrile (m/z=512);
4-[(3-{3-[(1-methyl-1H-imidazol-4-yl)sulfonyl]-3,8-diazabicyclo[3.2.1]oct-8-yl}propyl)sulfonyl]benzonitrile (m/z=464);
4-({3-[3-(ethylsulfonyl)-3,8-diazabicyclo[3.2.1]oct-8-yl] propyl}sulfonyl)-benzonitrile (m/z=412);
1-cyano-1-methylethyl 8-[4-(4-cyanophenyl)-4-(3,4-dimethoxyphenoxy)butyl]-3,8-diazabicyclo[3.2.1]octane-3-carboxylate (m/z=533);
3-(methylsulfonyl)propyl 8-[4-(4-cyanophenyl)-4-(3,4-dimethoxyphenoxy)-butyl]-3,8-diazabicyclo[3.2.1]octane-3-carboxylate (m/z=586);
2-butynyl 8-[4-(4-cyanophenyl)-4-(3,4-dimethoxyphenoxy)butyl]-3,8-diazabicyclo[3.2.1]octane-3-carboxylate (m/z=518);
methyl 8-[4-(4-cyanophenyl)-4-(3,4-dimethoxyphenoxy)butyl]-3,8-diazabicyclo[3.2.1]octane-3-carboxylate (m/z=480);
2-methoxyethyl 8-[4-(4-cyanophenyl)-4-(3,4-dimethoxyphenoxy)butyl]-3,8-diazabicyclo[3.2.1]octane-3-carboxylate (m/z=524);
8-[4-(4-cyanophenyl)-4-(3,4-dimethoxyphenoxy)butyl]-N-(3,5-dimethyl-4-isoxazolyl)-3,8-diazabicyclo[3.2.1]octane-3-carboxamide (m/z=560);
8-[4-(4-cyanophenyl)-4-(3,4-dimethoxyphenoxy)butyl]-N-tetrahydro-2H-pyran-2-yl-3,8-diazabicyclo[3.2.1]octane-3-carboxamide (m/z=549);
8-[4-(4-cyanophenyl)-4-(3,4-dimethoxyphenoxy)butyl]-N-[2-(2-methoxyethoxy)ethyl]-3,8-diazabicyclo[3.2.1]octane-3-carboxamide (m/z=567);
8-[4-(4-cyanophenyl)-4-(3,4-dimethoxyphenoxy)butyl]-N-isopropyl-3,8-diazabicyclo[3.2.1]octane-3-carboxamide (m/z=507);
8-[4-(4-cyanophenyl)-4-(3,4-dimethoxyphenoxy)butyl]-N-{4-[(trifluoromethyl)sulfanyl]phenyl}-3,8-diazabicyclo [3.2.1]octane-3-carboxamide (m/z=641);
N-[5-({8-[4-(4-cyanophenyl)-4-(3,4-dimethoxyphenoxy) butyl]-3,8-diazabicyclo[3.2.1]oct-3-yl}sulfonyl)-4-methyl-1,3-thiazol-2-yl]acetamide (m/z=640);
4-{1-(3,4-dimethoxyphenoxy)-4-[3-(isopropylsulfonyl)-3, 8-diazabicyclo[3.2.1]oct-8-yl]butyl}benzonitrile (m/z=529);

4-[4-{3-[(5-chloro-1,3-dimethyl-1H-pyrazol-4-yl)sulfonyl]-3,8-diazabicyclo[3.2.1]oct-8-yl}-1-(3,4-dimethoxyphenoxy)butyl]benzonitrile (m/z=614);

4-(1-(3,4-dimethoxyphenoxy)-4-{3-[(1-methyl-1H-imidazol-4-yl)sulfonyl]-3,8-diazabicyclo[3.2.1]oct-8-yl}butyl)benzonitrile (m/z=566);

4-{1-(3,4-dimethoxyphenoxy)-4-[3-(methylsulfonyl)-3,8-diazabicyclo[3.2.1]oct-8-yl]butyl}benzonitrile (m/z=500);

4-[4-{3-[3-(4-acetyl-1-piperazinyl)propyl]-3,8-diazabicyclo[3.2.1]oct-8-yl}-1-(3,4-dimethoxyphenoxy)butyl]benzonitrile;

2-{8-[4-(4-cyanophenyl)-4-(3,4-dimethoxyphenoxy)butyl]-3,8-diazabicyclo[3.2.1]oct-3-yl}-N-isopropylacetamide (m/z=521);

4-(1-(3,4-dimethoxyphenoxy)-4-{3-[3-(ethylsulfonyl)propyl]-3,8-diazabicyclo[3.2.1]oct-8-yl}butyl)benzonitrile (m/z=556);

4-(1-(3,4-dimethoxyphenoxy)-4-{3-[2-(2-methoxyethoxy)ethyl]-3,8-diazabicyclo[3.2.1]oct-8-yl}butyl)benzonitrile (m/z=524);

4-{1-(3,4-dimethoxyphenoxy)-4-[3-(4-fluorobenzyl)-3,8-diazabicyclo[3.2.1]oct-8-yl]butyl}benzonitrile;

4-(1-(3,4-dimethoxyphenoxy)-4-{3-[2-(2,5-dioxo-4-imidazolidinyl)acetyl]-3,8-diazabicyclo[3.2.1]oct-8-yl}butyl)benzonitrile (m/z=562);

2-(acetylamino)-N-(2-{8-[4-(4-cyanophenyl)-4-(3,4-dimethoxyphenoxy)-butyl]-3,8-diazabicyclo[3.2.1]oct-3-yl}-2-oxoethyl)acetamide (m/z=578);

4-{1-(3,4-dimethoxyphenoxy)-4-[3-(2-methoxyacetyl)-3,8-diazabicyclo[3.2.1]oct-8-yl]butyl}benzonitrile (m/z=494);

4-{1-(3,4-dimethoxyphenoxy)-4-[3-(H-pyrrol-2-ylcarbonyl)-3,8-diazabicyclo[3.2.1]oct-8-yl]butyl}benzonitrile (m/z=515);

4-[1-(3,4-dimethoxyphenoxy)-4-(3-isobutyryl-3,8-diazabicyclo[3.2.1]oct-8-yl)butyl]benzonitrile (m/z=492);

ethyl 8-[3-(4-cyanophenoxy)-2-hydroxypropyl]-3,8-diazabicyclo[3.2.1]-octane-3-carboxylate (m/z=360);

2-hydroxy-1,1-dimethylethyl 8-[3-(4-cyanophenoxy)-2-hydroxypropyl]-3,8-diazabicyclo[3.2.1]octane-3-carboxylate (m/z=404);

1-cyano-1-methylethyl 8-[3-(4-cyanophenoxy)-2-hydroxypropyl]-3,8-diazabicyclo[3.2.1]octane-3-carboxylate (m/z=399);

2-butynyl 8-[3-(4-cyanophenoxy)-2-hydroxypropyl]-3,8-diazabicyclo[3.2.1]octane-3-carboxylate (m/z=384);

2-methoxyethyl 8-[3-(4-cyanophenoxy)-2-hydroxypropyl]-3,8-diazabicyclo[3.2.1]octane-3-carboxylate (m/z=390);

3-(methylsulfonyl)propyl 8-[3-(4-cyanophenoxy)-2-hydroxypropyl]-3,8-diazabicyclo[3.2.1]octane-3-carboxylate (m/z=452);

2-(4-morpholinyl)ethyl 8-[3-(4-cyanophenoxy)-2-hydroxypropyl]-3,8-diazabicyclo[3.2.1]octane-3-carboxylate (m/z=445);

2-(4-pyridinyl)ethyl 8-[3-(4-cyanophenoxy)-2-hydroxypropyl]-3,8-diazabicyclo[3.2.1]octane-3-carboxylate (m/z=437);

ethyl 8-[3-(4-cyanoanilino)propyl]-3,8-diazabicyclo[3.2.1]octane-3-carboxylate (m/z=343);

2-hydroxy-1,1-dimethylethyl 8-[3-(4-cyanoanilino)propyl]-3,8-diazabicyclo[3.2.1]octane-3-carboxylate (m/z=387);

1-cyano-1-methylethyl 8-[3-(4-cyanoanilino)propyl]-3,8-diazabicyclo[3.2.1]octane-3-carboxylate (m/z=382);

2-butynyl 8-[3-(4-cyanoanilino)propyl]-3,8-diazabicyclo[3.2.1]octane-3-carboxylate (m/z=367);

2-methoxyethyl 8-[3-(4-cyanoanilino)propyl]-3,8-diazabicyclo[3.2.1]octane-3-carboxylate (m/z=373);

3-(methylsulfonyl)propyl 8-[3-(4-cyanoanilino)propyl]-3,8-diazabicyclo[3.2.1]octane-3-carboxylate (m/z=435);

2-(4-morpholinyl)ethyl 8-[3-(4-cyanoanilino)propyl]-3,8-diazabicyclolo[3.2.1]octane-3-carboxylate (m/z=428);

2-(4-pyridinyl)ethyl 8-[3-(4-cyanoanilino)propyl]-3,8-diazabicyclo[3.2.1]octane-3-carboxylate (m/z=420);

ethyl 8-[2-(4-cyanophenoxy)ethyl]-3,8-diazabicyclo[3.2.1]octane-3-carboxylate (m/z=330);

2-hydroxy-1,1-dimethylethyl 8-[2-(4-cyanophenoxy)ethyl]-3,8-diazabicyclo[3.2.1]octane-3-carboxylate (m/z=374);

1-cyano-1-methylethyl 8-[2-(4-cyanophenoxy)ethyl]-3,8-diazabicyclo-[3.2.1]octane-3-carboxylate (m/z=369);

2-butynyl 8-[2-(4-cyanophenoxy)ethyl]-3,8-diazabicyclo[3.2.1]octane-3-carboxylate (m/z=354);

2-(4-pyridinyl)ethyl 8-[2-(4-cyanophenoxy)ethyl]-3,8-diazabicyclo[3.2.1]octane-3-carboxylate (m/z=407);

2-(4-acetyl-1-piperazinyl)ethyl 8-[2-(4-cyanophenoxy)ethyl]-3,8-diazabicyclo[3.2.1]octane-3-carboxylate (m/z=456);

ethyl 8-{3-[(4-cyanophenyl)sulfonyl]propyl}-3,8-diazabicyclo[3.2.1]octane-3-carboxylate (m/z=392);

2-hydroxy-1,1-dimethylethyl 8-{3-[(4-cyanophenyl)sulfonyl]propyl}-3,8-diazabicyclo[3.2.1]octane-3-carboxylate;

2-methoxyethyl 8-{3-[(4-cyanophenyl)sulfonyl]propyl}-3,8-diazabicyclo[3.2.1]octane-3-carboxylate (m/z=422);

3-(methylsulfonyl)propyl 8-{3-[(4-cyanophenyl)sulfonyl]propyl}-3,8-diazabicyclo[3.2.1]octane-3-carboxylate (m/z=484);

2-(4-morpholinyl)ethyl 8-{3-[(4-cyanophenyl)sulfonyl]propyl}-3,8-diazabicyclo[3.2.1]octane-3-carboxylate (m/z=477);

2-(4-pyridinyl)ethyl 8-{3-[(4-cyanophenyl)sulfonyl]propyl}-3,8-diazabicyclo[3.2.1]octane-3-carboxylate (m/z=469);

2-(4-acetyl-1-piperazinyl)ethyl 8-{3-[(4-cyanophenyl)sulfonyl]propyl}-3,8-diazabicyclo[3.2.1]octane-3-carboxylate (m/z=518);

8-{3-[(4-cyanophenyl)sulfonyl]propyl}-N-[2-(2-methoxyethoxy)ethyl]-3,8-diazabicyclo[3.2.1]octane-3-carboxamide (m/z=465);

4-(3-{3-[2-(2,5-dioxo-4-imidazolidinyl)acetyl]-3,8-diazabicyclo[3.2.1]oct-8-yl}-2-hydroxypropoxy)benzonitrile (m/z=428);

4-{2-hydroxy-3-[3-(1H-pyrrol-2-ylcarbonyl)-3,8-diazabicyclo[3.2.1]oct-8-yl]propoxy}benzonitrile (m/z=381);

4-{2-hydroxy-3-[3-(3-methylbutanoyl)-3,8-diazabicyclo[3.2.1]oct-8-yl]propoxy}benzonitrile (m/z=372);

4-{3-[3-(2,1,3-benzoxadiazol-5-ylcarbonyl)-3,8-diazabicyclo[3.2.1]oct-8-yl]-2-hydroxypropoxy}benzonitrile (m/z=434);

4-[3-(3-{[3-(tert-butyl)-1-methyl-1H-pyrazol-5-yl]carbonyl}-3,8-diazabicyclo[3.2.1]oct-8-yl)-2-hydroxypropoxy]benzonitrile (m/z=372);

4-({3-[3-(1H-pyrrol-2-ylcarbonyl)-3,8-diazabicyclo[3.2.1]oct-8-yl]propyl}amino)benzonitrile (m/z=364);

4-{[3-(3-isobutyryl-3,8-diazabicyclo[3.2.1]oct-8-yl)propyl]amino}benzonitrile;

4-({3-[3-(3-methylbutanoyl)-3,8-diazabicyclo[3.2.1]oct-8-yl]propyl}amino)benzonitrile;

4-({3-[3-(2,1,3-benzoxadiazol-5-ylcarbonyl)-3,8-diazabicyclo[3.2.1]oct-8-yl]propyl}amino)benzonitrile;

4-{[3-(3-{[3-(tert-butyl)-1-methyl-1H-pyrazol-5-yl]carbonyl}-3,8-diazabicyclo[3.2.1]oct-8-yl)propyl]amino}benzonitrile (m/z=435);

4-(2-{3-[2-(2,5-dioxo-4-imidazolidinyl)acetyl]-3,8-diazabicyclo[3.2.1]oct-8-yl}ethoxy)benzonitrile (m/z=398);
4-{2-[3-(2-methoxyacetyl)-3,8-diazabicyclo[3.2.1]oct-8-yl]ethoxy}benzonitrile (m/z=330);
4-{2-[3-(1H-pyrrol-2-ylcarbonyl)-3,8-diazabicyclo[3.2.1]oct-8-yl]ethoxy}benzonitrile (m/z=351);
4-[2-(3-isobutyryl-3,8-diazabioyclo[3.2.1]oct-8-yl)ethoxy]benzonitrile (m/z=328);
4-{2-[3-(3-methylbutanoyl)-3,8-diazabicyclo[3.2.1]oct-8-yl]ethoxy}benzonitrile (m/z=342);
4-{2-[3-(2,1,3-benzoxadiazol-5-ylcarbonyl)-3,8-diazabicyclo[3.2.1]oct-8-yl]ethoxy}benzonitrile (m/z=404);
4-[(3-{3-[2-(2,5-dioxo-4-imidazolidinyl)acetyl]-3,8-diazabicyclo[3.2.1]oct-8-yl}propyl)sulfonyl]benzonitrile (m/z=460);
4-({3-[3-(1H-pyrrol-2-ylcarbonyl)-3,8-diazabicyclo[3.2.1]oct-8-yl]propyl}sulfonyl)benzonitrile (m/z=413);
4-{[3-(3-isobutyryl-3,8-diazabicyclo[3.2.1]oct-8-yl)propyl]sulfonyl}benzonitrile (m/z=390.2);
4-({3-[3-(3-methylbutanoyl)-3,8-diazabicyclo[3.2.1]oct-8-yl]propyl}sulfonyl)benzonitrile (m/z=404);
4-({3-[3-(2,1,3-benzoxadiazol-5-ylcarbonyl)-3,8-diazabicyclo[3.2.1]oct-8-yl]propyl}sulfonyl)benzonitrile (m/z=466);
4-{[3-(3-{[3-(tert-butyl)-1-methyl-1H-pyrazol-5-yl]carbonyl}-3,8-diazabicyclo[3.2.1]oct-8-yl)propyl]sulfonyl}benzonitrile (m/z=484);
4-(3-{3-[2-(2,3-dihydro-1,4-benzodioxin-6-yl)-2-oxoethyl]-3,8-diazabicyclo[3.2.1]oct-8-yl}-2-hydroxypropoxy)benzonitrile (m/z=464);
4-{2-hydroxy-3-[3-(1,3-thiazol-2-yl)-3,8-diazabicyclo[3.2.1]oct-8-yl]propoxy}benzonitrile (m/z=371);
4-(3-{3-[3-(4-acetyl-1-piperazinyl)propyl]-3,8-diazabicyclo[3.2.1]oct-8-yl}-2-hydroxypropoxy)benzonitrile (m/z=456);
2-{8-[3-(4-cyanophenoxy)-2-hydroxypropyl]-3,8-diazabicyclo[3.2.1]oct-3-yl}-N-isopropylacetamide (m/z=387);
4-(3-{3-[3-(ethylsulfonyl)propyl]-3,8-diazabicyclo[3.2.1]oct-8-yl}-2-hydroxypropoxy)benzonitrile (m/z=422);
4-(2-hydroxy-3-{3-[2-(2-methoxyethoxy)ethyl]-3,8-diazabioyclo[3.2.1]oct-8-yl}propoxy)benzonitrile (m/z=390);
4-{3-[3-(4-fluorobenzyl)-3,8-diazabicyclo[3.2.1]oct-8-yl]-2-hydroxypropoxy}benzonitrile (m/z=396);
4-(2-hydroxy-3-{3-[2-(4-methoxyphenyl)-2-oxoethyl]-3,8-diazabicyclo[3.2.1]oct-8-yl}propoxy)benzonitrile (m/z=436);
4-({3-[3-(cyclopropylmethyl)-3,8-diazabicyclo[3.2.1]oct-8-yl]propyl}amino)benzonitrile (m/z=325);
4-[(3-{3-[2-(2,3-dihydro-1,4-benzodioxin-6-yl)-2-oxoethyl]-3,8-diazabicyclo[3.2.1]oct-8-yl}propyl)amino]benzonitrile (m/z=447);
4-({3-[3-(1,3-thiazol-2-yl)-3,8-diazabicyclo[3.2.1]oct-8-yl]propyl}amino)-benzonitrile (m/z=354);
4-[(3-{3-[3-(4-acetyl-1-piperazinyl)propyl]-3,8-diazabicyclo[3.2.1]oct-8-yl}propyl)amino]benzonitrile (m/z=439);
4-[(3-{3-[3-(ethylsulfonyl)propyl]-3,8-diazabicyclo[3.2.1]oct-8-yl}propyl)-amino]benzonitrile (m/z=405);
4-[(3-{3-[2-(2-methoxyethoxy)ethyl]-3,8-diazabicyclo[3.2.1]oct-8-yl}propyl)amino]benzonitrile (m/z=373);
4-({3-[3-(4-fluorobenzyl)-3,8-diazabicyclo[3.2.1]oct-8-yl]propyl}amino)benzonitrile (m/z=379);
4-[(3-{3-[2-(4-methoxyphenyl)-2-oxoethyl]-3,8-diazabicyclo[3.2.1]oct-8-yl}propyl)amino]benzonitrile (m/z=419);
4-{2-[3-(3,3-dimethyl-2-oxobutyl)-3,8-diazabicyclo[3.2.1]oct-8-yl]ethoxy}benzonitrile (m/z=356);
4-(2-{3-[2-(2,3-dihydro-1,4-benzodioxin-6-yl)-2-oxoethyl]-3,8-diazabicyclo[3.2.1]oct-8-yl}ethoxy)benzonitrile (m/z=434);
4-(2-{3-[3-(4-acetyl-1-piperazinyl)propyl]-3,8-diazabicyclo[3.2.1]oct-8-yl}ethoxy)benzonitrile (m/z=426);
2-{8-[2-(4-cyanophenoxy)ethyl]-3,8-diazabicyclo[3.2.1]oct-3-yl}-N-isopropylacetamide (m/z=357);
4-(2-{3-[3-(ethylsulfonyl)propyl]-3,8-diazabicyclo[3.2.1]oct-8-yl}ethoxy)benzonitrile (m/z=392);
4-(2-{3-[2-(2-methoxyethoxy)ethyl]-3,8-diazabicyclo[3.2.1]oct-8-yl}ethoxy)benzonitrile (m/z=360);
4-{2-[3-(4-fluorobenzyl)-3,8-diazabicyclo[3.2.1]oct-8-yl]ethoxy}benzonitrile (m/z=366);
4-(2-{3-[2-(4-methoxyphenyl)-2-oxoethyl]-3,8-diazabicyclo[3.2.1]oct-8-yl}ethoxy)benzonitrile (m/z=406);
4-({3-[3-(3,3-dimethyl-2-oxobutyl)-3,8-diazabicyclo[3.2.1]oct-8-yl]propyl}sulfonyl)benzonitrile (m/z=418);
4-({3-[3-(cyclopropylmethyl)-3,8-diazabicyclo[3.2.1]oct-8-yl]propyl}sulfonyl)benzonitrile (m/z=374);
4-[(3-{3-[2-(2,3-dihydro-1,4-benzodioxin-6-yl)-2-oxoethyl]-3,8-diazabicyclo[3.2.1]oct-8-yl}propyl)sulfonyl]benzonitrile (m/z=496);

2-(8-{3-[(4-cyanophenyl)sulfonyl]propyl}-3,8-diazabicyclo[3.2.1]oct-3-yl)-N-isopropylacetamide (m/z=419);

4-[(3-{3-[3-(ethylsulfonyl)propyl]-3,8-diazabicyclo[3.2.1]oct-8-yl}propyl)sulfonyl]benzonitrile (m/z=454);
4-[(3-{3-[2-(2-methoxyethoxy)ethyl]-3,8-diazabicyclo[3.2.1]oct-8-yl}propyl)sulfonyl]benzonitrile (m/z=422);
4-({3-[3-(4-fluorobenzyl)-3,8-diazabicyclo[3.2.1]oct-8-yl]propyl}sulfonyl)-benzonitrile (m/z=428);
4-[(3-{3-[2-(4-methoxyphenyl)-2-oxoethyl]-3,8-diazabicyclo[3.2.1]oct-8-yl}propyl)sulfonyl]benzonitrile (m/z=468);
4-{2-[3-(cyclopropylmethyl)-3,8-diazabicyclo[3.2.1]oct-8-yl]ethoxy}isophthalonitrile (m/z=337);
4-(2-{3-[2-(4-methyl-1,3-thiazol-5-yl)ethyl]-3,8-diazabicyclo[3.2.1]oct-8-yl}ethoxy)isophthalonitrile (m/z=408);
4-(2-{3-[3-(ethylsulfonyl)propyl]-3,8-diazabicyclo[3.2.1]oct-8-yl}ethoxy)-isophthalonitrile (m/z=417);
4-(2-{3-[2-(2-methoxyethoxy)ethyl]-3,8-diazabicyclo[3.2.1]oct-8-yl}ethoxy)isophthalonitrile (m/z=385);
4-{2-[3-(4-fluorobenzyl)-3,8-diazabicyclo[3.2.1]oct-8-yl]ethoxy}isophthalonitrile (m/z=391);
4-(2-{3-[2-(4-methoxyphenyl)-2-oxoethyl]-3,8-diazabicyclo[3.2.1]oct-8-yl}ethoxy)isophthalonitrile (m/z=431);
methyl (1S)-2-(4-cyanophenoxy)-1-{[3-(3,3-dimethyl-2-oxobutyl)-3,8-diazabicyclo[3.2.1]oct-8-yl]methyl}ethylcarbamate (m/z=443);
methyl (1S)-2-(4-cyanophenoxy)-1-{[3-(cyclopropylmethyl)-3,8-diazabicyclo[3.2.1]oct-8-yl]methyl}ethylcarbamate (m/z=399);
methyl (1S)-2-(4-cyanophenoxy)-1-({3-[2-(2,3-dihydro-1,4-benzodioxin-6-yl)-2-oxoethyl]-3,8-diazabicyclo[3.2.1]oct-8-yl}methyl)ethylcarbamate (m/z=521);
methyl (1S)-2-(4-cyanophenoxy)-1-({3-[2-(4-methyl-1,3-thiazol-5-yl)ethyl]-3,8-diazabicyclo[3.2.1]oct-8-yl}methyl)ethylcarbamate (m/z=470);
methyl (1S)-2-{3-[3-(4-acetyl-1-piperazinyl)propyl]-3,8-diazabicyclo[3.2.1]oct-8-yl}-1-[(4-cyanophenoxy)methyl]ethylcarbamate (m/z=513);
methyl (1S)-2-(4-cyanophenoxy)-1-({3-[3-(ethylsulfonyl)propyl]-3,8-diazabicyclo[3.2.1]oct-8-yl}methyl)ethylcarbamate (m/z=479);

methyl (1S)-2-(4-cyanophenoxy)-1-({3-[2-(2-methoxyethoxy)ethyl]-3,8-diazabicyclo[3.2.1]oct-8-yl}methyl)ethylcarbamate (m/z=447);
methyl (1S)-2-(4-cyanophenoxy)-1-{[3-(4-fluorobenzyl)-3,8-diazabicyclo[3.2.1]oct-8-yl]methyl}ethylcarbamate (m/z=453);
methyl (1S)-2-(4-cyanophenoxy)-1-({3-[2-(4-methoxyphenyl)-2-oxoethyl]-3,8-diazabicyclo[3.2.1]oct-8-yl}methyl)ethylcarbamate (m/z=493);
4-{3-amino-4-[3-(3,3-dimethyl-2-oxobutyl)-3,8-diazabicyclo[3.2.1]oct-8-yl]butoxy}benzonitrile (m/z=399);
4-{3-amino-4-[3-(cyclopropylmethyl)-3,8-diazabicyclo[3.2.1]oct-8-yl]butoxy}benzonitrile (m/z=355);
2-{8-[2-amino-4-(4-cyanophenoxy)butyl]-3,8-diazabicyclo[3.2.1]oct-3-yl}-N-isopropylacetamide (m/z=400);
4-(3-amino-4-{3-[3-(ethylsulfonyl)propyl]-3,8-diazabicyclo[3.2.1]oct-8-yl}butoxy)benzonitrile (m/z=435);
4-(3-amino-4-{3-[2-(2-methoxyethoxy)ethyl]-3,8-diazabicyclo[3.2.1]oct-8-yl}butoxy)benzonitrile (m/z=403);
4-{3-amino-4-[3-(4-fluorobenzyl)-3,8-diazabicyclo[3.2.1]oct-8-yl]butoxy}benzonitrile (m/z=409);
4-[4-[3-(cyclopropylmethyl)-3,8-diazabicyclo[3.2.1]oct-8-yl]-1-(4-hydroxyphenoxy)butyl]benzonitrile (m/z=432);
4-(1-(4-hydroxyphenoxy)-4-{3-[2-(4-methyl-1,3-thiazol-5-yl)ethyl]-3,8-diazabioyclo[3.2.1]oct-8-yl}butyl)benzonitrile;
4-(2-{3-[2-(2,5-dioxo-4-imidazolidinyl)acetyl]-3,8-diazabicyclo[3.2.1]oct-8-yl}ethoxy)isophthalonitrile;
4-{2-[3-(3-methylbutanoyl)-3,8-diazabicyclo[3.2.1]oct-8-yl]ethoxy}isophthalonitrile (m/z=367);
4-{2-[3-(2,1,3-benzoxadiazol-5-ylcarbonyl)-3,8-diazabicyclo[3.2.1]oct-8-yl]ethoxy}isophthalonitrile (m/z=429);
4-(2-{3-[(1-methyl-1H-indol-2-yl)carbonyl]-3,8-diazabicyclo[3.2.1]oct-8-yl}ethoxy)isophthalonitrile (m/z=440);
4-{2-[3-(ethylsulfonyl)-3,8-diazabicyclo[3.2.1]oct-8-yl]ethoxy}isophthalonitrile (m/z=375);
N-5-({8-[2-(2,4-dicyanophenoxy)ethyl]-3,8-diazabicyclo[3.2.1]oct-3-yl}sulfonyl)-4-methyl-1,3-thiazol-2-yl]acetamide (m/z=501);
4-(2-{3-[(4-nitrophenyl)sulfonyl]-3,8-diazabicyclo[3.2.1]oct-8-yl}ethoxy)isophthalonitrile (m/z=468);
4-(2-{3-[(3,4-dimethoxyphenyl)sulfonyl]-3,8-diazabicyclo[3.2.1]oct-8-yl}ethoxy)isophthalonitrile (m/z=483);
4-(2-{3-[(1-methyl-1H-imidazol-4-yl)sulfonyl]-3,8-diazabicyclo[3.2.1]oct-8-yl}ethoxy)isophthalonitrile (m/z=427);
methyl (1S)-2-(4-cyanophenoxy)-1-{[3-(3-methylbutanoyl)-3,8-diazabicyclo[3.2.1]oct-8-yl]methyl}ethylcarbamate (m/z=429);
methyl (1S)-2-[3-(2,1,3-benzoxadiazol-5-ylcarbonyl)-3,8-diazabicyclo[3.2.1]oct-8-yl]-1-[(4-cyanophenoxy)methyl]ethylcarbamate (m/z=491);
methyl (1S)-2-(4-cyanophenoxy)-1-({3-[(1-methyl-1H-indol-2-yl)carbonyl]-3,8-diazabicyclo[3.2.1]oct-8-yl}methyl)ethylcarbamate (m/z=502);
methyl (1S)-2-(4-cyanophenoxy)-1-{[3-(ethylsulfonyl)-3,8-diazabicyclo[3.2.1]oct-8-yl]methyl}ethylcarbamate (m/z=437);
methyl (1S)-2-(3-{[2-(acetylamino)-4-methyl-1,3-thiazol-5-yl]sulfonyl}-3,8-diazabicyclo[3.2.1]oct-8-yl)-1-[(4-cyanophenoxy)methyl]ethylcarbamate (m/z=563);
methyl (1S)-2-(4-cyanophenoxy)-1-({3-[(4-nitrophenyl)sulfonyl]-3,8-diazabicyclo[3.2.1]oct-8-yl}methyl)ethylcarbamate (m/z=530);
methyl (1S)-2-(4-cyanophenoxy)-1-({3-[(3,4-dimethoxyphenyl)sulfonyl]-3,8-diazabicyclo[3.2.1]oct-8-yl}methyl)ethylcarbamate (m/z=545);
methyl (1S)-2-(4-cyanophenoxy)-1-({3-[(1-methyl-1H-imidazol-4-yl)-sulfonyl]-3,8-diazabicyclo[3.2.1]oct-8-yl}methyl)ethylcarbamate (m/z=489);
4-[1-(4-hydroxyphenoxy)-4-(3-isobutyryl-3,8-diazabicyclo[3.2.1]oct-8-yl)-butyl]benzonitrile (m/z=448);
4-{1-(4-hydroxyphenoxy)-4-[3-(3-methylbutanoyl)-3,8-diazabicyclo[3.2.1]oct-8-yl]butyl}benzonitrile (m/z=462);
4-[4-[3-(2,1,3-benzoxadiazol-5-ylcarbonyl)-3,8-diazabicyclo[3.2.1]oct-8-yl]-1-(4-hydroxyphenoxy)butyl]benzonitrile (m/z=524);
4-(1-(4-hydroxyphenoxy)-4-{3-[(1-methyl-1H-indol-2-yl)carbonyl]-3,8-diazabicyclo[3.2.1]oct-8-yl}butyl)benzonitrile (m/z=535);
N-({8-[2-(2,4-dicyanophenoxy)ethyl]-3,8-diazabicyclo[3.2.1]oct-3-yl}-carbonyl)-4-methylbenzenesulfonamide (m/z=480);
8-[2-(2,4-dicyanophenoxy)ethyl]-N-{4-[(trifluoromethyl)sulfanyl]phenyl}-3,8-diazabicyclo[3.2.1]octane-3-carboxamide (m/z=502);
N-(cyclopropylmethyl)-8-[2-(2,4-dicyanophenoxy)ethyl]-3,8-diazabicyclo[3.2.1]octane-3-carboxamide (m/z=380);
8-[2-(2,4-dicyanophenoxy)ethyl]-N-isopropyl-3,8-diazabicyclo[3.2.1]octane-3-carboxamide (m/z=368);
8-[2-(2,4-dicyanophenoxy)ethyl]-N-(3,4-difluorophenyl)-3,8-diazabicyclo[3.2.1]octane-3-carboxamide (m/z=438);
N-butyl-8-[2-(2,4-dicyanophenoxy)ethyl]-3,8-diazabicyclo[3.2.1]octane-3-carboxamide (m/z=382);
methyl (1S)-2-(4-cyanophenoxy)-1-({3-[(ethylamino)carbonyl]-3,8-diazabioyclo[3.2.1]oct-8-yl}methyl)ethylcarbamate (m/z=416);
methyl (1S)-2-(4-cyanophenoxy)-1-[(3-{[(3,5-dimethyl-4-isoxazolyl)-amino]carbonyl}-3,8-diazabicyclo[3.2.1]oct-8-yl)methyl]ethylcarbamate (m/z=483);
methyl (1S)-2-(4-cyanophenoxy)-1-{[3-({[(4-methylphenyl)sulfonyl]amino}carbonyl)-3,8-diazabicyclo[3.2.1]oct-8-yl]methyl}ethylcarbamate (m/z=542);
methyl (1S)-2-(4-cyanophenoxy)-1-{[3-({4-[(trifluoromethyl)sulfanyl]anilino}carbonyl)-3,8-diazabicyclo[3.2.1]oct-8-yl]methyl}ethylcarbamate (m/z=564);
methyl (1S)-2-(4-cyanophenoxy)-1-[(3-{[(cyclopropylmethyl)amino]carbonyl}-3,8-diazabicyclo[3.2.1]oct-8-yl)methyl]ethylcarbamate (m/z=442);
methyl (1S)-2-(4-cyanophenoxy)-1-({3-[(isopropylamino)carbonyl]-3,8-diazabicyclo[3.2.1]oct-8-yl}methyl)ethylcarbamate (m/z=430);
methyl (1S)-2-(4-cyanophenoxy)-1-({3-[(3,4-difluoroanilino)carbonyl]-3,8-diazabicyclo[3.2.1]oct-8-yl}methyl)ethylcarbamate (m/z=500); 8-[2-amino-4-(4-cyanophenoxy)butyl]-N-ethyl-3,8-diazabicyclo[3.2.1]octane-3-carboxamide (m/z=372);
8-[2-amino-4-(4-cyanophenoxy)butyl]-N-{4-[(trifluoromethyl)sulfanyl]phenyl}-3,8-diazabicyclo[3.2.1]octane-3-carboxamide (m/z=520);
8-[2-amino-4-(4-cyanophenoxy)butyl]-N-tetrahydro-2H-pyran-2-yl-3,8-diazabicyclo[3.2.1]octane-3-carboxamide (m/z=428);
8-[2-amino-4-(4-cyanophenoxy)butyl]-N-(cyclopropylmethyl)-3,8-diazabicyclo[3.2.1]octane-3-carboxamide (m/z=398);
8-[2-amino-4-(4-cyanophenoxy)butyl]-N-isopropyl-3,8-diazabicyclo[3.2.1]octane-3-carboxamide (m/z=386);
8-[2-amino-4-(4-cyanophenoxy)butyl]-N-(3,4-difluorophenyl)-3,8-diazabicyclo[3.2.1]octane-3-carboxamide (m/z=456);
8-[4-(4-cyanophenyl)-4-(4-hydroxyphenoxy)butyl]-N-ethyl-3,8-diazabicyclo[3.2.1]octane-3-carboxamide (m/z=449);

8-[4-(4-cyanophenyl)-4-(4-hydroxyphenoxy)butyl]-N-(3,5-dimethyl-4-isoxazolyl)-3,8-diazabicyclo[3.2.1]octane-3-carboxamide (m/z=516);

N-({8-[4-(4-cyanophenyl)-4-(4-hydroxyphenoxy)butyl]-3,8-diazabicyclo-[3.2.1]oct-3-yl}carbonyl)-4-methylbenzenesulfonamide (m/z=575);

8-[4-(4-cyanophenyl)-4-(4-hydroxyphenoxy)butyl]-N-(4-methoxyphenyl)-3,8-diazabicyclo[3.2.1]octane-3-carboxamide (m/z=527);

8-[4-(4-cyanophenyl)-4-(4-hydroxyphenoxy)butyl]-N-{4-[(trifluoromethyl)sulfanyl]phenyl}-3,8-diazabicyclo[3.2.1]octane-3-carboxamide (m/z=597);

8-[4-(4-cyanophenyl)-4-(4-hydroxyphenoxy)butyl]-N-tetrahydro-2H-pyran-2-yl-3,8-diazabicyclo[3.2.1]octane-3-carboxamide (m/z=505);

8-[4-(4-cyanophenyl)-4-(4-hydroxyphenoxy)butyl]-N-(3,4-difluorophenyl)-3,8-diazabicyclo[3.2.1]octane-3-carboxamide (m/z=533);

N-butyl-8-[4-(4-cyanophenyl)-4-(4-hydroxyphenoxy)butyl]-3,8-diazabicyclo[3.2.1]octane-3-carboxamide (m/z=477);

ethyl 8-[2-(2,4-di-cyanophenoxy)ethyl]-3,8-diazabicyclo[3.2.1]octane-3-carboxylate (m/z=355);

2-butynyl 8-[2-(2,4-dicyanophenoxy)ethyl]-3,8-diazabicyclo[3.2.1]octane-3-carboxylate (m/z=379);

2-methoxyethyl 8-[2-(2,4-di-cyanophenoxy)ethyl]-3,8-diazabicyclo[3.2.1]octane-3-carboxylate (m/z=385);

3-(methylsulfonyl)propyl 8-[2-(2,4-dicyanophenoxy)ethyl]-3,8-diazabicyclo[3.2.1]octane-3-carboxylate (m/z=447);

1-cyano-1-methylethyl 8-[2-(2,4-dicyanophenoxy)ethyl]-3,8-diazabicyclolo[3.2.1]octane-3-carboxylate (m/z=394);

2-(4-morpholinyl)ethyl 8-[2-(2,4-dicyanophenoxy)ethyl]-3,8-diazabicyclo[3.2.1]octane-3-carboxylate (m/z=440);

2-(4-pyridinyl)ethyl 8-[2-(2,4-dicyanophenoxy)ethyl]-3,8-diazabicyclo[3.2.1]octane-3-carboxylate (m/z=432);

2-hydroxy-1,1-dimethylethyl 8-[2-(2,4-dicyanophenoxy)ethyl]-3,8-diazabicyclo[3.2.1]octane-3-carboxylate (m/z=399);

ethyl 8-{(2S)-3-(4-cyanophenoxy)-2-[(methoxycarbonyl)amino]propyl}-3,8-diazabicyclo[3.2.1]octane-3-carboxylate (m/z=417);

2-methoxyethyl 8-{(2S)-3-(4-cyanophenoxy)-2-[(methoxycarbonyl)amino]propyl}-3,8-diazabicyclo[3.2.1]octane-3-carboxylate (m/z=447);

3-(methylsulfonyl)propyl 8-{(2S)-3-(4-cyanophenoxy)-2-[(methoxycarbonyl)amino]propyl}-3,8-diazabicyclo[3.2.1]octane-3-carboxylate (m/z=509);

1-cyano-1-methylethyl 8-{(2S)-3-(4-cyanophenoxy)-2-[(methoxycarbonyl)-amino]propyl}-3,8-diazabicyclo[3.2.1]octane-3-carboxylate (m/z=456);

2-(4-morpholinyl)ethyl 8-{(2S)-3-(4-cyanophenoxy)-2-[(methoxycarbonyl)-amino]propyl}-3,8-diazabicyclo[3.2.1]octane-3-carboxylate (m/z=502);

2-(4-pyridinyl)ethyl 8-{(2S)-3-(4-cyanophenoxy)-2-[(methoxycarbonyl)amino]propyl}-3,8-diazabicyclo[3.2.1]octane-3-carboxylate (m/z=494);

2-(4-acetyl-1-piperazinyl)ethyl 8-{(28)-3-(4-cyanophenoxy)-2-[(methoxycarbonyl)amino]propyl}-3,8-diazabicyclo[3.2.1]octane-3-carboxylate (m/z=543);

ethyl 8-[2-amino-4-(4-cyanophenoxy)butyl]-3,8-diazabioyclo[3.2.1]octane-3-carboxylate (m/z=373);

2-butynyl 8-[2-amino-4-(4-cyanophenoxy)butyl]-3,8-diazabicyclo[3.2.1]octane-3-carboxylate (m/z=397);

3-(methylsulfonyl)propyl 8-[2-amino-4-(4-cyanophenoxy)butyl]-3,8-diazabicyclo[3.2.1]octane-3-carboxylate (m/z=465);

1-cyano-1-methylethyl 8-[2-amino-4-(4-cyanophenoxy)butyl]-3,8-diazabicyclo[3.2.1]octane-3-carboxylate (m/z=412);

2-(4-acetyl-1-piperazinyl)ethyl 8-[2-amino-4-(4-cyanophenoxy)butyl]-3,8-diazabicyclo[3.2.1]octane-3-carboxylate (m/z=499);

ethyl 8-[4-(4-cyanophenyl)-4-(4-hydroxyphenoxy)butyl]-3,8-diazabicyclo[3.2.1]octane-3-carboxylate (m/z=450);

2-butynyl 8-[4-(4-cyanophenyl)-4-(4-hydroxyphenoxy)butyl]-3,8-diazabicyclo[3.2.1]octane-3-carboxylate (m/z=474);

2-methoxyethyl 8-[4-(4-cyanophenyl)-4-(4-hydroxyphenoxy)butyl]-3,8-diazabicyclo[3.2.1]octane-3-carboxylate (m/z=480);

3-(methylsulfonyl)propyl 8-[4-(4-cyanophenyl)-4-(4-hydroxyphenoxy)butyl]-3,8-diazabicyclo[3.2.1]octane-3-carboxylate (m/z=542);

1-cyano-1-methylethyl 8-[4-(4-cyanophenyl)-4-(4-hydroxyphenoxy)butyl]-3,8-diazabicyclo[3.2.1]octane-3-carboxylate (m/z=489);

2-(4-morpholinyl)ethyl 8-[4-(4-cyanophenyl)-4-(4-hydroxyphenoxy)butyl]-3,8-diazabicyclo[3.2.1]octane-3-carboxylate (m/z=535);

2-(4-acetyl-1-piperazinyl)ethyl 8-[4-(4-cyanophenyl)-4-(4-hydroxyphenoxy)butyl]-3,8-diazabicyclo[3.2.1]octane-3-carboxylate (m/z=576);

2-hydroxy-1,1-dimethylethyl 8-[4-(4-cyanophenyl)-4-(4-hydroxyphenoxy)-butyl]-3,8-diazabicyclo[3.2.1]octane-3-carboxylate (m/z=494);

1,1-dimethyl-2-propynyl 8-[4-(4-cyanophenyl)-4-(3,4-dimethoxyphenoxy)-butyl]-3,8-diazabicyclo[3.2.1]octane-3-carboxylate (m/z=532);

1-methyl-2-propynyl 8-[4-(4-cyanophenyl)-4-(3,4-dimethoxyphenoxy)-butyl]-3,8-diazabicyclo[3.2.1]octane-3-carboxylate (m/z=518);

1-phenyl-2-propynyl 8-[4-(4-cyanophenyl)-4-(3,4-dimethoxyphenoxy)-butyl]-3,8-diazabicyclo[3.2.1]octane-3-carboxylate (m/z=580);

1-isopropyl-2-propynyl 8-[4-(4-cyanophenyl)-4-(3,4-dimethoxyphenoxy)-butyl]-3,8-diazabicyclo[3.2.1]octane-3-carboxylate (m/z=546);

2-propynyl 8-[4-(4-cyanophenyl)-4-(3,4-dimethoxyphenoxy)butyl]-3,8-diazabicyclo[3.2.1]octane-3-carboxylate (m/z=504);

ethyl 8-[4-(4-cyanophenyl)-4-(3,4-dimethoxyphenoxy)butyl]-3,8-diazabicyclo[3.2.1]octane-3-carboxylate (m/z=494);

4-fluorophenyl 8-[4-(4-cyanophenyl)-4-(3,4-dimethoxyphenoxy)butyl]-3,8-diazabicyclo[3.2.1]octane-3-carboxylate (m/z=560);

cyclopentyl 8-[4-(4-cyanophenyl)-4-(3,4-dimethoxyphenoxy)butyl]-3,8-diazabicyclo[3.2.1]octane-3-carboxylate (m/z=534);

isopropyl 8-[4-(4-cyanophenyl)-4-(3,4-dimethoxyphenoxy)butyl]-3,8-diazabicyclo[3.2.1]octane-3-carboxylate (m/z=508);

4-[4-{3-[(2S)-3-cyano-2-hydroxypropyl]-3,8-diazabicyclo[3.2.1]oct-8-yl}-1-(3,4-dimethoxyphenoxy)butyl]benzonitrile (m/z=505);

8-[4-(4-cyanophenyl)-4-(3,4-dimethoxyphenoxy)butyl]-N-(2,6-dichloro-4-pyridinyl)-3,8-diazabicyclo[3.2.1]octane-3-carboxamide (m/z=610);

8-[4-(4-cyanophenyl)-4-(3,4-dimethoxyphenoxy)butyl]-N-[4-(dimethylamino)phenyl]-3,8-diazabicyclo[3.2.1]octane-3-carboxamide (m/z=584);

8-[4-(4-cyanophenyl)-4-(3,4-dimethoxyphenoxy)butyl]-N-(3-pyridinyl)-3,8-diazabicyclo[3.2.1]octane-3-carboxamide;
8-[4-(4-cyanophenyl)-4-(3,4-dimethoxyphenoxy)butyl]-N-cyclohexyl-3,8-diazabicyclo[3.2.1]octane-3-carboxamide (m/z=547);
N-(4-cyanophenyl)-8-[4-(4-cyanophenyl)-4-(3,4-dimethoxyphenoxy)butyl]-3,8-diazabicyclo[3.2.1]octane-3-carboxamide (m/z=566);
N-(3-cyanophenyl)-8-[4-(4-cyanophenyl)-4-(3,4-dimethoxyphenoxy)butyl]-3,8-diazabicyclo[3.2.1]octane-3-carboxamide (m/z=566);
tert-butyl 8-[(4R)-4-(4-cyanophenyl)-4-(3,4-dimethoxyphenoxy)butyl]-3,8-diazabicyclo[3.2.1]octane-3-carboxylate (m/z=522);
4-((1S)-1-(3,4-dimethoxyphenoxy)-4-{3-[(1-methyl-1H-imidazol-4-yl)-sulfonyl]-3,8-diazabicyclo[3.2.1]oct-8-yl}butyl)benzonitrile (m/z=566);
4-((1R)-1-(3,4-dimethoxyphenoxy)-4-{3-[(1-methyl-1H-imidazol-4-yl)-sulfonyl]-3,8-diazabicyclo[3.2.1]oct-8-yl}butyl)benzonitrile (m/z=566);
R or S 8-[2-amino-4-(4-cyanophenoxy)butyl]-N-butyl-3,8-diazabicyclo[3.2.1]octane-3-carboxamide;
S or R 8-[2-amino-4-(4-cyanophenoxy)butyl]-N-butyl-3,8-diazabicyclo[3.2.1]octane-3-carboxamide;
2-butynyl 8-[(2S)-3-(4-cyanophenoxy)-2-hydroxypropyl]-3,8-diazabicyclo[3.2.1]octane-3-carboxylate (m/z=384);
8-[(2S)-3-(4-cyanophenoxy)-2-hydroxypropyl]-N-(3,4-difluorophenyl)-3,8-diazabicyclo[3.2.1]octane-3-carboxamide (m/z=443);
8-[2-amino-4-(4-cyanophenoxy)butyl]-N-cyclohexyl-3,8-diazabicyclo[3.2.1]octane-3-carboxamide (m/z=426);
8-[2-amino-4-(4-cyanophenoxy)butyl]-N-propyl-3,8-diazabicyclo[3.2.1]octane-3-carboxamide (m/z=386);
N-allyl-8-[2-amino-4-(4-cyanophenoxy)butyl]-3,8-diazabicyclo[3.2.1]octane-3-carboxamide (m/z=384); and
8-[2-amino-4-(4-cyanophenoxy)butyl]-N-(tert-butyl)-3,8-diazabicyclo[3.2.1]octane-3-carboxamide (m/z=400).

Example 4

Title compounds of the above examples were tested in Test A above and were found to have $D_{10}$ values of at least 6.0.

Example 5

Title compounds of the above examples were tested in Test B above and were found to have pIC50 values of at least 5.5.

| Abbreviations | |
|---|---|
| Ac = | acetyl |
| ADDP = | 1,1'-(azodicarbonyl)dipiperidine |
| API = | atmospheric pressure ionisation (in relation to MS) |
| aq. = | aqueous |
| br = | broad (in relation to NMR) |
| Bt = | benzotriazole |
| t-BuOH = | tert-butanol |
| CI = | chemical ionisation (in relation to MS) |
| mCPBA = | meta-chloroperoxybenzoic acid |
| d = | doublet (in relation to NMR) |
| DBU = | diazabicyclo[5.4.0] undec-7-ene |
| DCM = | dichloromethane |
| dd = | doublet of doublets (in relation to NMR) |
| DMAP = | 4-dimethylaminopyridine |

| Abbreviations | |
|---|---|
| DMF = | N,N-dimethylformamide |
| DMSO = | dimethylsulfoxide |
| EDC = | 1-[3-(dimethylamino)propyl]-3-ethylcarbodiimide |
| Et = | ethyl |
| EtOAc = | ethyl acetate |
| eq. = | equivalents |
| ES = | electrospray (in relation to MS) |
| FAB = | fast atom bombardment (in relation to MS) |
| h = | hour(s) |
| HCl = | hydrochloric acid |
| HEPES = | 4-(2-hydroxyethyl)-1-piperazineethanesulfonic acid |
| HPLC = | high performance liquid chromatography |
| IPA = | iso-propyl alcohol (propan-2-ol) |
| m = | multiplet (in relation to NMR) |
| Me = | methyl |
| MeCN = | acetonitrile |
| MeOH = | methanol |
| min. = | minute(s) |
| m.p. = | melting point |
| MS = | mass spectroscopy |
| NADPH = | nicotinamide adenine dinucleotide phosphate, reduced form |
| OAc = | acetate |
| Pd/C = | palladium on carbon |
| q = | quartet (in relation to NMR) |
| rt = | room temperature |
| s = | singlet (in relation to NMR) |
| t = | triplet (in relation to NMR) |
| TBP = | tributyl phosphine |
| TEA = | triethylamine |
| THF = | tetrahydrofuran |
| tlc = | thin layer chromatography |

Prefixes n-, s-, i-, t- and tert- have their usual meanings: normal, secondary, iso, and tertiary.

The invention claimed is:

1. A method for the treatment or prophylaxis of an atrial arrhythmia comprising administering to a patient in need thereof an effective amount of a compound of formula I:

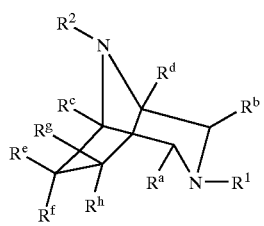

I wherein
one of $R^1$ and $R^2$ represents $R^{1a}$ and the other represents a fragment of the formula Ia,

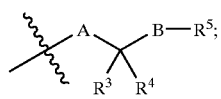

Ia $R^{1a}$ represents $C_{1-12}$ alkyl (optionally substituted and/or terminated by one or more groups selected from halo, cyano, nitro, aryl, Het$^1$, —C(O)R$^{7a}$, —OR$^{7b}$, —N(R$^8$)R$^{7c}$, —C(O)XR$^9$, —C(O)N(R$^{10}$)R$^{7d}$ and —S(O)$_2$R$^{11}$) Het$^2$, —C(O)R$^{7a}$, —C(O)XR$^9$, —C(O)N(R$^{10}$)R$^{7d}$ or —S(O)$_2$R$^{11}$;

$R^{7a}$ to $R^{7d}$ independently represent, at each occurrence when used herein, H, $C_{1-6}$ alkyl (optionally substituted and/or terminated by one or more substituents selected from —OH, $C_{1-6}$ alkoxy, halo, cyano, nitro, aryl, $Het^3$ and —NHC(O)R1²), aryl or $Het^4$, or $R^{7d}$, together with $R^{10}$, represents $C_{3-6}$ alkylene (which alkylene group is optionally interrupted by an O atom and/or is optionally substituted by one or more $C_{1-3}$ alkyl groups);

$R^{12}$ represents H, $C_{1-4}$ alkyl (optionally substituted and/or terminated by one or more substituents selected from halo, cyano, aryl and —NHC(O)R¹³) or aryl;

$R^{13}$ represents H, $C_{1-4}$ alkyl or aryl;

$R^8$ represents H, $C_{1-6}$ alkyl (optionally substituted and/or terminated by one or more substituents selected from —OH, halo, cyano, nitro and aryl), aryl, —C(O)$R^{14a}$ or —C(O)O$R^{14b}$;

$R^{14a}$ and $R^{14b}$ represent $C_{1-6}$ alkyl (optionally substituted and/or terminated by one or more substituents selected from —OH, halo, cyano, nitro and aryl) or aryl, or $R^{14a}$ represents H;

X represents O or S;

$R^9$ represents, at each occurrence when used herein, aryl or $C_{1-12}$ alkyl (which alkyl group is optionally substituted and/or terminated by one or more substituents selected from —OH, halo, cyano, nitro, aryl, $C_{1-6}$ alkoxy, —SO$_2$R¹⁵ and $Het^5$);

$R^{15}$ represents $C_{1-6}$ alkyl or aryl;

$R^{10}$ represents, at each occurrence when used herein, H, $C_{1-12}$ alkyl, $C_{1-6}$ alkoxy (which latter two groups are optionally substituted and/or terminated by one or more substituents selected from —OH, halo, cyano, nitro, $C_{1-4}$ alkyl and $C_{1-4}$ alkoxy), -D-aryl, -D-aryloxy, -D-Het⁶, -D-N(H)C(O)$R^{16a}$, -D-S(O)$_2$$R^{17a}$, -D-C(O)$R^{16b}$, -D-C(O)O$R^{17b}$, -D-C(O)N($R^{16c}$)$R^{16d}$, or $R^{10}$, together with $R^{7d}$, represents $C_{3-6}$ alkylene (which alkylene group is optionally interrupted by an O atom and/or is optionally substituted by one or more $C_{1-3}$ alkyl groups);

$R^{16a}$ to $R^{16d}$ independently represent H, $C_{1-6}$ alkyl (optionally substituted and/or terminated by one or more substituents selected from —OH, halo, cyano, nitro and aryl), aryl, or $R^{16c}$ and $R^{16d}$ together represent $C_{3-6}$ alkylene;

$R^{17a}$ and $R^{17b}$ independently represent $C_{1-6}$ alkyl (optionally substituted and/or terminated by one or more substituents selected from —OH, halo, cyano, nitro and aryl) or aryl;

D represents a direct bond or $C_{1-6}$ alkylene;

$R^{11}$ represents, at each occurrence when used herein, $C_{1-6}$ alkyl (optionally substituted and/or terminated by one or more substituents selected from —OH, halo, cyano, nitro and aryl), aryl or $Het^7$;

$R^3$ represents, H, halo, $C_{1-6}$ alkyl, -E-O$R^{18}$, -E-N($R^{19}$)$R^{20}$ or, together with $R^4$, represents =O;

$R^4$ represents H, $C_{1-6}$ alkyl or, together with $R^3$, represents =O;

$R^{18}$ represents H, $C_{1-6}$ alkyl, -E-aryl, -E-Het⁸, —C(O)$R^{21a}$, —C(O)O$R^{21b}$ or —C(O)N($R^{22a}$)$R^{22b}$;

$R^{19}$ represents H, $C_{1-6}$ alkyl, -E-aryl, -E-Het⁸, —C(O)$R^{21a}$, —C(O)$R^{21a}$, —C(O)O$R^{21b}$, —S(O)$_2$$R^{21c}$, —[C(O)]$^p$N($R^{22a}$)$R^{22b}$ or —C(NH)NH$_2$;

$R^{20}$ represents H, $C_{1-6}$ alkyl, -E-aryl or —C(O)$R^{21d}$;

$R^{21a}$ to $R^{21d}$ independently represent, at each occurrence when used herein, $C_{1-6}$ alkyl (optionally substituted and/or terminated by one or more substituents selected from halo, aryl and Het⁹), aryl, Het¹⁰, or $R^{21a}$ and $R^{21d}$ independently represent H;

$R^{22a}$ and $R^{22b}$ independently represent, at each occurrence when used herein, H or $C_{1-6}$ alkyl (optionally substituted and/or terminated by one or more substituents selected from halo, aryl and Het¹¹), aryl, Het¹², or together represent $C_{3-6}$ alkylene, optionally interrupted by an O atom;

E represents, at each occurrence when used herein, a direct bond or $C_{1-4}$ alkylene;

p represents 1 or 2;

A represents -G-, -J-N($R^{24}$)— or -J-O— (in which latter two groups, N($R^{24}$)— or O— is attached to the carbon atom bearing $R^3$ and $R^4$);

B represents -Z-, -Z-N($R^{25}$)—, —N($R^{25}$)-Z-, -Z-S(O)$_n$—, -Z-O— (in which latter two groups, Z is attached to the carbon atom bearing $R^3$ and $R^4$);

G represents $C_{1-6}$ alkylene;

J represents $C_{2-6}$ alkylene;

Z represents a direct bond or $C_{1-4}$ alkylene;

$R^{24}$ and $R^{25}$ independently represent H or $C_{1-6}$ alkyl;

$R^5$ represents aryl or Het¹³, both of which groups are optionally substituted by one or more substituents selected from —OH, cyano, halo, $C_{1-6}$ alkyl (optionally terminated by —N(H)C(O)O$R^{26a}$), $C_{1-6}$ alkoxy, Het¹, aryl, —C(O)$R^{27c}$, —C(O)O$R^{27d}$, —C(O)N($R^{27e}$)$R^{27r}$, —N($R^{27i}$)C(O)N($R^{27j}$)$R^{27k}$, —OS(O)$_n$$R^{26c}$—OS(O)$_2$$R^{26d}$, —S(O)$_2$N($R^{27n}$)$R^{27p}$ and (in the case of Het¹³ only) oxo;

Het¹³ represents a four- to twelve-membered heterocyclic group containing one or more heteroatoms selected from oxygen, nitrogen and/or sulfur;

Het¹ to Het¹² independently represent, at each occurrence when used herein, four- to twelve-membered heterocyclic groups containing one or more heteroatoms selected from oxygen, nitrogen and/or sulfur, which heterocyclic groups are optionally substituted by one or more substituents including =O, —OH, cyano, halo, nitro, $C_{1-6}$ alkyl (optionally terminated by —N(H)C(O)O$R^{26a}$), $C_{1-6}$ alkoxy, Het¹, aryl, —N($R^{27a}$)$R^{27b}$, —C(O)$R^{27c}$, —C(O)O$R^{27d}$, —C(O)N($R^{27e}$)$R^{27f}$, —N($R^{27g}$)C(O)$R^{27h}$, —N($R^{27i}$)C(O)N($R^{27j}$)$R^{27k}$, —N($R^{27m}$)S(O)$_2$$R^{26h}$, —S(O)$_n$$R^{26c}$, —OS(O)$_2$$R^{26d}$ and —S(O)$_2$N($R^{27n}$)$R^{27p}$;

$R^{26a}$ to $R^{26d}$ independently represent, at each occurrence when used herein, $C_{1-6}$ alkyl;

$R^{27a}$ to $R^{27p}$ independently represent, at each occurrence when used herein, H or $C_{1-6}$ alkyl;

n represents, at each occurrence, 0, 1 or 2; and $R^a$ to $R^h$ independently represent H or $C_{1-4}$ alkyl;

wherein each aryl and aryloxy group, unless otherwise specified, is optionally substituted by one or more of substituents including —OH, cyano, halo, nitro, $C_1$–$C_6$-alkoxy, —C(O)N($R^{27e}$)$R^{27f}$;

or a quaternary ammonium salt, an N-oxide, a pharmaceutically acceptable salt, a diastereomer or a tautomer thereof.

2. The method as claimed in claim 1, wherein, in the compound of formula I, the optional substituents on aryl and aryloxy groups are one or more groups selected from —OH, cyano, halo, nitro, $C_{1-6}$, alkyl (optionally terminated by —N(H)C(O)O$R^{26a}$), $C_{1-6}$ alkoxy, Het¹, aryl (which aryl group may not be substituted with any further aryl groups), —N($R^{27a}$)$R^{27b}$, —C(O)$R^{27c}$, —C(O)O$R^{27d}$, —C(O)N($R^{27c}$)$R^{27r}$, —N($R^{27g}$)C(O)$R^{27h}$, —N($R^{27i}$)C(O)N($R^{27j}$) $R^{27k}$, —N($R^{27m}$)S(O)$_2$$R^{26b}$, S(O)$_n$$R^{26C}$, —OS(O)$_2$$R^{26d}$ and —S(O)$^2$N($R^{27n}$)$R^{27p}$ (wherein Het¹, $R^{26a}$ to $R^{26d}$, $R^{27a}$, to $R^{27p}$ and n are as defined in claim 1).

3. The method as claimed in claim 1, wherein, in the compound of formula I, $R^{1a}$ represents $C_{1-6}$ alkyl (which alkyl group is optionally part cyclic/acyclic or interrupted by oxygen and/or which alkyl group is optionally substituted and/or terminated by one or more groups selected from halo, cyano, optionally substituted phenyl, optionally substituted Het$^1$, —C(O)R$^{7a}$, —OR$^{7b}$—C(O)OR$^9$, —C(O)N(R$^{10}$)H and —S(O)$_2$—C$_{1-4}$ alkyl), optionally substituted Het$^2$, —C(O)R$^{7a}$, —C(O)OR$^9$, —C(O)N(R$^{10}$).H or —S(O)$_2$R$^{11}$.

4. The method as claimed in claim 3, wherein, in the compound of formula I, R$^{7a}$ and R$^{7b}$ independently represent, at each occurrence when used herein, H, C$_{1-6}$ alkyl (optionally substituted and/or terminated by one or more substituents selected from C$_{1-6}$ alkoxy, halo, optionally substituted phenyl, optionally substituted Het$^3$ and —NHC(O)R$^{12}$), optionally substituted phenyl or optionally substituted Het$^4$.

5. The method as claimed in claim 4, wherein, in the compound of formula I, R$^{12}$ represents C$_{1-3}$ alkyl (optionally substituted and/or terminated by one or more substituents selected from halo and —NHC(O)R$^{13}$).

6. The method as claimed in claim 5, wherein, in the compound of formula I, R$^{13}$ represents C$_{1-3}$ alkyl.

7. The method as claimed in claim 1, wherein, in the compound of formula I, R$^9$ represents, at each occurrence when used herein, optionally substituted phenyl or C$_{1-9}$ alkyl (which alkyl group is optionally unsaturated or cyclic and/or which alkyl group is optionally substituted and/or terminated by one or more substituents selected from —OH, halo, cyano, optionally substituted phenyl, C$_{1-6}$ alkoxy, —SO$_2$—C$_{1-4}$ alkyl and optionally substituted Het$^5$).

8. The method as claimed in claim 1, wherein, in the compound of formula I, R$^{10}$ represents, at each occurrence when used herein, C$_{1-9}$ alkyl (which alkyl group is optionally cyclic, part cyclic/acyclic, unsaturated or interrupted by oxygen and/or which alkyl group is optionally substituted and/or terminated by one or more substituents selected from halo and C$_{1-4}$ alkoxy), -D-(optionally substituted phenyl), -D-(optionally substituted Het$^6$) or —S(O)$_2$R$^{17a}$.

9. The method as claimed in claim 8, wherein, in the compound of formula I, R$^{17a}$ represents C$_{1-4}$ alkyl (optionally substituted and/or terminated by one or more substituents selected from halo and phenyl) or optionally substituted phenyl.

10. The method as claimed in claim 8, wherein, in the compound of formula I, D represents a direct bond or C$_{1-4}$ alkylene.

11. The method as claimed in claim 1, wherein, in the compound of formula I, R$^{11}$ represents, at each occurrence when used herein, C$_{1-5}$ alkyl (optionally substituted and/or terminated by one or more substituents selected from halo and phenyl), optionally substituted phenyl or optionally substituted Het$^7$.

12. The method as claimed in claim 1, wherein, in the compound of formula I, R$^3$ represents H, C$_{1-3}$ alkyl, —OR$^{18}$ or —N(R$^{19}$)H.

13. The method as claimed in claim 1, wherein, in the compound of formula I, R$^4$ represents H or C$_{1-3}$ alkyl.

14. The method as claimed in claim 12, wherein, in the compound of formula I, R$^{18}$ represents H, optionally substituted phenyl, optionally substituted Het$^8$, —C(O)R$^{21a}$ or —C(O)OR$^{21b}$.

15. The method as claimed in claim 12, wherein, in the compound of formula I, R$^{19}$ represents H, optionally substituted phenyl, optionally substituted Het$^8$, —C(O)R$^{21}$a, —C(O)OR$^{21b}$ or —[C(O)$_p$]N(R$^{22a}$)R$^{22b}$.

16. The method as claimed in claim 14, wherein, in the compound of formula I, R$^{21a}$ and R$^{21b}$ independently represent, at each occurrence when used herein, C$_{1-4}$ alkyl (optionally substituted and/or terminated by one or more substituents selected from halo and phenyl).

17. The method as claimed in claim 15, wherein, in the compound of formula I, R$^{22a}$ and R$^{22b}$ independently represent H or C$_{1-4}$ alkyl (optionally substituted and/or terminated by one or more substituents selected from halo and phenyl).

18. The method as claimed in claim 15, wherein, in the compound of formula I, p represents 1 or 2.

19. The method as claimed in claim 1, wherein, in the compound of formula I, A represents C$_{1-5}$ alkylene.

20. The method as claimed in claim 1, wherein, in the compound of formula I, B represents -Z-, -Z-N(R$^{25}$)—, -Z-S(O)$_2$—, -Z-O— (in which latter three groups, Z is attached to the carbon atom bearing R$^3$ and R$^4$).

21. The method as claimed in claim 20, wherein, in the compound of formula I, Z represents a direct bond or C$_{1-3}$ alkylene.

22. The method as claimed in claim 20, wherein, in the compound of formula 1, R$^{25}$ represents H or C$_{1-4}$ alkyl.

23. The method as claimed in claim 1, wherein, in the compound of formula 1, R$^5$ represents phenyl optionally substituted by one or more substituents selected from —OH, cyano, halo, C$_{1-3}$ alkyl, C$_{1-3}$ alkoxy, —C(O)R$^{27c}$ and —N(H)C(O)N(H)R$^{27k}$.

24. The method as claimed in claim 1, wherein, in the compound of formula I, Het$^1$ to Het$^8$ independently represent, at each occurrence when used herein, five- to ten-membered heterocyclic groups containing one to four heteroatoms selected from oxygen, nitrogen and/or sulfur, which heterocyclic groups are optionally substituted by one or more groups selected from =O, cyano, halo, C$_{1-5}$ alkyl, C$_{1-5}$ alkoxy, —N(R$^{27a}$)R$^{27b}$, —C(O)R$^{27c}$, —N(H)C(O)R$^{27h}$ and —S(O)$_2$R$^{26c}$.

25. The method as claimed in claim 1, wherein, in the compound of formula I, R$^a$ to R$^h$ all represent H.

26. The method as claimed in claim 3, wherein, in the compound of formula I, optional substituents on phenyl groups are one or more groups selected from —OH, cyano, halo, nitro, C$_{1-5}$ alkyl, C$_{1-5}$ alkoxy, optionally substituted Het$^1$, —N(R$^{27a}$)R$^{27b}$, —C(O)R$^{27c}$, —N(H)C(O)R$^{27h}$ and —SR$^{26c}$.

27. The method as claimed in claim 1, wherein, in the compound of formula 1, R$^{2b}$ and R$^{26c}$ independently represent, at each occurrence when used herein, C$_{1-3}$ alkyl optionally substituted by halo.

28. The method as claimed in claim 1, wherein, in the compound of formula I, R$^{27a}$ to R$^{27k}$ independently represent, at each occurrence when used herein, H or C$_{1-3}$ alkyl optionally substituted by halo.

29. A method of prophylaxis or treatment of an atrial arrhythmia which method comprises administration of a therapeutically effective amount of a compound of formula I as defined in claim 1 to a person suffering from, or susceptible to, such a condition.

* * * * *

UNITED STATES PATENT AND TRADEMARK OFFICE
CERTIFICATE OF CORRECTION

PATENT NO.    : 7,012,074 B2  
DATED         : March 14, 2006  
INVENTOR(S)   : Bjorsne et al.

Page 1 of 1

It is certified that error appears in the above-identified patent and that said Letters Patent is hereby corrected as shown below:

<u>Title page,</u>
Item [86], PCT No.: delete "PCT/SE01/02994" and insert -- PCT/SE01/02294 --.

Signed and Sealed this

Sixteenth Day of May, 2006

JON W. DUDAS
*Director of the United States Patent and Trademark Office*